(12) United States Patent
Sun et al.

(10) Patent No.: US 11,124,537 B2
(45) Date of Patent: Sep. 21, 2021

(54) INHIBITORS OF GLUCOCORTICOID RECEPTOR

(71) Applicant: ORIC Pharmaceuticals, Inc., South San Francisco, CA (US)

(72) Inventors: Daqing Sun, Foster City, CA (US); Lawrence R. McGee, Pacifica, CA (US); Xiaohui Du, Belmont, CA (US); Liusheng Zhu, Foster City, CA (US); Xuelei Yan, Foster City, CA (US); Yosup Rew, Foster City, CA (US); John Eksterowicz, San Francisco, CA (US); Julio C. Medina, San Carlos, CA (US); Haiying Zhou, San Bruno, CA (US); Minna Delarae Balbas, San Francisco, CA (US); Valeria R. Fantin, Burlingame, CA (US)

(73) Assignee: ORIC PHARMACEUTICALS, INC., South San Francisco, CA (US)

( * ) Notice: Subject to any disclaimer, the term of this patent is extended or adjusted under 35 U.S.C. 154(b) by 0 days.

(21) Appl. No.: 16/065,626

(22) PCT Filed: Dec. 22, 2016

(86) PCT No.: PCT/US2016/068431
§ 371 (c)(1),
(2) Date: Jun. 22, 2018

(87) PCT Pub. No.: WO2017/112902
PCT Pub. Date: Jun. 29, 2017

(65) Prior Publication Data
US 2021/0017220 A1    Jan. 21, 2021

Related U.S. Application Data

(60) Provisional application No. 62/387,282, filed on Dec. 23, 2015.

(51) Int. Cl.
*C07J 43/00* (2006.01)
*C07J 41/00* (2006.01)
*A61K 45/06* (2006.01)

(52) U.S. Cl.
CPC ......... *C07J 43/003* (2013.01); *C07J 41/0083* (2013.01); *A61K 45/06* (2013.01)

(58) Field of Classification Search
CPC ...... C07J 43/003; C07J 41/0083; A61K 45/06
USPC ........................................................ 514/171
See application file for complete search history.

(56) References Cited

U.S. PATENT DOCUMENTS

| | | |
|---|---|---|
| 4,386,085 A | 5/1983 | Teutsch et al. |
| 4,447,424 A | 5/1984 | Teutsch et al. |
| 4,477,445 A | 10/1984 | Philibert et al. |
| 4,547,493 A | 10/1985 | Teutsch et al. |
| 5,006,518 A | 4/1991 | Moguilewsky et al. |
| 5,173,483 A | 12/1992 | Grandadam et al. |
| 5,405,979 A | 4/1995 | Ottow et al. |
| 5,728,689 A | 3/1998 | Cleve et al. |
| 5,843,931 A | 12/1998 | Ottow et al. |
| 5,843,933 A | 12/1998 | Cleve et al. |
| 6,451,780 B1 | 9/2002 | Chwalsz et al. |
| 6,512,130 B1 | 1/2003 | Hazra et al. |
| 8,569,274 B2 | 10/2013 | Fauser et al. |
| 8,648,105 B2 | 2/2014 | Jung et al. |
| 8,658,128 B2 | 2/2014 | Altschul et al. |
| 9,289,436 B2 | 3/2016 | Szmulewitz et al. |
| 2003/0064973 A1 | 4/2003 | Patchev et al. |
| 2004/0180869 A1 | 9/2004 | Bothe et al. |
| 2013/0029953 A1 | 1/2013 | Nickisch et al. |
| 2014/0148419 A1 | 5/2014 | Loumaye et al. |
| 2014/0364600 A1 | 12/2014 | Nickisch et al. |
| 2015/0038476 A1 | 2/2015 | Gotteland et al. |
| 2016/0151388 A1 | 6/2016 | Szmulewitz et al. |
| 2019/0218246 A1 | 7/2019 | Sun et al. |
| 2020/0055892 A1 | 2/2020 | Sun et al. |
| 2021/0002324 A1 | 1/2021 | Sun et al. |
| 2021/0017219 A1 | 1/2021 | Sun et al. |
| 2021/0023095 A1 | 1/2021 | Sun et al. |

FOREIGN PATENT DOCUMENTS

| | | |
|---|---|---|
| CN | 1222350 A | 7/1999 |
| CN | 104530166 B | 8/2016 |
| EP | 0057115 A2 | 8/1982 |
| EP | 0369881 A1 | 5/1990 |
| EP | 0404283 A2 | 12/1990 |
| EP | 0763541 A1 | 3/1997 |
| EP | 1285927 A2 | 2/2003 |
| JP | H01213296 A | 8/1989 |

(Continued)

OTHER PUBLICATIONS

Catteau et al. Expression of the glucocorticoid receptor in breast cancer-associated fibroblasts. Mol Clin Oncol 5(4):372-376 (2016).
Co-pending U.S. Appl. No. 16/889,624, filed Jun. 1, 2020.
Matsuya et al. Synthesis and evaluation of [11C]RU40555, a selective glucocorticoid receptor antagonist. Journal of Labelled Compounds and Radiopharmaceuticals 48(9):657-668 (2005).
Volden et al. The influence of glucocorticoid signaling on tumor progression. Brain Behav Immun 30 Suppl:S23-31 (2013).
Du et al. Discovery of a Potent Steroidal Glucocorticoid Receptor Antagonist with Enhanced Selectivity against the Progesterone and Androgen Receptors (OP-3633). J med Chem 62:6751-6764 (2019).
Sikora. Cancer drug development in the post-genomic age. Current Science 81(5):549-554 (2001).

(Continued)

*Primary Examiner* — Kahsay Habte
(74) *Attorney, Agent, or Firm* — Wilson Sonsini Goodrich & Rosati

(57) ABSTRACT

The present invention relates generally to compositions and methods for treating cancer and hypercortisolism. Provided herein are substituted steroidal derivative compounds and pharmaceutical compositions comprising said compounds. The subject compounds and compositions are useful for inhibition of glucocorticoid receptors. Furthermore, the subject compounds and compositions are useful for the treatment of cancer and hypercortisolism.

23 Claims, No Drawings

(56) References Cited

FOREIGN PATENT DOCUMENTS

| | | |
|---|---|---|
| JP | H02188599 A | 7/1990 |
| JP | H01914696 A | 4/1997 |
| JP | 2001508079 A | 6/2001 |
| JP | 2003119154 A | 4/2003 |
| WO | WO-9504536 A1 | 2/1995 |
| WO | WO-9517192 A1 | 6/1995 |
| WO | WO-9831702 A1 | 7/1998 |
| WO | WO-2007098382 A2 | 8/2007 |
| WO | WO-2013016725 A1 | 1/2013 |
| WO | WO-2014197653 A2 | 12/2014 |
| WO | WO-2015089338 A2 | 6/2015 |
| WO | WO-2017112902 A1 | 6/2017 |
| WO | WO-2017112904 A1 | 6/2017 |
| WO | WO-2017112909 A1 | 6/2017 |
| WO | WO-2018068021 A1 | 4/2018 |
| WO | WO-2018227129 A1 | 12/2018 |
| WO | WO-2019200156 A1 | 10/2019 |

OTHER PUBLICATIONS

U.S. Appl. No. 16/562,204 Office Action dated Dec. 31, 2019.
Zips et al. New anticancer agents: in vitro and in vivo evaluation. In Vivo 19(1):1-8 (2005).
CAS Registry No. 1060698-58-9; STN Entry date Oct. 13, 2008.
Hamilton et al. Synthesis of C-11 modified mifepristone analog libraries. Mol. Diversity 11:107-111 (2007).
Nickisch et al. Synthesis and antiprogestational properties of novel 17-fluorinated steroids. Steroids 78(9):909-19 (2013).
Nickisch et al. Synthesis and biological evaluation of partially fluorinated antiprogestins and mesoprogestins. Steroids 78(2):255-67 (2013).
U.S. Appl. No. 16/065,625 Office Action dated Jan. 26, 2021.
Hazra et al. Synthesis of 11beta-(4-dimethylaminophenyl)-17beta-hydroxy-17alpha-(3-methyl-1-butynyl)-4,9-estradien-3-one and 11beta-(4-acetophenyl)- 17beta-hydroxy-17alpha-(3-methyl-1-butynyl)-4,9-estradien-3-one: two new analogs of mifepristone (RU-486). Steroids 65:157-162 (2000).
Nickisch et al. Synthesis and biological evaluation of 11' imidazolyl antiprogestins and mesoprogestins. Steroids 92:45-55 (2014).
PCT/US2019/027062 International Search Report and Written Opinion dated Aug. 1, 2019.
Rew et al. Discovery of a Potent and Selective Steroidal Glucocorticoid Receptor Antagonist (ORIC-101). J Med Chem 61(17):7767-7784 (2018).
Stuchlik et al. Lipid-based vehicle for oral drug delivery. Biomed Papers 145(2):17-26 (2001).
Bachmann et al. Effect of chronic administration of selective glucocorticoid receptor antagonists on the rat hypothalamic-pituitary-adrenocortical axis. Neuropsychopharmacology 28(6):1056-1067 (2003).
Chemical Abstract Compound. STN Express RN 760141-59-1 (Entered STN: Oct. 10, 2004).
Chen et al. 3D-QSAR and Docking Study of the Binding Mode of Steroids to Progesterone Receptor in Active Site. QSAR Comb Sci 22:604-613 (2003).
Gebhard et al. 11,21-Bisphenyl-19-norpregnane derivatives are selective antiglucocorticoids. Bioorgan Med Chem Lett 7(17):2229-2234 (1997).
Geisler et al. An Efficient Synthesis of 11β-(4-Aminophenyl)spiro[estr-4-ene-17β,2'(5'H)-furan]-3,5'-dione. Tetrahedron 56(35):6489-6492 (2000).
Ligr et al. Mifepristone inhibits GRβ-coupled prostate cancer cell Proliferation. J Urol 188(3):981-988 (2012).
PCT/US2016/068431 International Search Report and Written Opinion dated Apr. 17, 2017.
PCT/US2016/068435 International Search Report and Written Opinion dated Apr. 17, 2017.
PCT/US2016/068448 International Search Report and Written Opinion dated Apr. 17, 2017.
PCT/US2017/055660 International Search Report and Written Opinion dated Jan. 24, 2018.
Richards et al. Synthesis and activity of novel bile-acid conjugated glucocorticoid receptor antagonists. Bioorg Med Chem Lett 16(23):6086-6090 (2006).
Taplin et al. A phase II study of mifepristone (RU-486) in castration-resistant prostate cancer, with a correlative assessment of androgen-related hormones BJU Int. 101(9):1084-1089 (2008).
U.S. Appl. No. 16/065,625 Office Action dated Apr. 30, 2021.
U.S. Appl. No. 16/065,627 Office Action dated Apr. 21, 2021.

INHIBITORS OF GLUCOCORTICOID RECEPTOR

CROSS-REFERENCE TO RELATED APPLICATIONS

This application is a § 371 U.S. National Stage Entry of International Application No. PCT/US2016/068431, filed Dec. 22, 2016, which claims the benefit of U.S. Application Ser. No. 62/387,282, filed Dec. 23, 2015, each of which are hereby incorporated by reference in their entirety.

BACKGROUND

A need exists in the art for an effective treatment of cancer, neoplastic disease, and hypercortisolism.

BRIEF SUMMARY OF THE INVENTION

Provided herein are substituted steroidal derivative compounds and pharmaceutical compositions comprising said compounds. The subject compounds and compositions are useful as inhibitors of glucocorticoid receptors (GR). Furthermore, the subject compounds and compositions are useful for the treatment of cancer, such as prostate cancer, breast cancer, lung cancer, and ovarian cancer, and hypercortisolism.

Some embodiments provided herein describe compounds having the structure of Formula (I), or a pharmaceutically acceptable salt, solvate, or prodrug thereof:

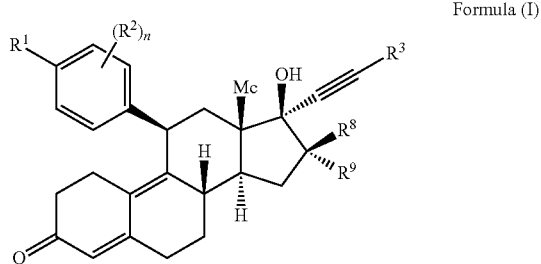

Formula (I)

wherein
$R^1$ is —$NR^4R^5$, optionally substituted alkyl$NR^4R^5$, halo, —$OR^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —C(O)$OR^6$, —C(O)$NR^4R^5$, —OC(O)$R^6$, —OC(O)$NR^4R^5$, —S(O)$_2NR^4R^5$, —S(O)$_2R^7$, —S(O)$R^7$, —$SR^7$, —$NR^4S(O)_2NR^4R^5$, —P(O)($OR^6)_2$, —P(O)($R^6)_2$, —CN, —CO$_2$H, or —NO$_2$;
each $R^2$ is independently —$NR^4R^5$, optionally substituted alkyl$NR^4R^5$, halo, —$OR^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —C(O)$R^6$, —C(O)$OR^6$, —C(O)$NR^4R^5$, —OC(O)$OR^6$, —OC(O)$NR^4R^5$, —S(O)$_2NR^4R^5$, —S(O)$_2R^7$, —S(O)$R^7$, —$SR^7$, —$NR^4S(O)_2NR^4R^5$, —CN, —CO$_2$H, or —NO$_2$;

$R^3$ is optionally substituted $C_{2-10}$ alkyl, haloalkyl, halo, deuteroalkyl, optionally substituted carbocyclyl, optionally substituted carbocyclylalkyl, optionally substituted heterocyclyl, optionally substituted heterocyclylalkyl, optionally substituted aryl, or optionally substituted heteroaryl, —Si($R^6)_3$, —$OR^6$, or —S(O)$_2R^7$;
$R^4$ and $R^5$ are each independently —H, optionally substituted alkyl, haloalkyl, optionally substituted carbocyclyl, optionally substituted aryl, optionally substituted heterocyclyl, optionally substituted heteroaryl, —S(O)$_2R^7$, —C(O)N($R^{10})_2$, —C(O)$R^6$, or —C(O)$OR^6$; or $R^4$ and $R^5$ attached to the same N atom are taken together with the N atom to which they are attached to form a substituted or unsubstituted heterocycle;
each $R^6$ is independently optionally substituted alkyl, haloalkyl, optionally substituted carbocyclyl, optionally substituted aryl, optionally substituted heterocyclyl, or optionally substituted heteroaryl;
$R^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;
$R^8$ and $R^9$ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —$OR^6$, —$NR^4R^5$, —C(O)$NR^4R^5$, —CN, —S(O)$_2R^7$, —C(O)$_2$H, —C(O)$R^6$, or —C(O)$OR^6$;
or $R^8$ and $R^9$ are taken together with the atom to which they are attached to form a substituted or unsubstituted ring containing 0-2 heteroatoms selected from the group consisting of —O—, —NH—, —$NR^6$—, —S—, and —S(O)$_2$—;
each $R^{10}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl; and
n is 0, 1, 2, 3, or 4;
wherein if $R^1$ is —$NMe_2$ and n is 0, then $R^3$ is not i-propyl; and if $R^1$ is N-bound imidazolyl and n is 0, then $R^3$ is not —$CF_3$.

In some embodiments, $R^1$ is —$NR^4R^5$, halo, —$OR^6$, optionally substituted alkyl, fluoroalkyl, optionally substituted carbocyclyl, optionally substituted heterocyclyl, optionally substituted aryl, optionally substituted heteroaryl, —C(O)$NR^4R^5$, —S(O)$_2NR^4R^5$, —S(O)$_2R^7$, —$NR^4S(O)_2NR^4R^5$, —P(O)($R^6)_2$, —P(O)($OR^6)_2$, or —CN. In certain embodiments, $R^1$ is —$NR^4R^5$, halo, —$OR^6$, —S(O)$_2NR^4R^5$, or —P(O)($OR^6)_2$. In other embodiments, $R^1$ is alkyl, fluoroalkyl, carbocyclyl, or heterocyclyl. In some embodiments, $R^1$ is pyrimidinyl, pyridinyl, pyrazinyl, triazinyl, or thiazolyl.

In some embodiments, $R^2$ is independently —$NR^4R^5$, halo, alkyl, carbocyclyl, alkoxy, or —CN. In some embodiments, $R^3$ is $C_{2-6}$ alkyl, $C_{1-6}$ fluoroalkyl, carbocyclyl, or heterocyclylalkyl. In some embodiments, $R^4$ and $R^5$ are each independently —H, alkyl, or —S(O)$_2R^7$. In some embodiments, $R^4$ and $R^5$ attached to the same N atom are taken together with the N atom to which they are attached to form a substituted or unsubstituted 4-, 5-, or 6-membered ring heterocycle additionally containing 0-3 heteroatoms selected from the group consisting of —O—, —NH—, —$NR^6$—, —S—, and —S(O)$_2$—; and $R^6$ is alkyl. In some embodiments, $R^6$ is alkyl, carbocyclyl, or fluoroalkyl. In some embodiments, R⁷ is alkyl, carbocyclyl, optionally substituted aryl, optionally substituted aralkyl, or optionally substituted heterocyclyl. In some embodiments, R⁸ and R⁹ are each independently —H, alkyl, or carbocyclyl. In certain embodiments, R⁸ and R⁹ are —H. In some embodiments, n is 0. In other embodiments, n is 1. In further embodiments, n is 2.

Other embodiments provided herein describe compounds having the structure of Formula (II), or a pharmaceutically acceptable salt, solvate, or prodrug thereof:

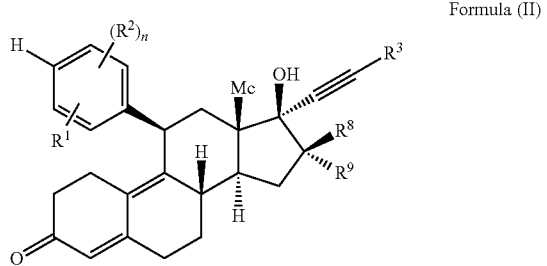

Formula (II)

wherein
R¹ is —NR⁴R⁵, optionally substituted alkylNR⁴R⁵, halo, optionally substituted alkyl, haloalkyl, optionally substituted carbocyclyl, optionally substituted carbocyclylalkyl, optionally substituted alkylheteroalkyl, optionally substituted heterocyclyl, optionally substituted heterocyclylalkyl, optionally substituted hydroxyalkyl, optionally substituted aryl, optionally substituted heteroaryl, —C(O)OR⁶, —C(O)NR⁴R⁵, —OC(O)R⁶, —OC(O)NR⁴R⁵, —S(O)₂NR⁴R⁵, —S(O)₂R⁷, —S(O)R⁷, —SR⁷, —NR⁴S(O)₂NR⁴R⁵, —P(O)(OR⁶)₂, —P(O)(R⁶)₂, —CN, —CO₂H, or —NO₂;

each R² is independently —NR⁴R⁵, optionally substituted alkylNR⁴R⁵, halo, —OR⁶, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —C(O)R⁶, —C(O)OR⁶, —C(O)NR⁴R⁵, —OC(O)OR⁶, —OC(O)NR⁴R⁵, —S(O)₂NR⁴R⁵, —S(O)₂R⁷, —S(O)R⁷, —SR⁷, —NR⁴S(O)₂NR⁴R⁵, —CN, —CO₂H, or —NO₂;

R³ is optionally substituted C₂₋₁₀ alkyl, haloalkyl, halo, optionally substituted carbocyclyl, optionally substituted carbocyclylalkyl, optionally substituted heterocyclyl, optionally substituted heterocyclylalkyl, optionally substituted aryl, optionally substituted heteroaryl, —Si(R⁶)₃, —OR⁶, or —S(O)₂R⁷;

R⁴ and R⁵ are each independently —H, optionally substituted alkyl, haloalkyl, optionally substituted carbocyclyl, optionally substituted aryl, optionally substituted heterocyclyl, optionally substituted heteroaryl, —S(O)₂R⁷, —C(O)N(R¹⁰), —C(O)R⁶, or —C(O)OR⁶; or R⁴ and R⁵ attached to the same N atom are taken together with the N atom to which they are attached to form a substituted or unsubstituted heterocycle;

each R⁶ is independently optionally substituted alkyl, haloalkyl, optionally substituted carbocyclyl, optionally substituted aryl, optionally substituted heterocyclyl, or optionally substituted heteroaryl;

R⁷ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

R⁸ and R⁹ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —OR⁶, —NR⁴R⁵, —C(O)NR⁴R⁵, —CN, —S(O)₂R⁷, —C(O)₂H, —C(O)R⁶, or —C(O)OR⁶;

or R⁸ and R⁹ are taken together with the atom to which they are attached to form a substituted or unsubstituted ring containing 0-2 heteroatoms selected from the group consisting of —O—, —NH—, —NR⁶—, —S—, and —S(O)₂—;

each R¹⁰ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl; and n is 0, 1, 2, or 3.

In some embodiments, R¹ is —NR⁴R⁵, halo, alkyl, fluoroalkyl, carbocyclyl, heterocyclyl, aryl, heteroaryl, —S(O)₂NR⁴R⁵, —S(O)₂R⁷, —NR⁴S(O)₂NR⁴R⁵, —P(O)(OR⁶)₂, or —CN. In some embodiments, R¹ is —NR⁴R⁵, halo, —S(O)₂NR⁴R⁵, or —P(O)(OR⁶)₂. In some embodiments, R¹ is alkyl, fluoroalkyl, carbocyclyl, or heterocyclyl. In some embodiments, R¹ is pyrimidinyl, pyridinyl, pyrazinyl, triazinyl, or thiazolyl.

In some embodiments, each R² is independently —NR⁴R⁵, halo, alkyl, carbocyclyl, alkoxy, or —CN. In some embodiments, R³ is C₂₋₆ alkyl, C₁₋₆ fluoroalkyl, carbocyclyl, or heterocyclylalkyl. In some embodiments, R⁴ and R⁵ are each independently —H, alkyl, or —S(O)₂R⁷. In some embodiments, R⁴ and R⁵ attached to the same N atom are taken together with the N atom to which they are attached to form a substituted or unsubstituted 4-, 5-, or 6-membered ring heterocycle containing 0-3 heteroatoms selected from the group consisting of —O—, —NH—, —NR⁶—, —S—, and —S(O)₂—; and R⁶ is alkyl. In some embodiments, R⁶ is alkyl, carbocyclyl, or fluoroalkyl. In some embodiments, R⁷ is alkyl, carbocyclyl, optionally substituted aryl, optionally substituted aralkyl, or optionally substituted heterocyclyl. In some embodiments, R⁸ and R⁹ are each independently —H, alkyl, or carbocyclyl. In some embodiments, R⁸ and R⁹ are —H. In some embodiments, n is 0. In some embodiments, n is 1.

Some embodiments provided herein describe a pharmaceutical composition comprising a pharmaceutically acceptable excipient and a compound of Formula (I) or Formula (II), or a pharmaceutically acceptable salt, solvate, or prodrug thereof.

Also provided herein are methods for treating or preventing cancer in a subject, the method comprising administering to the subject a therapeutically effective amount of a compound having the structure of Formula (I) or Formula (II), or a pharmaceutically acceptable salt, solvate, or prodrug thereof. Also provided herein are methods for reducing incidences of cancer recurrence, the method comprising administering to a subject in cancer remission a therapeutically effective amount of a compound having the structure of Formula (I) or Formula (II), or a pharmaceutically acceptable salt, solvate, or prodrug thereof. Some embodiments provided herein describe methods for treating a chemoresistant cancer in a subject, the method comprising administering to the subject a therapeutically effective amount of a compound having the structure of Formula (I) or Formula (II), or a pharmaceutically acceptable salt, solvate, or prodrug thereof.

In some embodiments, the cancer is triple negative breast cancer, high grade serous ovarian cancer, castration resistant prostate cancer, or doubly resistant prostate cancer. In some embodiments, the cancer is non-small cell lung cancer. In some embodiments, the methods further comprise administering a second therapeutic agent to the subject. In some embodiments, the methods further comprise administering one or more additional therapeutic agents. In some embodiments, the second or additional therapeutic agent is an androgen receptor signaling inhibitor. In specific embodiments, the androgen receptor signaling inhibitor is 3,3'-diindolylmethane (DIM), abiraterone acetate, ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, turosteride, or any combinations thereof. In some embodiments, the second or additional therapeutic agent is a chemotherapeutic agent. In other embodiments, the second or additional therapeutic agent is cisplatin, carboplatin, paclitaxel, gemcitabine, doxorubicin, camptothecin, topotecan, or any combinations thereof. In some embodiments, the second or additional therapeutic agent is an immunotherapy agent (e.g., an anti-PD-L1 agent or an anti-PD1 agent). In certain embodiments, the second or additional therapeutic agent is an anti-PD-L1 agent. In certain embodiments, the second or additional therapeutic agent is an anti-PD1 agent.

Other embodiments provided herein describe methods for treating a hypercortisolism disease or disorder in a subject, the method comprising administering to the subject in need thereof a therapeutically effective amount of a compound having the structure of Formula (I) or Formula (II), or a pharmaceutically acceptable salt, solvate, or prodrug thereof. In certain embodiments, the hypercortisolism disease or disorder is Cushing's syndrome. In certain embodiments, the hypercortisolism disease or disorder is refractory Cushing's syndrome.

In some embodiments of Formula (I):

$R^1$ is —H, —$NR^4R^5$, optionally substituted alkyl$NR^4R^5$, halo, —$OR^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —C(O)$OR^6$, —C(O)$NR^4R^5$, —OC(O)$R^6$, —OC(O)$NR^4R^5$, —S(O)$_2NR^4R^5$, —S(O)$_2R^7$, —S(O)$R^7$, —$SR^7$, —P(O)($OR^6$)$_2$, —P(O)($R^6$)$_2$, —CN, —$CO_2H$, or —$NO_2$;

each $R^2$ is independently —$NR^4R^5$, optionally substituted alkyl$NR^4R^5$, halo, —$OR^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —C(O)$R^6$, —C(O)$OR^6$, —C(O)$NR^4R^5$, —OC(O)$OR^6$, —OC(O)$NR^4R^5$, —S(O)$_2NR^4R^5$, —S(O)$_2R^7$, —S(O)$R^7$, —$SR^7$, —CN, —$CO_2H$, or —$NO_2$;

$R^3$ is optionally substituted $C_{2-10}$ alkyl, haloalkyl, optionally substituted carbocyclyl, optionally substituted carbocyclylalkyl, optionally substituted heterocyclyl, optionally substituted heterocyclylalkyl, optionally substituted aryl, or optionally substituted heteroaryl;

$R^4$ and $R^5$ are each independently —H, optionally substituted alkyl, haloalkyl, optionally substituted carbocyclyl, optionally substituted aryl, optionally substituted heterocyclyl, optionally substituted heteroaryl, —S(O)$_2R^7$, —C(O)$R^6$, or —C(O)$OR^6$;

or $R^4$ and $R^5$ attached to the same N atom are taken together with the N atom to which they are attached to form a substituted or unsubstituted heterocycle;

each $R^6$ is independently optionally substituted alkyl, haloalkyl, optionally substituted carbocyclyl, optionally substituted aryl, optionally substituted heterocyclyl, or optionally substituted heteroaryl;

$R^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

$R^8$ and $R^9$ are each independently —H, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, —OH, —S(O)$_2R^7$, —C(O)$_2H$, —C(O)$R^6$, or —C(O)$OR^6$;

or $R^8$ and $R^9$ are taken together with the atom to which they are attached to form a substituted or unsubstituted ring containing 0-2 heteroatoms selected from the group consisting of —O—, —NH—, —$NR^6$—, —S—, and —S(O)$_2$—; and n is 0, 1, 2, 3, or 4; wherein when $R^1$ is H, n is 1, 2, 3, or 4.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., C$_1$-C$_{15}$ alkyl). In certain embodiments, an alkyl comprises one to thirteen carbon atoms (e.g., C$_1$-C$_{13}$ alkyl). In certain embodiments, an alkyl comprises one to eight carbon atoms (e.g., C$_1$-C$_8$ alkyl). In other embodiments, an alkyl comprises one to five carbon atoms (e.g., C$_1$-C$_5$ alkyl). In other embodiments, an alkyl comprises one to four carbon atoms (e.g., C$_1$-C$_4$ alkyl). In other embodiments, an alkyl comprises one to three carbon atoms (e.g., C$_1$-C$_3$ alkyl). In other embodiments, an alkyl comprises one to two carbon atoms (e.g., C$_1$-C$_2$ alkyl). In other embodiments, an alkyl comprises one carbon atom (e.g., C$_1$ alkyl). In other embodiments, an alkyl comprises five to fifteen carbon atoms (e.g., C$_5$-C$_{15}$ alkyl). In other embodiments, an alkyl comprises five to eight carbon atoms (e.g., C$_5$-C$_8$ alkyl). In other embodiments, an alkyl comprises two to five carbon atoms (e.g., C$_2$-C$_5$ alkyl). In other embodiments, an alkyl comprises three to five carbon atoms (e.g., C$_3$-C$_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$), —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The point of attachment of the alkylene chain to the rest of the molecule and to the radical group is through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)— N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —R—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)R^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical are optionally substituted as defined above.

"Carbocyclylalkoxy" refers to a radical bonded through an oxygen atom of the formula —O—$R^c$-carbocyclyl where R is an alkylene chain as defined above. The alkylene chain and the carbocyclyl radical are optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

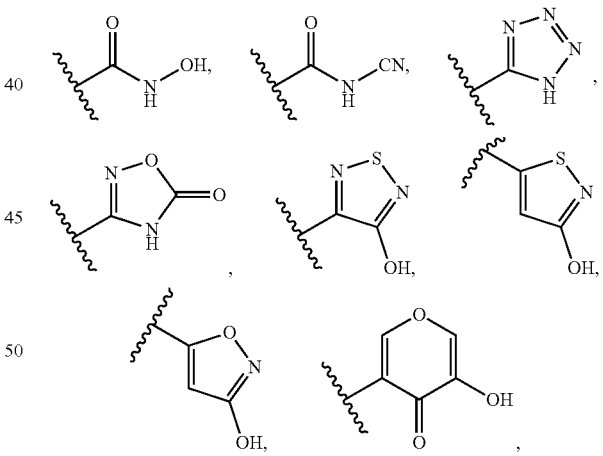

and the like.

"Deuteroalkyl" refers to an alkyl group where 1 or more hydrogen atoms of an alkyl are replaced with deuterium.

"Halo" or "halogen" refers to bromo, chloro, fluoro or iodo substituents.

"Haloalkyl" refers to an alkyl radical, as defined above, that is substituted by one or more halo radicals, as defined above, for example, trifluoromethyl, difluoromethyl, fluoromethyl, 2,2,2-trifluoroethyl, 1-fluoromethyl-2-fluoroethyl, trichloromethyl, dichloromethyl, chloromethyl, 2,2,2-trichloroethyl, 1-chloromethyl-2-chloroethyl, tribromomethyl, dibromomethyl, bromomethyl, 2,2,2-tribromoethyl, 1-bromomethyl-2-bromoethyl, and the like. In some embodiments, the alkyl part of the haloalkyl radical is optionally substituted as defined above for an alkyl group.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$heteroalkyl. Unless stated otherwise specifically in the specification, an heteroalkyl chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)— $N(R^a)$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_t R^a$ (where t is 1 or 2), —$R^b$—S(O)$R^a$ (where t is 1 or 2), —$R^b$—S(O)$_t OR^a$ (where t is 1 or 2) and —$R^b$—S(O)$_t N(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen atom and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present invention, whether radioactive or not, are encompassed within the scope of the present invention. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. In some embodiments, the compounds described herein contain one or more isotopic variants (e.g., deuterium, tritium, $^{13}$C, and/or $^{14}$C).

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

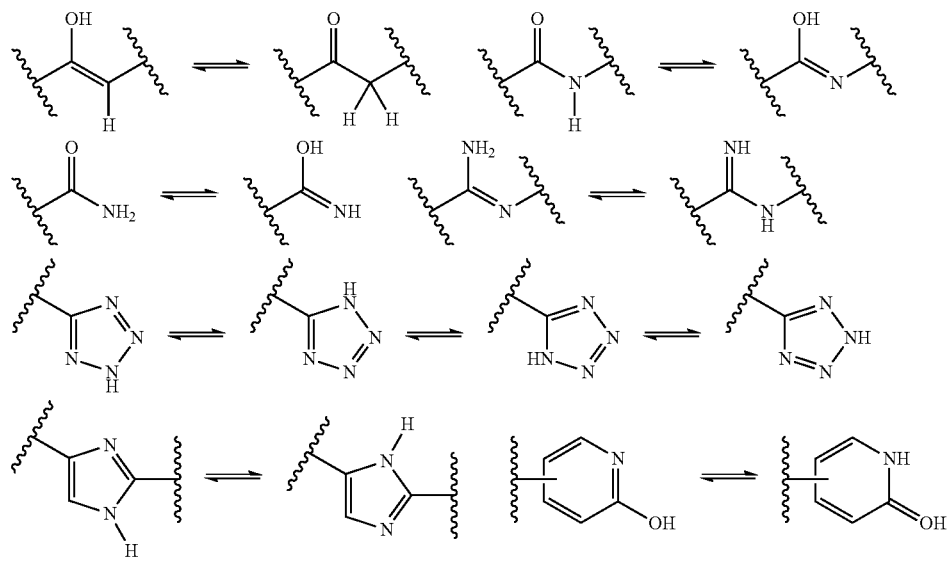

"Pharmaceutically acceptable salt" includes both acid and base addition salts. A pharmaceutically acceptable salt of any one of the substituted steroidal derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or "Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

Abbreviations used herein have their conventional meaning within the chemical and biological arts. The following abbreviations have the indicated meaning throughout: Na$_2$HPO$_4$=disodium phosphate, AcOH=acetic acid, aq.=aqueous, NH4Cl=ammonium chloride, DCM=dichloromethane, DMPU=1,3-dimethyl-3,4,5,6-tetrahydro-2(1H)-pyrimidinone, ESI=electrospray ionization, EtOAc=ethyl acetate, g=gram, h=hour, LCMS=liquid chromatography mass spectrometry, LDA=lithium diisopropylamide, MgSO$_4$=magnesium sulfate, m/s=mass-to-charge ratio, mg=milligram, MeOH=methanol, min=minute, NMR=nuclear magnetic resonance, RT or rt=room temperature, sat.=saturated, NaHCO$_3$=sodium bicarbonate, NaBH$_4$=sodium borohydride, Na$_2$CO$_3$=sodium carbonate, NaCl=sodium chloride, Na$_2$SO$_4$=sodium sulfate, Na$_2$S$_2$O$_3$=sodium thiosulfate, TFA=trifluoroacetic acid, and THF=tetrahydrofuran.

Substituted Steroidal Derivative Compounds

Substituted steroidal derivative compounds are described herein that are GR inhibitors. These compounds, and compositions comprising these compounds, are useful for the treatment of cancer, neoplastic disease, and hypercortisolism diseases and disorders.

Some embodiments provided herein describe a compound having the structure of Formula (I), or a pharmaceutically acceptable salt, solvate, or prodrug thereof:

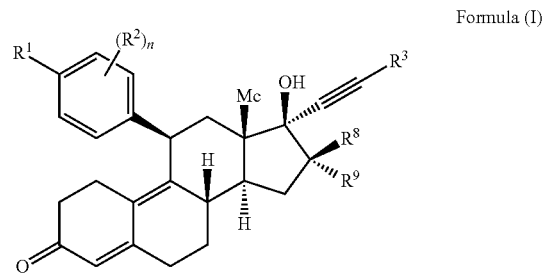

Formula (I)

wherein
$R^1$ is —H, —NR$^4$R$^5$, optionally substituted alkylNR$^4$R$^5$, halo, —OR$^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —C(O)OR$^6$, —C(O)NR$^4$R$^5$, —OC(O)OR$^6$, —OC(O)NR$^4$R$^5$, —S(O)$_2$NR$^4$R$^5$, —S(O)$_2$R$^7$, —S(O)R$^7$, —SR$^7$, —NR$^4$S(O)$_2$NR$^4$R$^5$, —P(O)(OR$^6$)$_2$, —P(O)(R$^6$)$_2$, —CN, —CO$_2$H, or —NO$_2$;

each $R^2$ is independently —NR$^4$R$^5$, optionally substituted alkylNR$^4$R$^5$, halo, —OR$^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —C(O)R$^6$, —C(O)OR$^6$, —C(O)NR$^4$R$^5$, —OC(O)OR$^6$, —OC(O)NR$^4$R$^5$, —S(O)$_2$NR$^4$R$^5$, —S(O)$_2$R$^7$, —S(O)R$^7$, —SR$^7$, —NR$^4$S(O)$_2$NR$^4$R$^5$, —CN, —CO$_2$H, or —NO$_2$;

$R^3$ is optionally substituted C$_{2-10}$ alkyl, halo, haloalkyl, deuteroalkyl, optionally substituted carbocyclyl, optionally substituted carbocyclylalkyl, optionally substituted heterocyclyl, optionally substituted heterocyclylalkyl, optionally substituted aryl, or optionally substituted heteroaryl, —Si(R$^6$)$_3$, —OR$^6$, or —S(O)$_2$R$^7$;

$R^4$ and $R^5$ are each independently —H, optionally substituted alkyl, haloalkyl, optionally substituted carbocyclyl, optionally substituted aryl, optionally substituted heterocyclyl, optionally substituted heteroaryl, —S(O)$_2$R$^7$, —C(O)N(R$^{10}$)$_2$, —C(O)R$^6$, or —C(O)OR$^6$;

or $R^4$ and $R^5$ attached to the same N atom are taken together with the N atom to which they are attached to form a substituted or unsubstituted heterocycle;

each $R^6$ is independently optionally substituted alkyl, haloalkyl, optionally substituted carbocyclyl, optionally substituted aryl, optionally substituted heterocyclyl, or optionally substituted heteroaryl;

$R^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

$R^8$ and $R^9$ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —OR⁶, —NR⁴R⁵, —C(O)NR⁴R⁵, —CN, —S(O)₂R⁷, —C(O)₂H, —C(O)R⁶, or —C(O)OR⁶;

or R⁸ and R⁹ are taken together with the atom to which they are attached to form a substituted or unsubstituted ring containing 0-2 heteroatoms selected from the group consisting of —O—, —NH—, —NR⁶—, —S—, and —S(O)₂—;

each R¹⁰ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl; and n is 0, 1, 2, 3, or 4;

wherein when R¹ is H, n is 1, 2, 3, or 4.

Some embodiments provided herein describe a compound having the structure of Formula (I), or a pharmaceutically acceptable salt, solvate, or prodrug thereof:

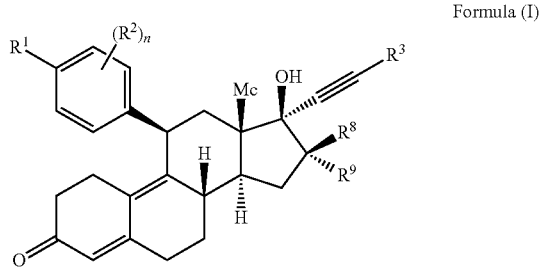

Formula (I)

wherein

R¹ is —NR⁴R⁵, optionally substituted alkylNR⁴R⁵, halo, —OR⁶, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —C(O)OR⁶, —C(O)NR⁴R⁵, —OC(O)OR⁶, —OC(O)NR⁴R⁵, —S(O)₂NR⁴R⁵, —S(O)₂R⁷, —S(O)R⁷, —SR⁷, —NR⁴S(O)₂NR⁴R⁵, —P(O)(OR⁶)₂, —P(O)(R⁶)₂, —CN, —CO₂H, or —NO₂;

each R² is independently —NR⁴R⁵, optionally substituted alkylNR⁴R⁵, halo, —OR⁶, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —C(O)R⁶, —C(O)OR⁶, —C(O)NR⁴R⁵, —OC(O)OR⁶, —OC(O)NR⁴R⁵, —S(O)₂NR⁴R⁵, —S(O)₂R⁷, —S(O)R⁷, —SR⁷, —NR⁴S(O)₂NR⁴R⁵, —CN, —CO₂H, or —NO₂;

R³ is optionally substituted C₂₋₁₀ alkyl, haloalkyl, halo, deuteroalkyl, optionally substituted carbocyclyl, optionally substituted carbocyclylalkyl, optionally substituted heterocyclyl, optionally substituted heterocyclylalkyl, optionally substituted aryl, or optionally substituted heteroaryl, —Si(R⁶)₃, —OR⁶, or —S(O)₂R⁷;

R⁴ and R⁵ are each independently —H, optionally substituted alkyl, haloalkyl, optionally substituted carbocyclyl, optionally substituted aryl, optionally substituted heterocyclyl, optionally substituted heteroaryl, —S(O)₂R⁷, —C(O)N(R¹⁰)₂, —C(O)R⁶, or —C(O)OR⁶;

or R⁴ and R⁵ attached to the same N atom are taken together with the N atom to which they are attached to form a substituted or unsubstituted heterocycle;

each R⁶ is independently optionally substituted alkyl, haloalkyl, optionally substituted carbocyclyl, optionally substituted aryl, optionally substituted heterocyclyl, or optionally substituted heteroaryl;

R⁷ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

R⁸ and R⁹ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —OR⁶, —NR⁴R⁵, —C(O)NR⁴R⁵, —CN, —S(O)₂R⁷, —C(O)₂H, —C(O)R⁶, or —C(O)OR⁶;

or R⁸ and R⁹ are taken together with the atom to which they are attached to form a substituted or unsubstituted ring containing 0-2 heteroatoms selected from the group consisting of —O—, —NH—, —NR⁶—, —S—, and —S(O)₂—;

each R¹⁰ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl; and n is 0, 1, 2, 3, or 4.

In some embodiments, if R¹ is —NMe₂ and n is 0, then R³ is not i-propyl. In some embodiments, if R¹ is N-bound imidazolyl and n is 0, then R³ is not —CF₃.

In some embodiments, if R¹ is dialkylamino, then R³ is ethyl, n-propyl, n-butyl, i-butyl, s-butyl, t-butyl, n-pentyl, t-pentyl, neo-pentyl, i-pentyl, s-pentyl, 3-pentyl, n-hexyl, i-hexyl, t-hexyl, neo-hexyl, fluoroalkyl, halo, —Si(R⁶)₃, —OR⁶, or —S(O)₂R⁷, deuteroalkyl, optionally substituted carbocyclyl, optionally substituted carbocyclylalkyl, optionally substituted heterocyclyl, optionally substituted heterocyclylalkyl, optionally substituted heteroalkyl, optionally substituted aryl, or optionally substituted heteroaryl. In some embodiments, if R¹ is dialkylamino, then n is 1, 2, 3 or 4. In some embodiments, if R¹ is dialkylamino, then R⁸ or R⁹ is not H. In some embodiments, if R¹ is dialkylamino, then R⁸ or R⁹ is alkyl or carbocyclyl. In certain embodiments, if R¹ is —NMe₂ and n is 0, then R³ is ethyl, n-propyl, n-butyl, i-butyl, s-butyl, t-butyl, n-pentyl, t-pentyl, neo-pentyl, i-pentyl, s-pentyl, 3-pentyl, n-hexyl, i-hexyl, t-hexyl, neo-hexyl, fluoroalkyl, optionally substituted carbocyclyl, optionally substituted carbocyclylalkyl, optionally substituted heterocyclyl, optionally substituted heterocyclylalkyl, optionally substituted heteroalkyl, optionally substituted aryl, or optionally substituted heteroaryl. In certain embodiments, if R¹ is —NMe₂, then n is 1, 2, 3 or 4. In some embodiments, if R¹ is —NMe₂, then R⁸ or R⁹ is not H. In some embodiments, if R¹ is —NMe₂, then R⁸ or R⁹ is alkyl or carbocyclyl.

In some embodiments, if R¹ is N-bound heteroaryl, then R³ is optionally substituted C₂₋₁₀ alkyl, C₂₋₁₀ fluoroalkyl, halo, —Si(R⁶)₃, —OR⁶, or —S(O)₂R⁷, deuteroalkyl, optionally substituted carbocyclyl, optionally substituted carbocyclylalkyl, optionally substituted heterocyclyl, optionally substituted heterocyclylalkyl, optionally substituted aryl, or optionally substituted heteroaryl. In some embodiments, if R¹ is N-bound heteroaryl, then n is 1, 2, 3 or 4. In some embodiments, if $R^1$ is N-bound heteroaryl, then $R^8$ or $R^9$ is not H. In some embodiments, if $R^1$ is N-bound heteroaryl, then $R^8$ or $R^9$ is alkyl or carbocyclyl. In some embodiments, if $R^1$ is N-bound imidazolyl, then $R^3$ is optionally substituted $C_{2\text{-}10}$ alkyl, $C_{2\text{-}10}$ fluoroalkyl, halo, $-\text{Si}(R^6)_3$, $-OR^6$, or $-S(O)_2R^7$, optionally substituted carbocyclyl, optionally substituted carbocyclylalkyl, optionally substituted heterocyclyl, optionally substituted heterocyclylalkyl, optionally substituted aryl, or optionally substituted heteroaryl. In some embodiments, if $R^1$ is N-bound imidazolyl, then n is 1, 2, 3 or 4. In some embodiments, if $R^1$ is N-bound imidazolyl, then $R^8$ or $R^9$ is not H. In some embodiments, if $R^1$ is N-bound imidazolyl, then $R^8$ or $R^9$ is alkyl or carbocyclyl.

In some embodiments, $R^1$ is $-NR^4R^5$, alkyl$NR^4R^5$, halo, $-OR^6$, $-OH$, alkyl, haloalkyl, carbocyclyl, carbocyclylalkyl, heteroalkyl, heterocyclyl, heterocyclylalkyl, hydroxyalkyl, optionally substituted aryl, optionally substituted heteroaryl, $-S(O)_2NR^4R^5$, $-S(O)_2R^7$, $-NR^4S(O)_2NR^4R^5$, $-P(O)(OR^6)_2$, $-P(O)(R^6)_2$, or $-CN$;

each $R^2$ is independently $-NR^4R^5$ halo, $-OR^6$, $-OH$, alkyl, haloalkyl, carbocyclyl, carbocyclylalkyl, heteroalkyl, heterocyclyl, heterocyclylalkyl, hydroxyalkyl, $-S(O)_2NR^4R^5$, $-S(O)_2R^7$, $-NR^4S(O)_2NR^4R^5$, or $-CN$;

$R^3$ is optionally substituted $C_{2\text{-}10}$ alkyl, haloalkyl, halo, $-\text{Si}(R^6)_3$, $-OR^6$, $-S(O)_2R^7$, deuteroalkyl, optionally substituted carbocyclyl, optionally substituted carbocyclylalkyl, optionally substituted heterocyclyl, optionally substituted heterocyclylalkyl, optionally substituted aryl, or optionally substituted heteroaryl;

$R^4$ and $R^5$ are each independently $-H$, alkyl, carbocyclyl, carbocyclylalkyl, $-S(O)_2R^7$, $-C(O)N(R^{10})$, $-C(O)R^6$, or $-C(O)OR^6$;

or $R^4$ and $R^5$ attached to the same N atom are taken together with the N atom to which they are attached to form a substituted or unsubstituted heterocycle;

each $R^6$ is independently alkyl, haloalkyl, or aryl;

$R^7$ is alkyl, haloalkyl, carbocyclyl, or aryl;

$R^8$ and $R^9$ are each independently $-H$, alkyl, haloalkyl, halo, carbocyclyl, carbocyclylalkyl, heteroalkyl, heterocyclyl, heterocyclylalkyl, $-OH$, $-OR^6$, $-NR^4R^5$, $-C(O)NR^4R^5$, $-CN$, $-S(O)_2R^7$, $-C(O)_2H$, $-C(O)R^6$, or $-C(O)OR^6$;

or $R^8$ and $R^9$ are taken together with the atom to which they are attached to form a ring; and each $R^{10}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl; and n is 1, 2, 3, or 4.

In some embodiments, $R^1$ is $-NR^4R^5$, halo, $-OR^6$, alkyl, haloalkyl, substituted or unsubstituted carbocyclyl, heteroalkyl, deuteroalkyl, substituted or unsubstituted heterocyclyl, substituted or unsubstituted heteroaryl, hydroxyalkyl, $-S(O)_2NR^4R^5$, $-S(O)_2R^7-$, or $-CN$;

each $R^2$ is independently $-NR^4R^5$ halo, $-OR^6$, $-OH$, alkyl, haloalkyl, carbocyclyl, heteroalkyl, heterocyclyl, hydroxyalkyl, $-S(O)_2NR^4R^5$, $-S(O)_2R^7$, or $-CN$;

$R^3$ is optionally substituted $C_{2\text{-}10}$ alkyl, haloalkyl, halo, $-\text{Si}(R^6)_3$, $-OR^6$, $-S(O)_2R^7$, deuteroalkyl, carbocyclyl, carbocyclylalkyl, heterocyclyl, optionally substituted aryl, or heteroaryl;

$R^4$ and $R^5$ are each independently $-H$, alkyl, carbocyclyl, carbocyclylalkyl, $-S(O)_2R^7$, $-C(O)N(R^{10})$, $-C(O)R^6$, or $-C(O)OR^6$;

or $R^4$ and $R^5$ attached to the same N atom are taken together with the N atom to which they are attached to form a substituted or unsubstituted heterocycle;

each $R^6$ is independently alkyl or haloalkyl;

$R^7$ is alkyl;

$R^8$ and $R^9$ are each independently $-H$, alkyl, alkoxy, or hydroxy;

or $R^8$ and $R^9$ are taken together with the atom to which they are attached to form a ring; and each $R^{10}$ is independently H, alkyl, hydroxyalkyl, haloalkyl, carbocyclyl; and n is 0, 1, or 2.

In some embodiments, $R^1$ is $-NR^4R^5$, halo, $-OR$, alkyl, haloalkyl, carbocyclyl, carbocyclylalkyl, heteroalkyl, deuteroalkyl, heterocyclyl optionally substituted with alkyl, heteroaryl optionally substituted with alkyl, hydroxyalkyl, or $-S(O)_2NR^4R^5$;

each $R^2$ is independently halo, $-OR^6$, or alkyl;

$R^3$ is $C_{2\text{-}6}$ alkyl, $C_{2\text{-}6}$ hydroxyalkyl, haloalkyl, halo, $-S(O)_2R^7$, deuteroalkyl, carbocyclyl, carbocyclylalkyl, heterocyclyl, aryl optionally substituted with methylsulfonyl or dialkylamino, or heteroaryl;

$R^4$ and $R^5$ are each independently alkyl, carbocyclyl, carbocyclylalkyl, $-S(O)_2R^7$, or $-C(O)R^6$ or $R^4$ and $R^5$ attached to the same N atom are taken together with the N atom to which they are attached to form a substituted or unsubstituted heterocycle;

each $R^6$ is independently alkyl;

$R^7$ is alkyl;

$R^8$ and $R^9$ are each independently $-H$;

each $R^{10}$ is independently H or alkyl; and n is 0, 1, or 2.

In some embodiments, $R^1$ is $-NR^4R^5$, halo, $-OR^6$, alkyl, haloalkyl, carbocyclyl, carbocyclylalkyl, heteroalkyl, deuteroalkyl, heterocyclyl optionally substituted with alkyl, heteroaryl optionally substituted with alkyl, hydroxyalkyl, or $-S(O)_2NR^4R^5$;

each $R^2$ is independently halo, $-OR^6$, or $C_{1\text{-}3}$ alkyl;

$R^3$ is $C_{2\text{-}6}$ alkyl, $C_{2\text{-}6}$ hydroxyalkyl, haloalkyl, halo, $-S(O)_2R^7$, deuteroalkyl, carbocyclyl, carbocyclylalkyl, heterocyclyl, aryl optionally substituted with methylsulfonyl or $-NMe_2$, or heteroaryl;

$R^4$ and $R^5$ are each independently alkyl, carbocyclyl, carbocyclylalkyl, $-S(O)_2R^7$, or $-C(O)R^6$ or $R^4$ and $R^5$ attached to the same N atom are taken together with the N atom to which they are attached to form a substituted or unsubstituted heterocycle;

each $R^6$ is independently $C_{1\text{-}6}$ alkyl;

$R^7$ is methyl;

$R^8$ and $R^9$ are each independently $-H$;

each $R^{10}$ is independently H or $C_{1\text{-}6}$ alkyl; and n is 1 or 2.

In some embodiments, $R^1$ is $-NR^4R^5$, halo, $-OR^6$, $-OH$, alkyl, haloalkyl, carbocyclyl, carbocyclylalkyl, heterocyclyl, heterocyclylalkyl, hydroxyalkyl, phenyl, $-C(O)OR^6$, $-C(O)NR^4R^5$, $-S(O)_2NR^4R^5$, $-S(O)_2R^7$, $-NR^4S(O)_2NR^4R^5$, $-P(O)(OR^6)_2$, $-P(O)(R^6)_2$, or $-CN$;

each $R^2$ is independently $-NR^4R^5$, alkyl$NR^4R^5$, halo, $-OR^6$, $-OH$, alkyl, haloalkyl, carbocyclyl, carbocyclylalkyl, heteroalkyl, heterocyclyl, heterocyclylalkyl, hydroxyalkyl, $-C(O)R^6$, $-C(O)OR^6$, $-C(O)NR^4R^5$, $-OC(O)OR^6$, $-OC(O)NR^4R^5$, $-S(O)_2NR^4R^5$, $-S(O)_2R^7$, $-NR^4S(O)_2NR^4R^5$, or $-CN$;

R³ is optionally substituted $C_{2-10}$ alkyl, haloalkyl, halo, —Si(R⁶)₃, —OR⁶, or —S(O)₂R⁷, deuteroalkyl, optionally substituted carbocyclyl, optionally substituted carbocyclylalkyl, optionally substituted heterocyclyl, optionally substituted heterocyclylalkyl, optionally substituted aryl, or optionally substituted heteroaryl;

R⁴ and R⁵ attached to the same N atom are taken together with the N atom to which they are attached to form a substituted or unsubstituted heterocycle;

each R⁶ is independently alkyl, haloalkyl, or aryl;

R⁷ is alkyl, haloalkyl, carbocyclyl, or aryl;

R⁸ and R⁹ are each independently —H, alkyl, haloalkyl, halo, carbocyclyl, carbocyclylalkyl, heteroalkyl, heterocyclyl, heterocyclylalkyl, —OH, —OR⁶, —NR⁴R⁵, —C(O)NR⁴R⁵, —CN, —S(O)₂R⁷, —C(O)₂H, —C(O)R⁶, or —C(O)OR⁶;

or R⁸ and R⁹ are taken together with the atom to which they are attached to form a ring; and each R¹⁰ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl; and n is 1.

In some embodiments,

R¹ is —NR⁴R⁵, halo, —OR⁶, alkyl, haloalkyl, substituted or unsubstituted carbocyclyl, heteroalkyl, deuteroalkyl, substituted or unsubstituted heterocyclyl, substituted or unsubstituted heteroaryl, hydroxyalkyl, —S(O)₂NR⁴R⁵, —S(O)₂R⁷—, or —CN;

each R² is independently —NR⁴R⁵ halo, —OR⁶, —OH, alkyl, haloalkyl, carbocyclyl, heteroalkyl, heterocyclyl, hydroxyalkyl, —S(O)₂NR⁴R⁵, —S(O)₂R⁷, or —CN;

R³ is optionally substituted $C_{2-10}$ alkyl, haloalkyl, halo, —Si(R⁶)₃, —OR⁶, —S(O)₂R⁷, deuteroalkyl, carbocyclyl, carbocyclylalkyl, heterocyclyl, optionally substituted aryl, or heteroaryl;

R⁴ and R⁵ are each independently —H, alkyl, carbocyclyl, carbocyclylalkyl, —S(O)₂R⁷, —C(O)N(R¹)₂, —C(O)R⁶, or —C(O)OR⁶;

or R⁴ and R⁵ attached to the same N atom are taken together with the N atom to which they are attached to form a substituted or unsubstituted heterocycle;

each R⁶ is independently alkyl, haloalkyl or phenyl;

R⁷ is alkyl or dialkylamino;

R⁸ and R⁹ are each independently —H, alkyl, alkoxy, or hydroxy;

or R⁸ and R⁹ are taken together with the atom to which they are attached to form a ring; and each R¹⁰ is independently H, alkyl, hydroxyalkyl, haloalkyl, carbocyclyl; and n is 0.

In some embodiments,

R¹ is —NR⁴R⁵, halo, —OR⁶, alkyl, haloalkyl, carbocyclyl, carbocyclylalkyl, heteroalkyl, deuteroalkyl, heterocyclyl optionally substituted with alkyl, heteroaryl optionally substituted with alkyl, hydroxyalkyl, or —S(O)₂NR⁴R⁵;

each R² is independently halo, —OR⁶, or alkyl;

R³ is $C_{2-6}$ alkyl, $C_{2-6}$ hydroxyalkyl, haloalkyl, halo, —S(O)₂R⁷, deuteroalkyl, carbocyclyl, carbocyclylalkyl, heterocyclyl, aryl optionally substituted with methylsulfonyl or dialkylamino, or heteroaryl;

R⁴ and R⁵ are each independently alkyl, carbocyclyl, carbocyclylalkyl, —S(O)₂R⁷, or —C(O)R⁶ or R⁴ and R⁵ attached to the same N atom are taken together with the N atom to which they are attached to form a substituted or unsubstituted heterocycle;

each R⁶ is independently alkyl;

R⁷ is alkyl;

R⁸ and R⁹ are each independently —H;

each R¹⁰ is independently H or alkyl; and n is 0.

In some embodiments,

R¹ is —NR⁴R⁵, halo, —OR⁶, alkyl, haloalkyl, carbocyclyl, deuteroalkyl, heterocyclyl optionally substituted with alkyl, heteroaryl optionally substituted with alkyl, hydroxyalkyl, or —S(O)₂NR⁴R⁵;

each R² is independently halo, —OR⁶, or $C_{1-3}$ alkyl;

R³ is $C_{2-6}$ alkyl;

R⁴ and R⁵ are each independently alkyl, carbocyclyl, carbocyclylalkyl, —S(O)₂R⁷, or —C(O)R⁶;

or R⁴ and R⁵ attached to the same N atom are taken together with the N atom to which they are attached to form a substituted or unsubstituted heterocycle;

each R⁶ is independently $C_{1-6}$ alkyl;

R⁷ is methyl or —NMe₂;

R⁸ and R⁹ are each independently —H;

each R¹⁰ is independently H or $C_{1-6}$ alkyl; and n is 0.

For any and all of the embodiments of Formula (I), substituents are selected from among a subset of the listed alternatives.

In some embodiments, R¹ is —NR⁴R⁵, optionally substituted alkylNR⁴R⁵, halo, optionally substituted alkyl, fluoroalkyl, optionally substituted carbocyclyl, optionally substituted carbocyclylalkyl, optionally substituted heterocyclyl, optionally substituted heterocyclylalkyl, optionally substituted hydroxyalkyl, optionally substituted aryl, optionally substituted heteroaryl, —C(O)N R⁴R⁵, —OC(O)OR⁶, —OC(O)N⁴R⁵, —S(O)₂NR⁴R⁵, —S(O)₂R⁷, —S(O)R⁷, —SR⁷, —NR⁴S(O)₂NR⁴R⁵, —P(O)(OR⁶)₂, —P(O)(R⁶)₂, —CN, or —NO₂. In some embodiments, R¹ is —NR⁴R⁵, halo, —OR⁶, optionally substituted alkyl, fluoroalkyl, optionally substituted carbocyclyl, optionally substituted heterocyclyl, optionally substituted aryl, optionally substituted heteroaryl, —C(O)NR⁴R⁵, —S(O)₂NR⁴R⁵, —S(O)₂R⁷, —NR⁴S(O)₂NR⁴R⁵, —P(O)(R⁶)₂, —P(O)(OR⁶)₂, or —CN. In some embodiments, R¹ is —NR⁴R⁵, halo, —OR⁶, $C_{1-6}$alkyl, $C_{1-6}$fluoroalkyl, $C_{3-6}$carbocyclyl, $C_{3-6}$heterocyclyl, aryl, heteroaryl, —C(O)NR⁴R⁵, —S(O)₂NR⁴R⁵, —S(O)₂R⁷, —NR⁴S(O)₂NR⁴R⁵, —P(O)(R⁶)₂, —P(O)(OR⁶)₂, or —CN. In some embodiments, R¹ is —NR⁴R⁵, halo, —OR⁶, —S(O)₂NR⁴R⁵, —P(O)(R⁶)₂, or —P(O)(OR⁶)₂. In other embodiments, R¹ is —NMe₂, —NHMe, —NH₂, methyl, ethyl, propyl, iso-propyl, butyl, iso-butyl, sec-butyl, tert-butyl, methoxy, ethoxy, propoxy, iso-propoxy, morpholino, or pyrrolidino. In certain embodiments, R¹ is $C_{1-6}$alkyl, fluoroalkyl, $C_{3-6}$carbocyclyl, or $C_{3-6}$heterocyclyl. In some embodiments, R¹ is —NR⁴R⁵. In some embodiments, R¹ is —NMe₂. In some embodiments, R¹ is —NHMe. In some embodiments, R¹ is —NH₂. In some embodiments, R¹ is —NMeEt. In some embodiments, R¹ is —NEt₂.

In some embodiments, R¹ is halo. In some embodiments, R¹ is fluoro. In some embodiments, R¹ is chloro. In some embodiments, R¹ is bromo. In some embodiments, R¹ is $C_{1-6}$alkyl. In some embodiments, R¹ is methyl. In some embodiments, R¹ is ethyl. In some embodiments, R¹ is propyl. In some embodiments, R¹ is iso-propyl. In some embodiments, R¹ is carbocyclyl. In some embodiments, R¹ is cyclopropyl. In some embodiments, R¹ is cyclobutyl. In some embodiments, R¹ is cyclopentyl. In some embodiments, R¹ is cyclohexyl. In some embodiments, R¹ is —OR⁶. In some embodiments, R¹ is methoxy. In some embodiments, $R^1$ is ethoxy. In some embodiments, $R^1$ is propoxy. In some embodiments, $R^1$ is iso-propoxy. In some embodiments, $R^1$ is heterocyclyl. In some embodiments, $R^1$ is azetadino, morpholino, thiomorpholino, piperidino, piperazino, or pyrrolidino. In some embodiments, $R^1$ is morpholino. In some embodiments, $R^1$ is pyrrolidino. In some embodiments, $R^1$ is azetadino.

In other embodiments, $R^1$ is optionally substituted monocyclic aryl, optionally substituted bicyclic aryl, optionally substituted monocyclic heteroaryl, or optionally substituted bicyclic heteroaryl. In certain embodiments, $R^1$ is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, $R^1$ is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, $R^1$ is pyrimidinyl, pyridinyl, pyrazinyl, triazinyl, or thiazolyl. In certain embodiments, $R^1$ is C-bound imidazolyl. In certain embodiments, $R^1$ is N-bound imidazolyl. In some embodiments, $R^1$ is pyrimidinyl. In some embodiments, $R^1$ is pyrimidinyl optionally substituted with alkyl or alkoxy. In some embodiments, $R^1$ is pyrazinyl. In some embodiments, $R^1$ is triazinyl. In some embodiments, $R^1$ is thiazolyl.

In certain embodiments, $R^1$ is optionally substituted with halo, alkyl, hydroxy, alkoxy, or fluoroalkyl. In certain embodiments, $R^1$ is optionally substituted with halo, alkyl, or alkoxy. In some embodiments, $R^1$ is optionally substituted with fluoro or $C_{1-6}$alkyl. In some embodiments, $R^1$ is optionally substituted with fluoro or methyl. In some embodiments, $R^1$ is optionally substituted with methyl or methoxy.

In some embodiments, each $R^2$ is independently —$NR^4R^5$, optionally substituted alkyl$NR^4R^5$, halo, —$OR^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —$C(O)R^6$, —$C(O)NR^4R^5$, —$S(O)_2NR^4R^5$, —$S(O)_2R^7$, —$NR^4S(O)_2NR^4R^5$, or —CN. In some embodiments, each $R^2$ is independently —$NR^4R^5$, alkyl$NR^4R^5$, halo, —$OR^6$, —OH, alkyl, haloalkyl, carbocyclyl, carbocyclylalkyl, heteroalkyl, heterocyclyl, heterocyclylalkyl, hydroxyalkyl, —$C(O)R^6$, —$C(O)NR^4R^5$, —$S(O)_2NR^4R^5$, —$S(O)_2R^7$, —$NR^4S(O)_2NR^4R^5$, or —CN. In certain embodiments, each $R^2$ is independently —$NR^4R^5$, halo, —$OR^6$, —OH, optionally substituted alkyl, fluoroalkyl, optionally substituted carbocyclyl, optionally substituted heteroalkyl, optionally substituted heterocyclyl, optionally substituted hydroxyalkyl, —$S(O)_2NR^4R^5$, —$S(O)_2R^7$, —$NR^4S(O)_2NR^4R^5$, or —CN. In some embodiments, each $R^2$ is independently —$NR^4R^5$, $C_{1-6}$alkyl$NR^4R^5$, halo, —$OR^6$, —OH, $C_{1-6}$alkyl, $C_{1-6}$fluoroalkyl, $C_{3-6}$carbocyclyl, $C_{1-6}$alkyl$C_{3-6}$carbocyclyl, $C_{1-6}$heteroalkyl, $C_{3-6}$heterocyclyl, $C_{1-6}$alkyl$C_{3-6}$heterocyclyl, $C_{1-6}$hydroxyalkyl, or —CN. In some embodiments, each $R^2$ is independently —$C(O)R^6$, —$C(O)NR^4R^5$, —$S(O)_2NR^4R^5$, —$S(O)_2R^7$, or —CN. In some embodiments, each $R^2$ is independently —$NR^4R^5$, halo, —$OR^6$, $C_{1-6}$alkyl, $C_{1-6}$fluoroalkyl, $C_{3-6}$carbocyclyl, $C_{1-6}$heteroalkyl, $C_{3-6}$heterocyclyl, or —CN. In some embodiments, each $R^2$ is independently —$NR^4R^5$, halo, alkyl, carbocyclyl, alkoxy, or —CN. In some embodiments, each $R^2$ is independently —$NR^4R^5$, halo, alkyl, or alkoxy. In some embodiments, each $R^2$ is independently methyl, methoxy, ethyl, propyl, iso-propyl, cyclopropyl, fluoro, chloro, or —$NMe_2$. In some embodiments, each $R^2$ is independently methyl, methoxy, iso-propyl, cyclopropyl, fluoro, chloro, or —$NMe_2$. In some embodiments, $R^2$ is methoxy. In some embodiments, $R^2$ is methyl. In some embodiments $R^2$ is ethyl. In some embodiments, $R^2$ is iso-propyl. In some embodiments, $R^2$ is propyl. In some embodiments, $R^2$ is cyclopropyl. In some embodiments, $R^2$ is cyclobutyl. In some embodiments, $R^2$ is fluoro. In some embodiments, $R^2$ is chloro. In some embodiments, $R^2$ is —$NMe_2$. In some embodiments, $R^2$ is —$NH_2$. In some embodiments, $R^2$ is —NHMe. In some embodiments, $R^2$ is —NMeEt.

In some embodiments, n is 1, 2, or 3, and each $R^2$ is independently halo, optionally substituted alkyl, or haloalkyl. In some embodiments, n is 2, and each $R^2$ is independently fluoro, chloro, methyl, ethyl, propyl, or butyl. In some embodiments, n is 3, and each $R^2$ is independently fluoro, chloro, methyl, ethyl, propyl, or butyl.

In certain embodiments, each $R^2$ is independently optionally substituted with halo, alkyl, hydroxy, alkoxy, or fluoroalkyl. In some embodiments, each $R^2$ is independently optionally substituted with fluoro or $C_{1-6}$alkyl. In some embodiments, each $R^2$ is independently optionally substituted with fluoro or methyl.

In some embodiments, $R^3$ is $C_{2-10}$ alkyl, haloalkyl, halo, deuteroalkyl, carbocyclyl, carbocyclylalkyl, heterocyclyl, heterocyclylalkyl, aryl, or heteroaryl. In some embodiments, $R^3$ is optionally substituted $C_{2-10}$ alkyl, haloalkyl, deuteroalkyl, carbocyclyl, optionally substituted aryl, optionally substituted heteroaryl, —$Si(R^6)_3$, —$OR^6$, or —$S(O)_2R^7$ wherein $R^3$ is optionally substituted with halo, alkyl, alkoxy, hydroxy, —$NR^4R^5$, or —$S(O)_2R^7$. In some embodiments, $R^3$ is $C_{3-6}$ alkyl, $C_{1-6}$ haloalkyl, halo, $C_{1-6}$ deuteroalkyl, $C_{3-6}$ carbocyclyl, $C_{3-6}$ carbocyclyl$C_{1-6}$ alkyl, $C_{3-6}$heterocyclyl, $C_{3-6}$ heterocyclyl$C_{1-6}$ alkyl. In some embodiments, $R^3$ is $C_{2-6}$ alkyl, $C_{1-6}$ fluoroalkyl, halo, carbocyclyl, or heterocyclylalkyl. In some embodiments, $R^3$ is $C_{2-6}$ alkyl. In some embodiments, $R^3$ is $C_{3-6}$ alkyl. In some embodiments, $R^3$ is i-propyl. In some embodiments, $R^3$ is t-butyl. In some embodiments, $R^3$ is butyl. In some embodiments, $R^3$ is isobutyl. In some embodiments, $R^3$ is sec-butyl. In some embodiments, $R^3$ is carbocyclyl. In some embodiments, $R^3$ is cyclopropyl. In some embodiments, $R^3$ is cyclobutyl. In some embodiments, $R^3$ is cyclopentyl. In some embodiments, $R^3$ is cyclohexyl. In some embodiments, $R^3$ is $C_1$ deuteroalkyl, $C_2$ deuteroalkyl, $C_3$ deuteroalkyl, $C_4$ deuteroalkyl, or $C_5$ deuteroalkyl. In some embodiments, $R^3$ is $C_1$ monodeuteroalkyl, $C_1$ dideuteroalkyl, or $C_1$ trideuteroalkyl. In some embodiments, $R^3$ is $C_1$ trideuteroalkyl. In some embodiments, $R^3$ is substituted $C_{2-10}$ alkyl, wherein the one or more substituents are halo, alkyl, hydroxy, alkoxy, chloroalkyl, or fluoroalkyl. In some embodiments, $R^3$ is substituted $C_{2-6}$ alkyl, wherein the one or more substituents is $C_{1-3}$ alkoxy, hydroxy or halo. In some embodiments, $R^3$ is substituted $C_{2-4}$ alkyl, wherein the one or more substituents is methoxy, hydroxyl, or fluoro.

In some embodiments, $R^3$ is halo. In some embodiments, $R^3$ is fluoro. In some embodiments, $R^3$ is chloro. In some embodiments, $R^3$ is bromo. In some embodiments, $R^3$ is trifluoromethyl. In some embodiments, $R^3$ is hydroxyalkyl. In some embodiments, $R^3$ is deuteromethyl. In some embodiments, $R^3$ is —$Si(R^6)_3$. In some embodiments, $R^3$ is —Si(Me)$_3$. In some embodiments, R$^3$ is —Si(Ph)$_3$. In some embodiments, R$^3$ is —OR$^6$. In some embodiments, R$^3$ is —S(O)$_2$R$^7$.

In other embodiments, R$^3$ is optionally substituted aryl or optionally substituted heteroaryl. In certain specific embodiments, R$^3$ is phenyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, R$^3$ is phenyl optionally substituted with halo, alkyl, alkoxy, hydroxy, cyano, —NR$^4$R$^5$, or —S(O)$_2$R$^7$. In some embodiments, R$^3$ is pyridinyl optionally substituted with halo, alkyl, alkoxy, hydroxy, —NR$^4$R$^5$, or —S(O)$_2$R$^7$. In some embodiments, R$^3$ is phenyl. In some embodiments, R$^3$ is pyridinyl.

In certain embodiments, R$^3$ is optionally substituted with halo, alkyl, hydroxy, alkoxy, —NR$^4$R$^5$, —S(O)$_2$R$^7$ or fluoroalkyl. In some embodiments, R$^3$ is optionally substituted with chloro, fluoro, methyl, ethyl, propyl, iso-propyl, butyl, iso-butyl, sec-butyl, tert-butyl, hydroxy, methoxy, ethoxy, propoxy, iso-propoxy, cyano, dimethylamino, diethylamino, methylamino, amino, —S(O)$_2$Me, or trifluoromethyl. In certain embodiments, R$^3$ is optionally substituted with chloro, fluoro, methyl, hydroxy, methoxy, cyano, dimethylamino, —S(O)$_2$Me, or trifluoromethyl. In certain embodiments, R$^3$ is phenyl substituted with chloro, fluoro, methyl, ethyl, propyl, butyl, hydroxy, methoxy, cyano, —S(O)$_2$Me, or trifluoromethyl. In some embodiments, R$^3$ is phenyl substituted with methyl, ethyl, propyl, t-butyl, cyano, —S(O)$_2$Me, or trifluoromethyl. In certain embodiments, R$^3$ is pyridyl substituted with chloro, fluoro, methyl, ethyl, propyl, butyl, hydroxy, methoxy, cyano, —S(O)$_2$Me, or trifluoromethyl. In some embodiments, R$^3$ is pyridyl substituted with methyl, ethyl, propyl, t-butyl, cyano, —S(O)$_2$Me, or trifluoromethyl.

In some embodiments, R$^3$ is optionally substituted heterocyclyl, wherein the heterocyclyl is

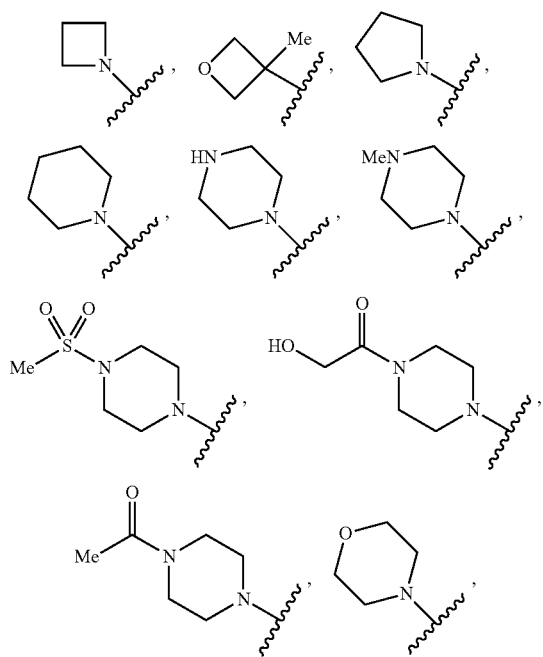

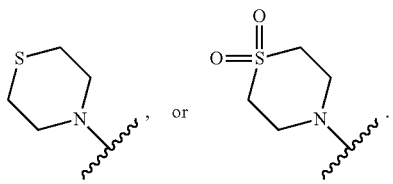

In some embodiments, R$^3$ is heterocyclyl, wherein the heterocyclyl is

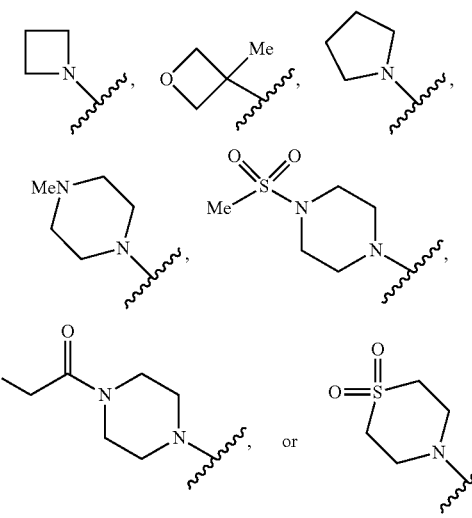

In some embodiments, R$^4$ and R$^5$ are each independently —H, optionally substituted alkyl, fluoroalkyl, optionally substituted carbocyclyl, optionally substituted carbocyclylalkyl, optionally substituted heterocyclyl, optionally substituted heterocyclylalkyl, —S(O)$_2$R$^7$, or —C(O)N(R$^{10}$)$_2$. In some embodiments, R$^4$ and R$^5$ are each independently —H, C$_{1-6}$ alkyl, C$_{1-6}$ fluoroalkyl, C$_{3-6}$ carbocyclyl, C$_{1-6}$ carbocyclylalkyl, C$_{2-6}$ heterocyclyl, C$_{1-6}$ alkylC$_{3-6}$heterocyclyl, —S(O)$_2$R$^7$, or —C(O)N(R$^{10}$)$_2$. In some embodiments, R$^4$ and R$^5$ are each independently —H, C$_{1-6}$alkyl, C$_{1-6}$fluoroalkyl, C$_{3-6}$carbocyclyl, C$_{3-5}$heterocyclyl, or —S(O)$_2$R$^7$. In some embodiments, R$^4$ and R$^5$ are each independently —H, C$_{1-6}$alkyl, or —S(O)$_2$R$^7$. In some embodiments, R$^4$ and R$^5$ are each independently —H, methyl, ethyl, propyl, isopropyl, butyl, sec-butyl, iso-butyl, tert-butyl, or —S(O)$_2$R$^7$. In some embodiments, R$^4$ is methyl. In some embodiments, R$^4$ is ethyl. In some embodiments, R$^4$ is propyl. In some embodiments, R$^5$ is methyl, ethyl, or propyl. In some embodiments, R$^4$ is —C(O)N(R$^{10}$)$_2$. In some embodiments, R$^4$ is C$_{1-6}$ alkylC$_{3-6}$heterocyclyl. In some embodiments, R$^4$ is —S(O)$_2$R$^7$. In some embodiments, R$^4$ and R$^5$ are —H. In some embodiments, R$^4$ and R$^5$ are methyl. In some embodiments, R$^4$ and R$^5$ are each independently —H or —C(O)N(R$^{10}$)$_2$.

In some embodiments, R$^4$ and R$^5$ are each independently C$_{1-6}$alkyl, optionally substituted with substituents selected from halo, alkyl, hydroxy, alkoxy, chloroalkyl, or fluoroalkyl. In some embodiments, R$^4$ and R$^5$ are each independently substituted with chloro, fluoro, cyano, methoxy, ethoxy, propoxy, chloroalkyl, or fluoroalkyl.

In other embodiments, $R^4$ and $R^5$ attached to the same N atom are taken together with the N atom to which they are attached to form a substituted or unsubstituted 4-, 5-, or 6-membered ring heterocycle additionally containing 0-3 heteroatoms selected from —O—, —NH—, —$NR^6$—, —S—, and —$S(O)_2$—. In some embodiments, $R^4$ and $R^5$ attached to the same N atom are taken together with the N atom to which they are attached to form a 4-, 5- or 6-membered heterocycle additionally containing 0 or 1 oxygen heteroatom. In other embodiments, $R^4$ and $R^5$ attached to the same N atom are taken together with the N atom to which they are attached to form a substituted or unsubstituted 4-, 5-, or 6-membered ring heterocycle additionally containing 1 heteroatoms selected from —O—, —NH—, —$NR^6$—, —S—, and —$S(O)_2$—. In other embodiments, $R^4$ and $R^5$ attached to the same N atom are taken together with the N atom to which they are attached to form a 4-, 5-, or 6-membered ring heterocycle additionally containing 1 oxygen heteroatom. In other embodiments, $R^4$ and $R^5$ attached to the same N atom are taken together with the N atom to which they are attached to form a substituted or unsubstituted 4-, 5-, or 6-membered ring. In some embodiments, the substituted or unsubstituted 4-, 5-, or 6-membered ring is In some embodiments, 5-membered ring is or

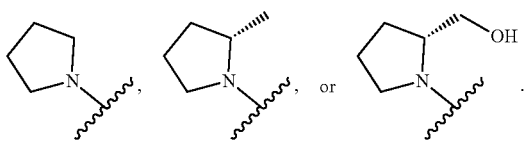

In some embodiments, the 6-membered ring is

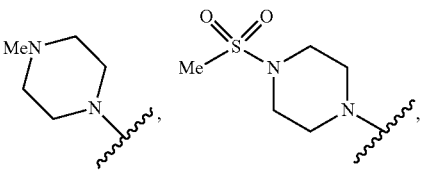

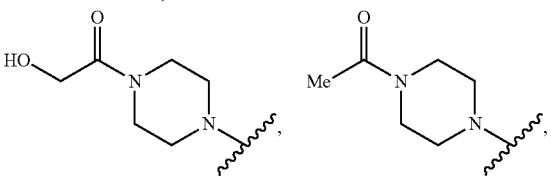

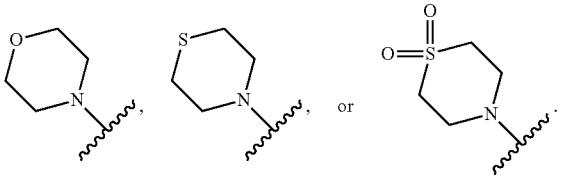

In some embodiments, the 6-membered ring is

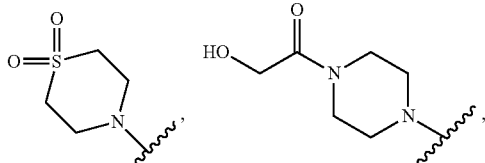

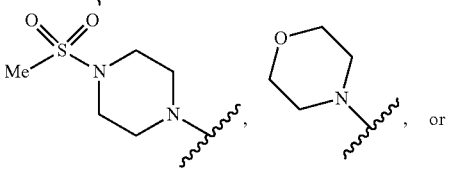

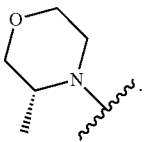

In other embodiments, $R^4$ and $R^5$ attached to the same N atom are taken together with the N atom to which they are attached to form a substituted 4-, 5-, or 6-membered ring, wherein the substituents are selected from halo, alkyl, hydroxy, alkoxy, chloroalkyl, or fluoroalkyl. In some embodiments, the heterocycle is substituted with chloro, fluoro, cyano, methoxy, ethoxy, hydroxymethylene, methylsulfonyl, chloroalkyl, or fluoroalkyl. In some embodiments, the heterocycle is substituted with chloro, fluoro, cyano, methoxy, ethoxy, chloroalkyl, or fluoroalkyl.

In certain embodiments, $R^4$ and $R^5$ are each independently optionally substituted with halo, alkyl, hydroxy, hydroxylalkylene, alkylsulfonyl, alkoxy, or fluoroalkyl. In certain embodiments, $R^4$ and $R^5$ are each independently optionally substituted with halo, alkyl, hydroxy, alkoxy, or fluoroalkyl. In some embodiments, $R^4$ and $R^5$ are each independently optionally substituted with fluoro or $C_{1-6}$alkyl. In some embodiments, $R^4$ and $R^5$ are each independently optionally substituted with fluoro or methyl.

In some embodiments, $R^6$ is optionally substituted alkyl, fluoroalkyl, optionally substituted aryl, optionally substituted carbocyclyl, or optionally substituted heterocyclyl. In some embodiments, $R^6$ is optionally substituted alkyl, fluoroalkyl, optionally substituted carbocyclyl, or optionally substituted heterocyclyl. In some embodiments, $R^6$ is alkyl, aryl, carbocyclyl, or heterocyclyl. In some embodiments, $R^6$ is alkyl, carbocyclyl, or heterocyclyl. In some embodiments, $R^6$ is alkyl, carbocyclyl, or fluoroalkyl. In some embodiments, $R^6$ is $C_{1-6}$alkyl, $C_{1-6}$fluoroalkyl, $C_{3-6}$carbocyclyl, or $C_{3-6}$heterocyclyl. In certain embodiments, $R^6$ is $C_{1-6}$alkyl. In certain embodiments, $R^6$ is methyl, ethyl, propyl, iso-propyl, butyl, sec-butyl, iso-butyl, or tert-butyl. In some embodiments, $R^6$ is phenyl.

In some embodiments, $R^7$ is alkyl, carbocyclyl, optionally substituted aryl, optionally substituted aralkyl, or optionally substituted heterocyclyl. In some embodiments, $R^7$ is $C_{1-6}$alkyl, $C_{3-6}$carbocyclyl, or aryl optionally substituted with halo or alkyl. In some embodiments, $R^7$ is $C_{1-6}$alkyl, $C_{3-6}$carbocyclyl, or phenyl optionally substituted with halo or alkyl. In some embodiments, $R^7$ is optionally substituted benzyl. In some embodiments, $R^7$ is $C_{3-6}$carbocyclyl. In some embodiments, $R^7$ is phenyl. In some embodiments, $R^7$ is phenyl substituted with 1-4 $C_{1-6}$alkyl or fluoro substituents. In some embodiments, $R^7$ is phenyl substituted with a $C_{1-6}$alkyl or fluoro substituent. In some embodiments, $R^7$ is alkyl, carbocyclyl, aralkyl, or heterocyclyl.

In certain embodiments, $R^7$ is optionally substituted with halo, alkyl, hydroxy, alkoxy, or fluoroalkyl. In some embodiments, $R^7$ is optionally substituted with fluoro or $C_{1-6}$alkyl. In some embodiments, $R^7$ is optionally substituted with fluoro or methyl.

In some embodiments, $R^8$ and $R^9$ are each independently —H, $C_{1-6}$alkyl, $C_{1-6}$haloalkyl, halo, $C_{3-6}$carbocyclyl, $C_{1-6}$alkyl$C_{3-6}$carbocyclyl, $C_{1-6}$heteroalkyl, $C_{3-6}$heterocyclyl, $C_{1-6}$alkyl$C_{3-6}$heterocyclyl, —OH, —OR$^6$, —NR$^4$R$^5$, —C(O)NR$^4$R$^5$, —CN, —S(O)$_2$R$^7$, —C(O)$_2$H, —C(O)R$^6$, or —C(O)OR$^6$ or $R^8$ and $R^9$ are taken together with the atom to which they are attached to form a ring containing 0-2 heteroatoms selected from the group consisting of —O—, —NH—, —NR$^6$—, —S—, and —S(O)$_2$—. In some embodiments, $R^8$ and $R^9$ are each independently —H, $C_{1-6}$alkyl, or $C_{3-6}$carbocyclyl, methoxy, ethoxy, propoxy, iso-propoxy, —NH$_2$, —NMe$_2$, —NHMe, —NEt$_2$, —C(O)NH$_2$, —C(O)NMe$_2$, —C(O)NHMe, or —CN. In some embodiments, $R^8$ and $R^9$ are each independently —H, $C_{1-6}$alkyl, $C_{1-6}$fluoroalkyl, halo, or $C_{3-6}$carbocyclyl. In some embodiments, $R^8$ and $R^9$ are each independently —H, $C_{1-6}$alkyl, or $C_{3-6}$carbocyclyl. In some embodiments, $R^8$ is —H and $R^9$ is $C_{1-6}$alkyl, $C_{1-6}$fluoroalkyl, halo, or $C_{3-6}$carbocyclyl. In some embodiments, $R^8$ is —H and $R^9$ is alkyl. In some embodiments, $R^8$ is $C_{1-6}$alkyl, $C_{1-6}$fluoroalkyl, halo, or $C_{3-6}$carbocyclyl and $R^9$ is —H. In some embodiments, $R^8$ is methyl and $R^9$ is —H. In some embodiments, $R^8$ and $R^9$ are —H. In some embodiments, $R^8$ and $R^9$ are $C_{1-6}$alkyl. In some embodiments, $R^8$ and $R^9$ are methyl. In some embodiments, $R^8$ is fluoro or chloro. In some embodiments, $R^9$ is fluoro or chloro.

In other embodiments, $R^8$ and $R^9$ are taken together with the atom to which they are attached to form a 3-, 4-, 5-, or 6-membered ring containing 0-2 heteroatoms selected from the group consisting of —O—, —NH—, —NR$^6$—, —S—, and —S(O)$_2$—. In some embodiments, $R^8$ and $R^9$ are taken together with the atom to which they are attached to form a 3-, 4-, 5-, or 6-membered carbocyclic ring.

In some embodiments, each $R^{10}$ is independently hydrogen, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl. In some embodiments, each $R^{10}$ is independently hydrogen, optionally substituted alkyl, optionally substituted carbocyclyl, optionally substituted heteroalkyl, or optionally substituted aryl. In some embodiments, each $R^{10}$ is independently optionally substituted alkyl, optionally substituted carbocyclyl, optionally substituted heteroalkyl, optionally substituted aryl, or heteroaryl. In some embodiments, each $R^{10}$ is independently alkyl or aryl. In some embodiments, each $R^{10}$ is independently hydrogen or $C_{1-6}$ alkyl. In some embodiments, each $R^{10}$ is independently hydrogen, methyl, ethyl, propyl, iso-propyl, butyl, iso-butyl, sec-butyl, tert-butyl, pentyl or hexyl. In some embodiments, each $R^1$ is independently hydrogen, methyl, ethyl, propyl, iso-propyl, butyl, or tert-butyl. In some embodiments, each $R^{10}$ is independently hydrogen or methyl. In some embodiments, $R^{10}$ is H. In other embodiments, $R^{10}$ is alkyl. In other embodiments, $R^{10}$ is methyl. In some embodiments, $R^{10}$ is ethyl. In other embodiments, $R^{10}$ is propyl. In other embodiments, $R^{10}$ is substituted alkyl. In some embodiments, $R^{10}$ is methyl substituted with halo, —OH, or —CN. In some embodiments, $R^{10}$ is ethyl substituted with halo, —OH, or —CN. In some embodiments, $R^{10}$ is propyl substituted with halo, —OH, or —CN. In other embodiments, $R^{10}$ is aryl.

In some embodiments, n is 0, 1, or 2. In some embodiments, n is 0. In some embodiments, n is 1 or 2. In some embodiments, n is 1. In some embodiments, n is 2. In some embodiments, n is 3 or 4.

In some embodiments, compounds described herein have the following structure of Formula (Ia):

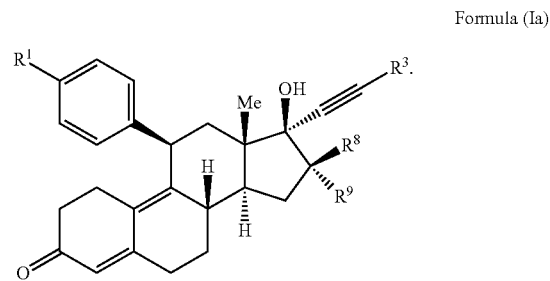

Formula (Ia)

In some embodiments, compounds described herein have the following structure of Formula (Ib):

Formula (Ib)

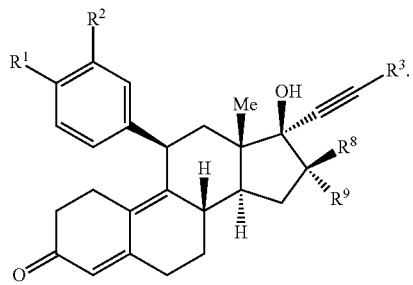

In some embodiments, compounds described herein have the following structure of Formula (Ic):

Formula (Ic)

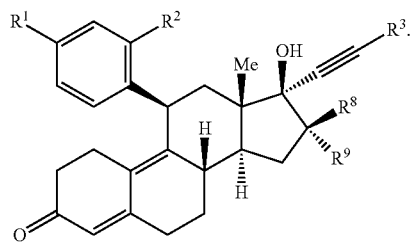

In some embodiments, compounds described herein have the following structure of Formula (Id):

Formula (Id)

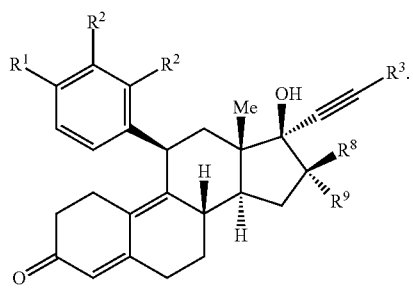

In some embodiments, compounds described herein have the following structure of Formula (Ie):

Formula (Ie)

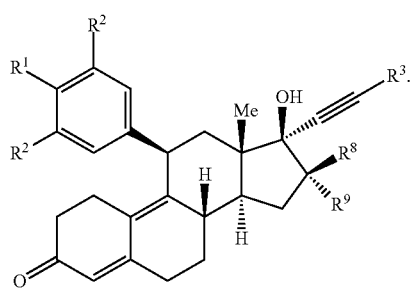

In some embodiments, compounds described herein have the following structure of Formula (If):

Formula (If)

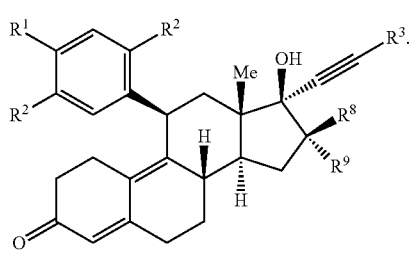

In some embodiments, compounds described herein have the following structure of Formula (Ig):

Formula (Ig)

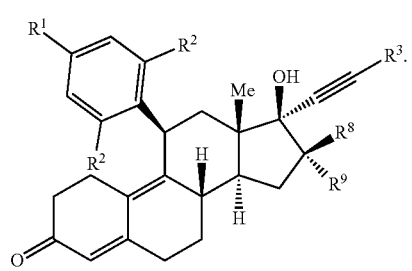

In some embodiments, compounds described herein have the following structure of Formula (Ih):

Formula (Ih)

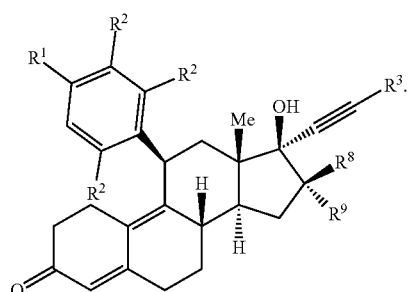

In some embodiments, compounds described herein have the following structure of Formula (Ii):

Formula (Ii)

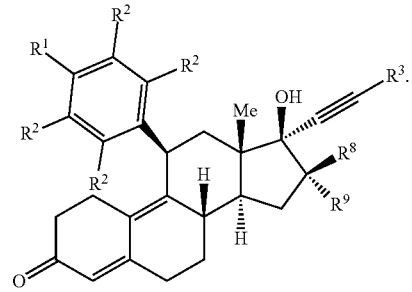

In some embodiments, compounds described herein have the following structure of Formula (Ij):
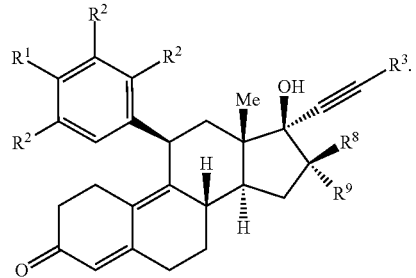
Formula (Ij)
Some embodiments provided herein describe a compound having the structure:
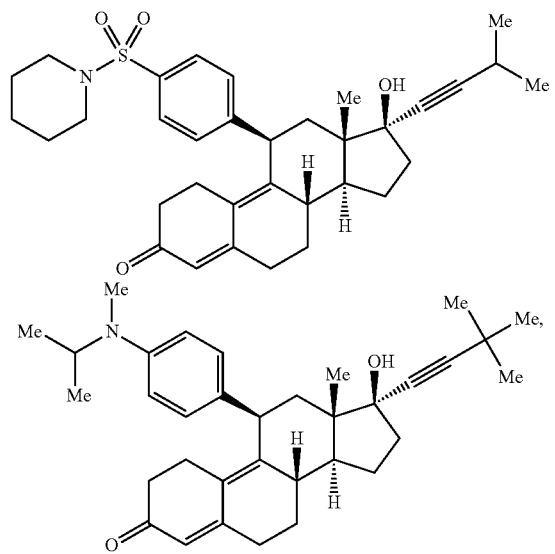
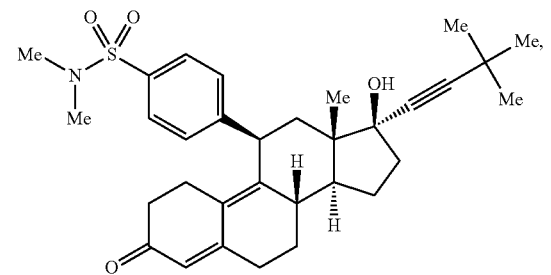
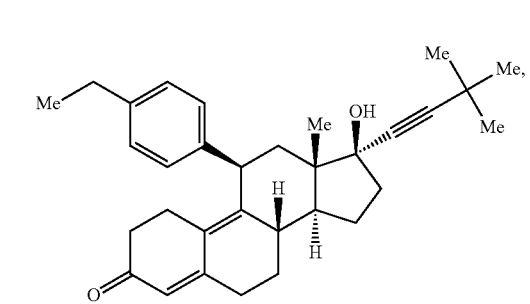
-continued
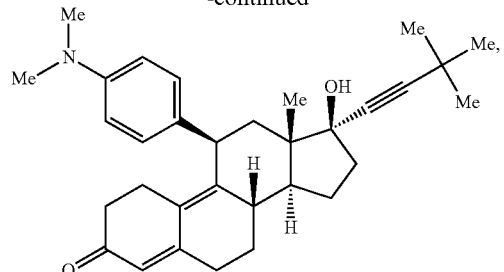
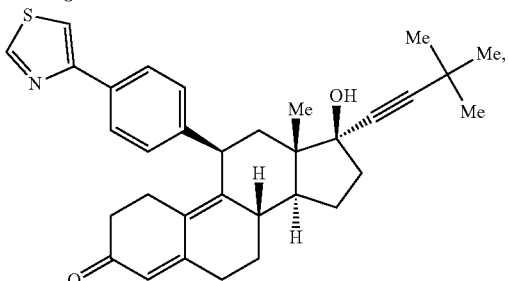
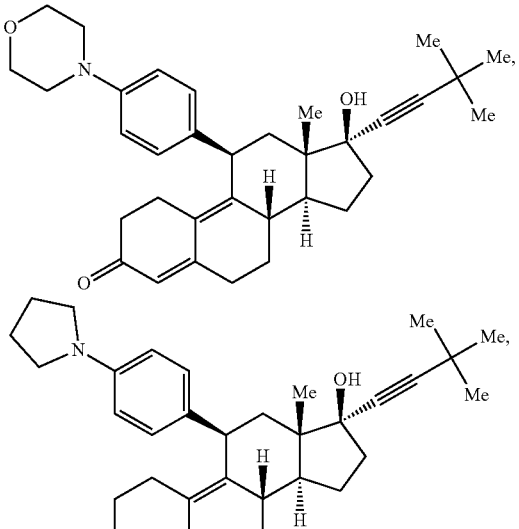
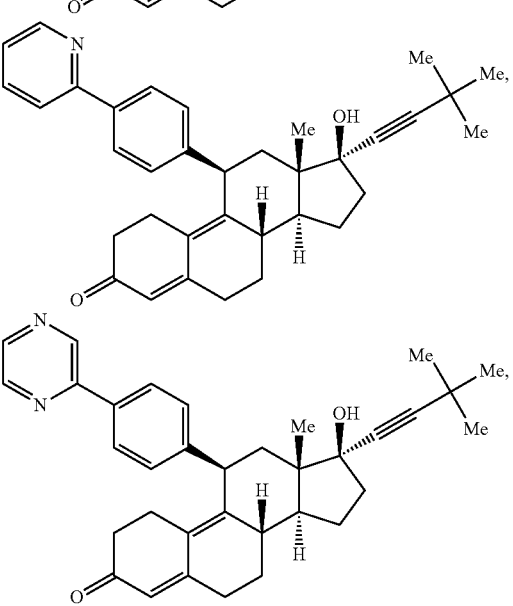

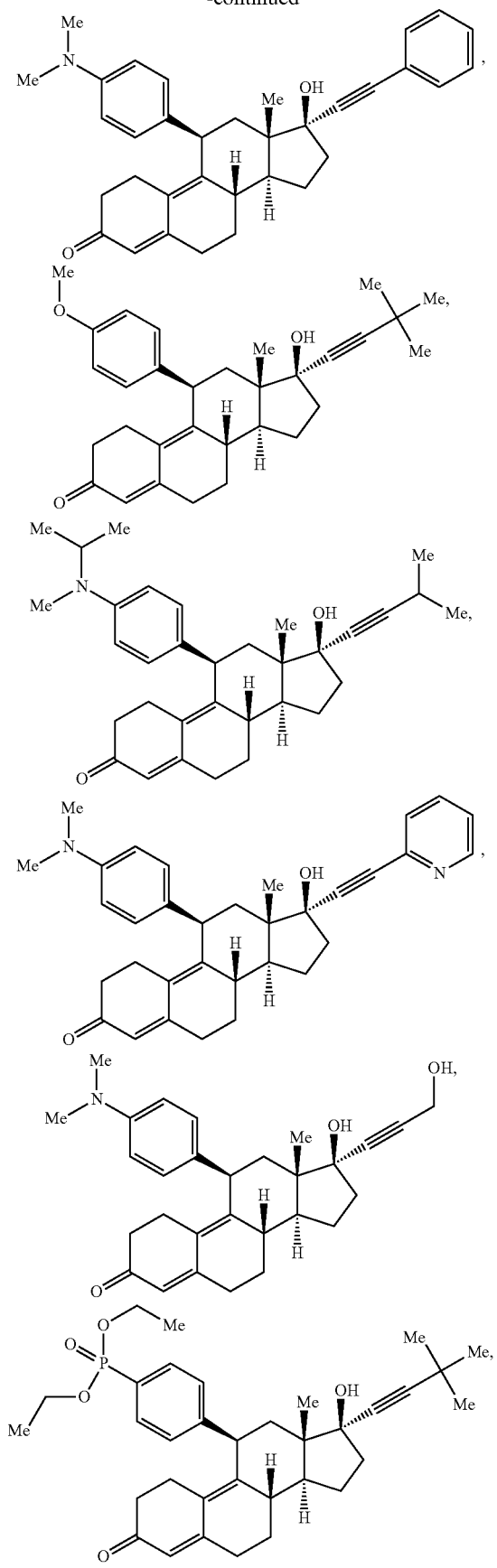
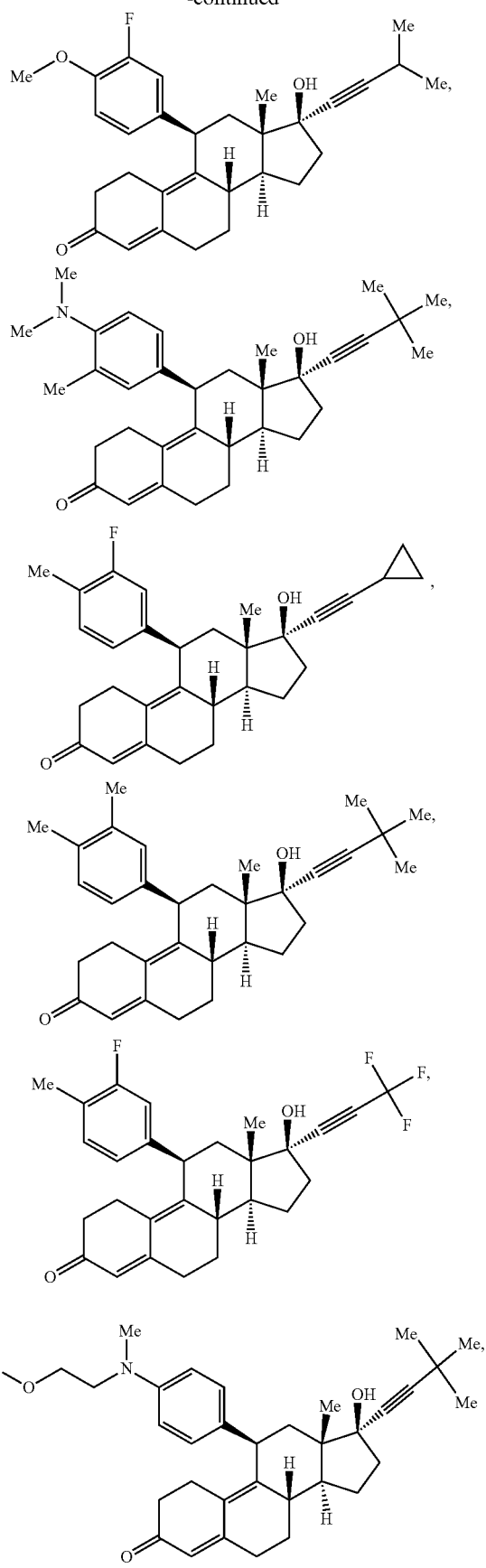

41
-continued
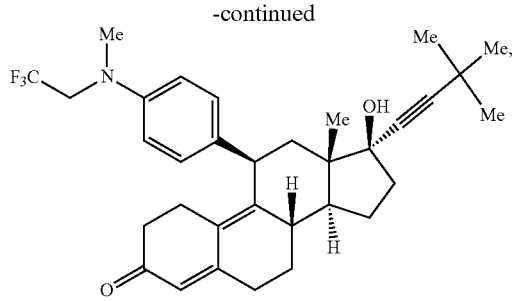
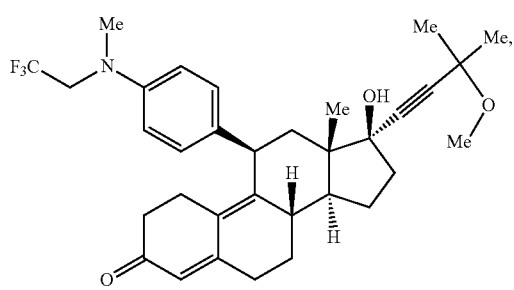
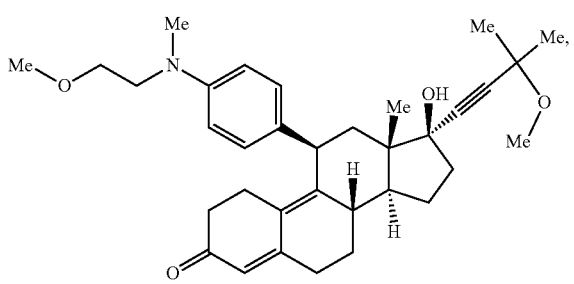
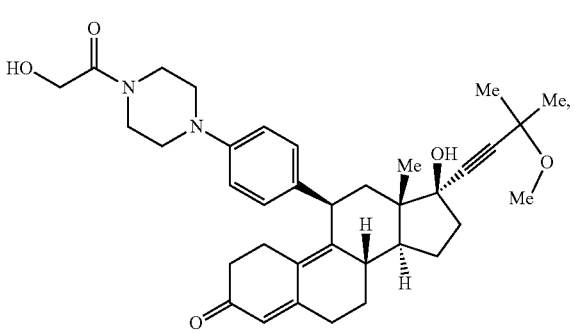
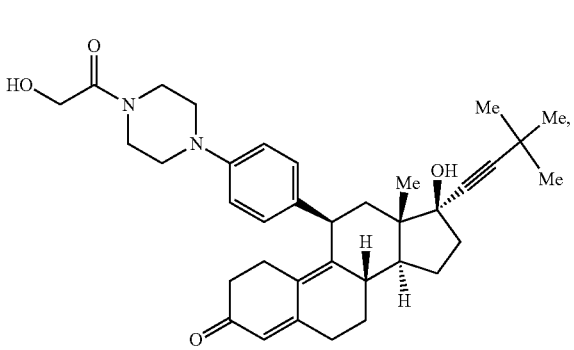
42
-continued
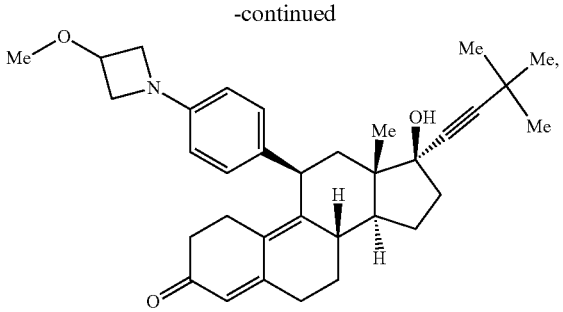
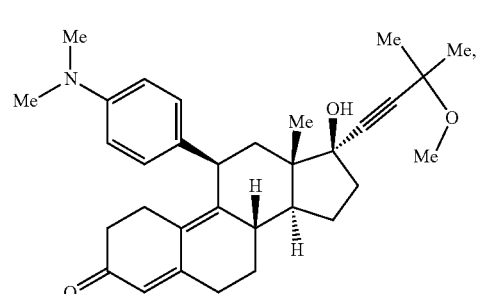
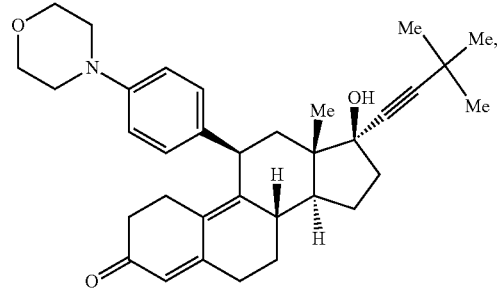
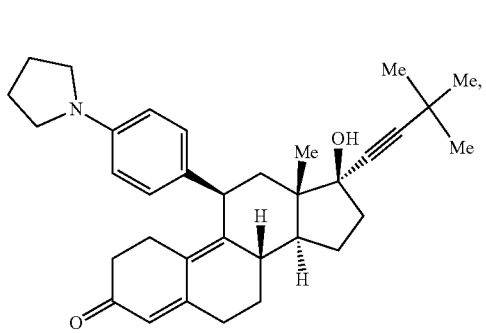
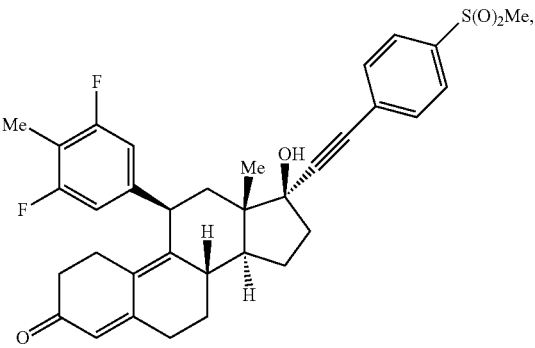

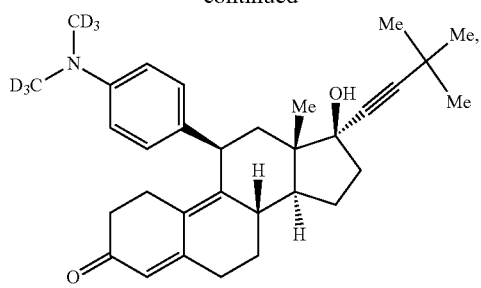
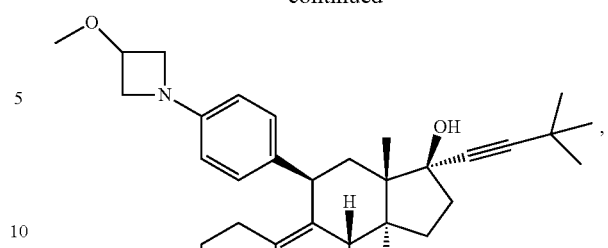
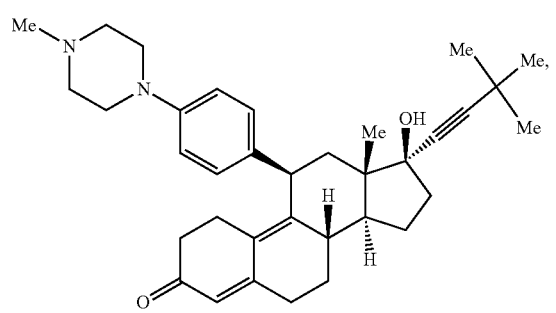
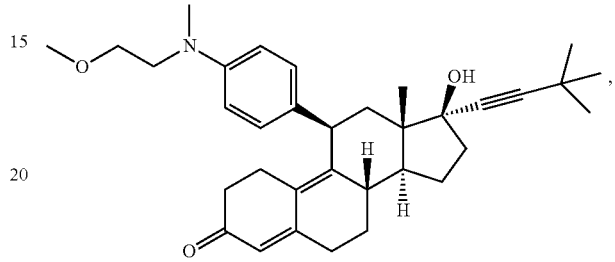
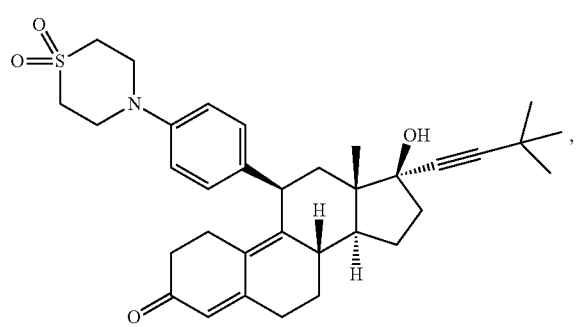
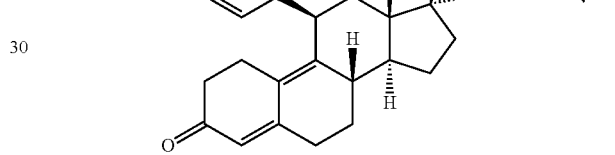
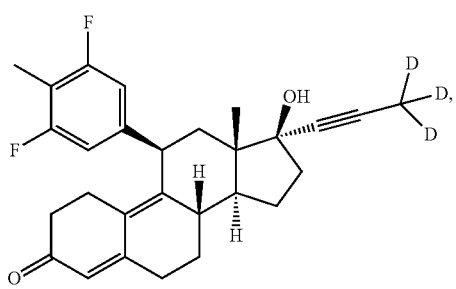
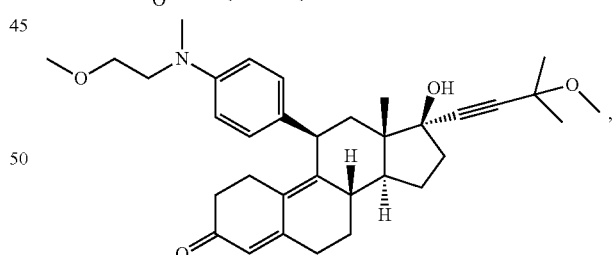
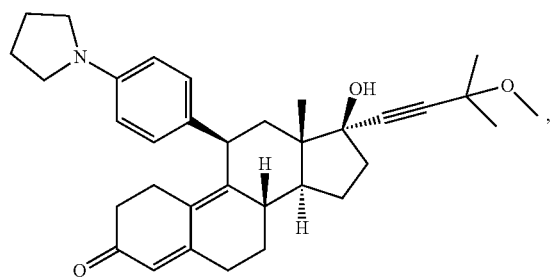
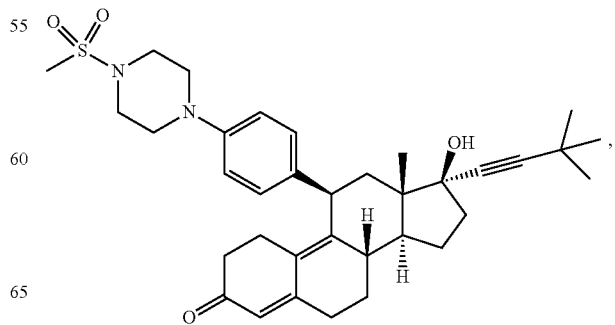

45
-continued
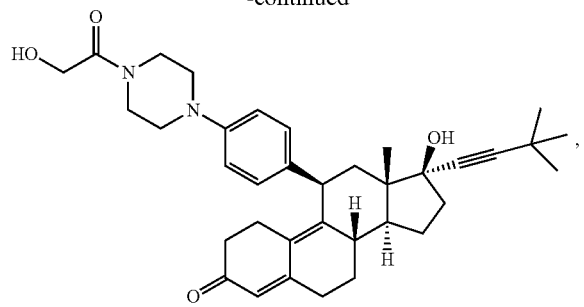
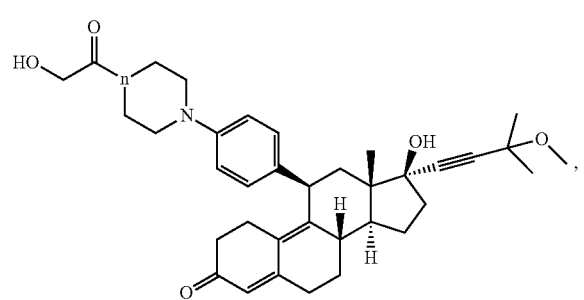
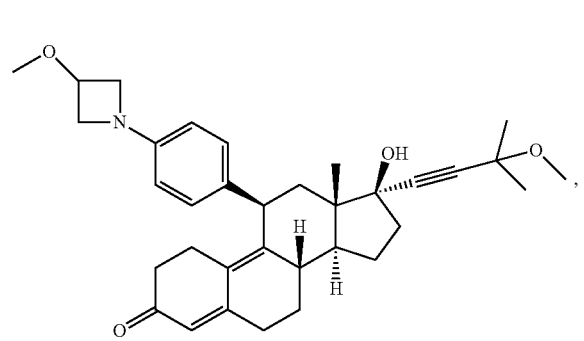
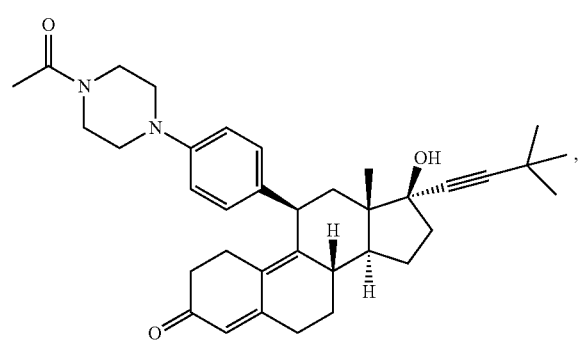
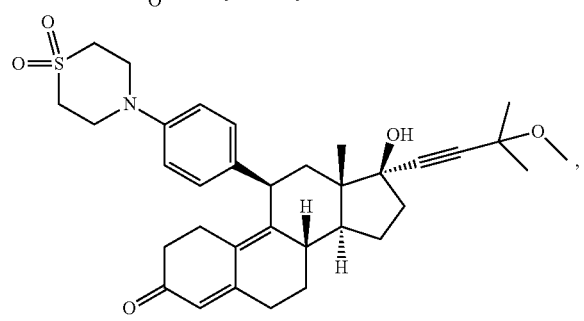
46
-continued
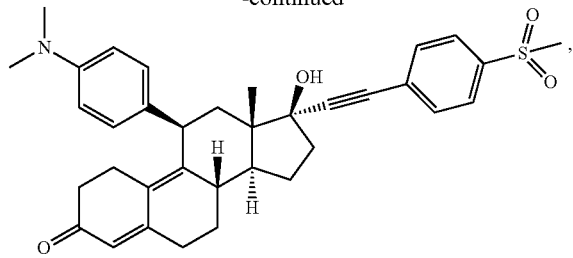
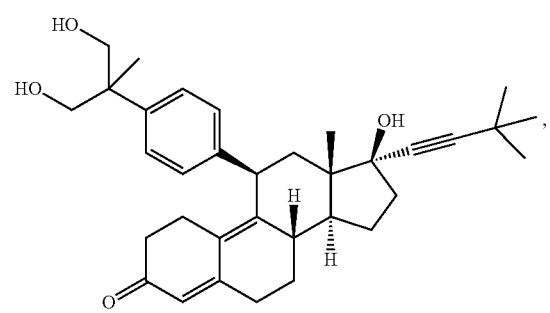
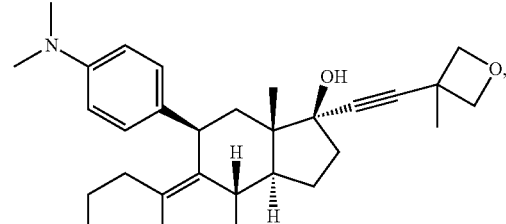
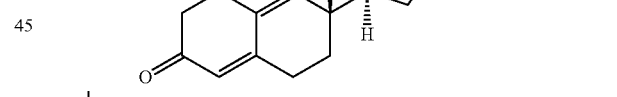
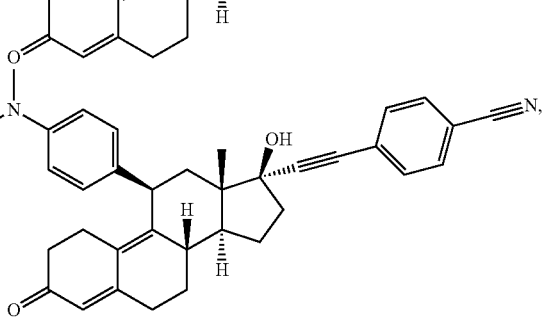

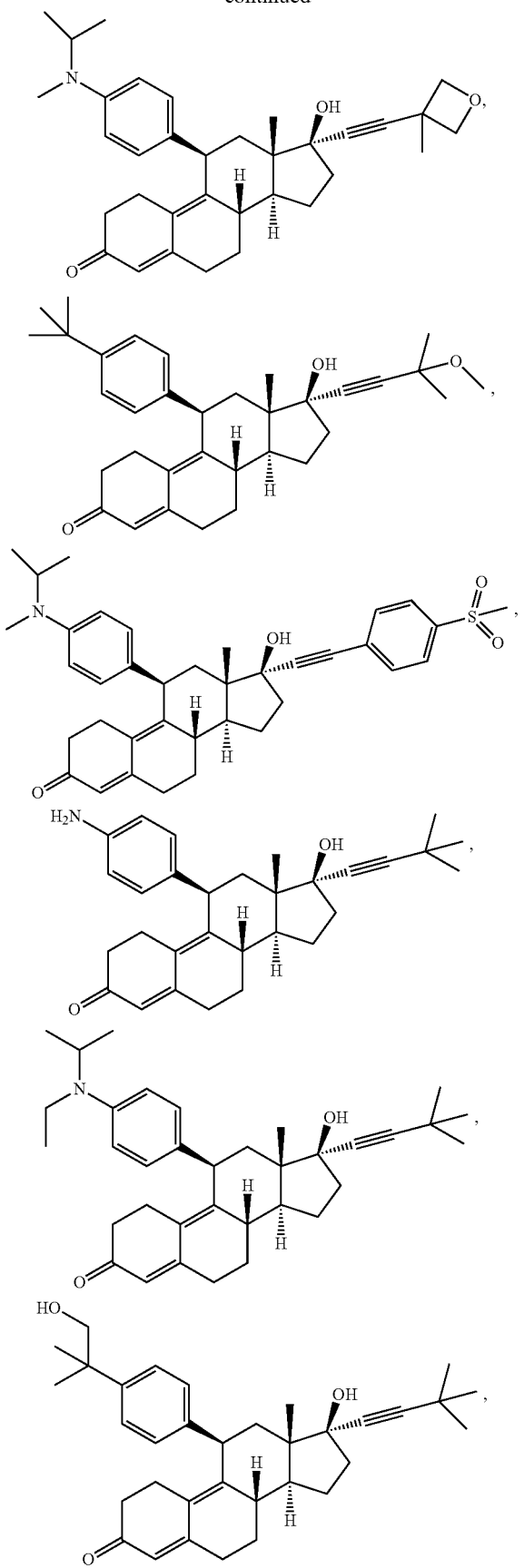
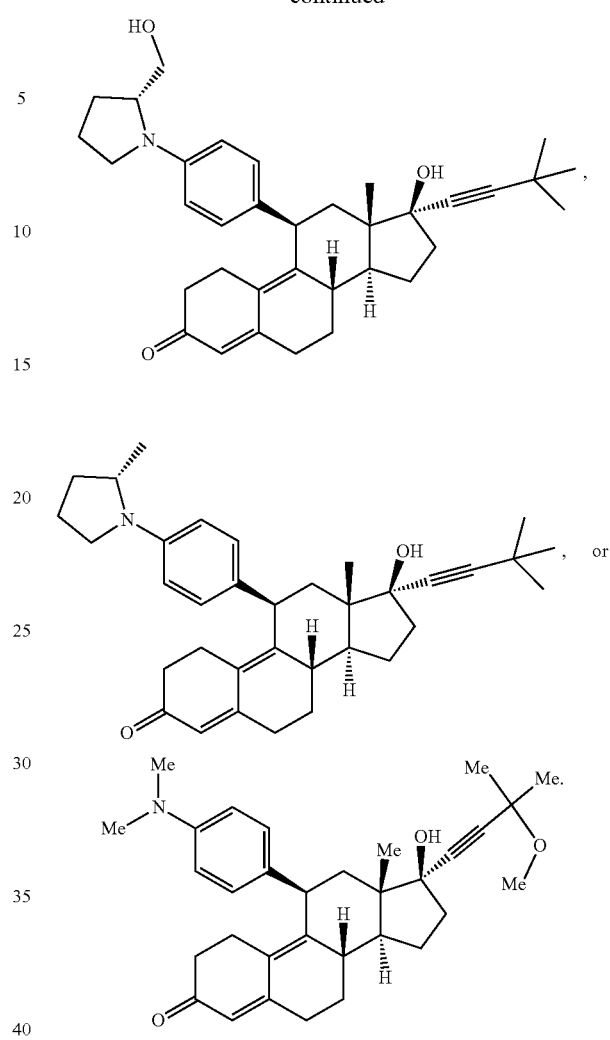
In some embodiments, a compound described herein has the structure of
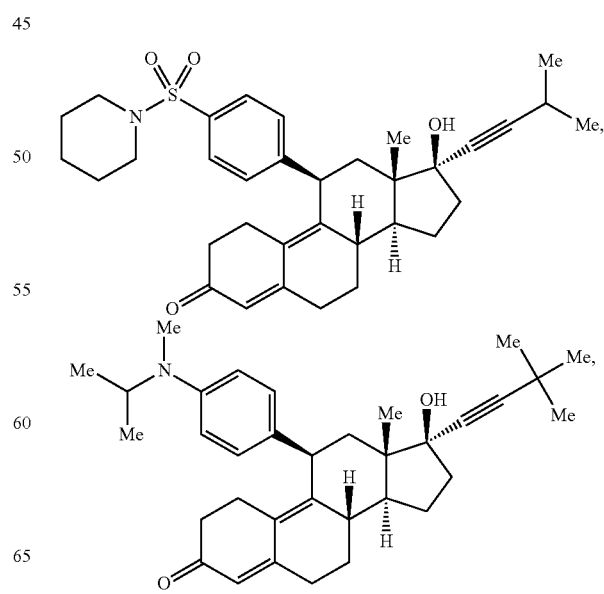

-continued
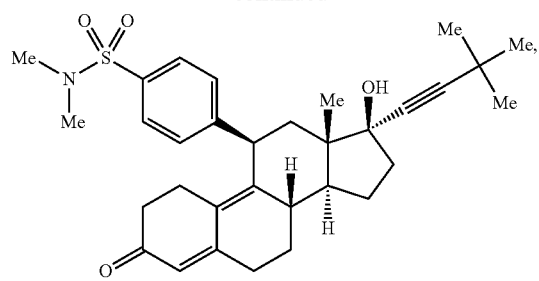
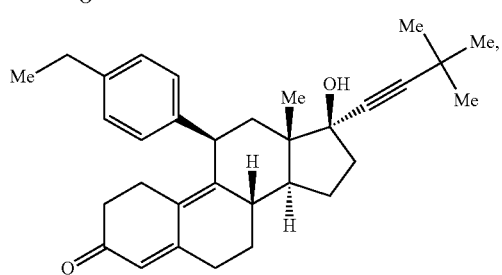
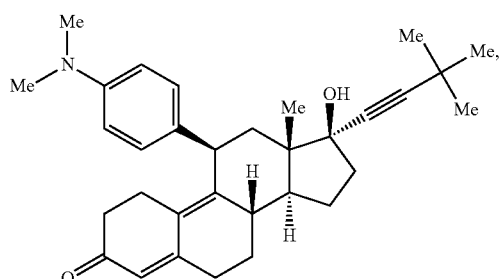
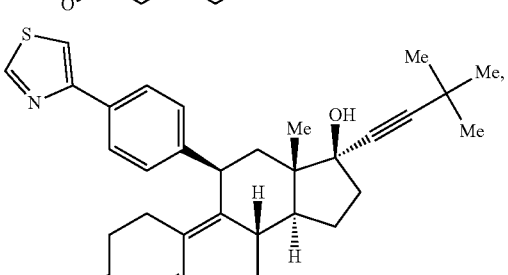
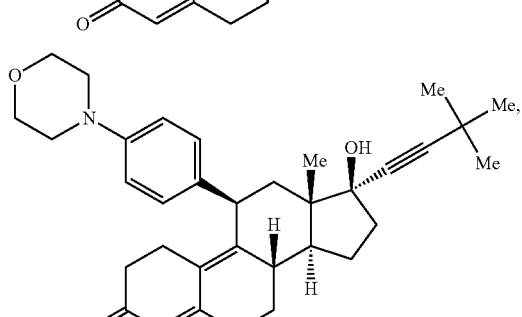
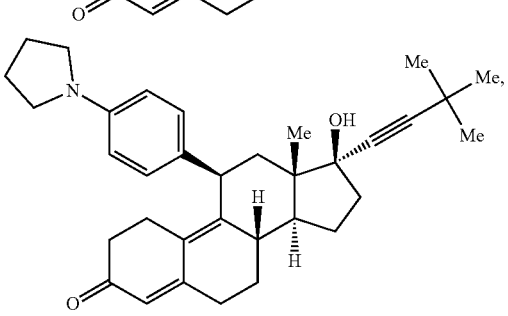
-continued
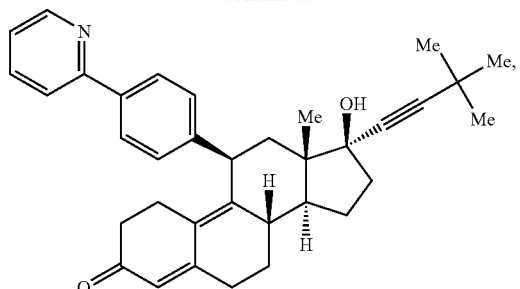
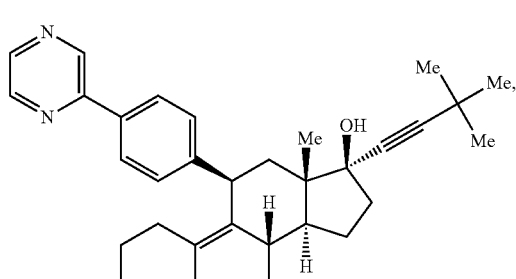
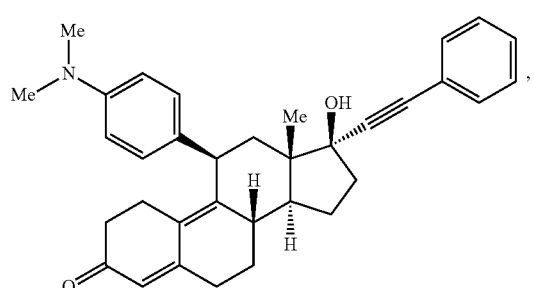
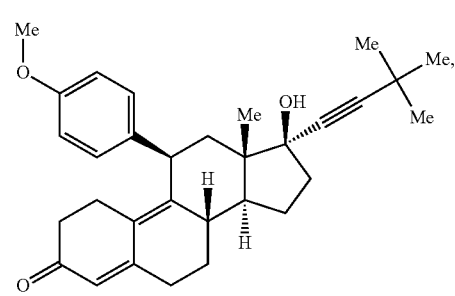
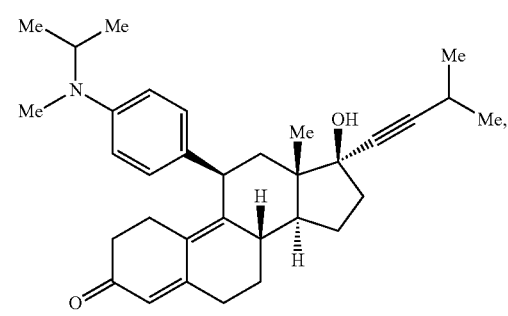

51
-continued
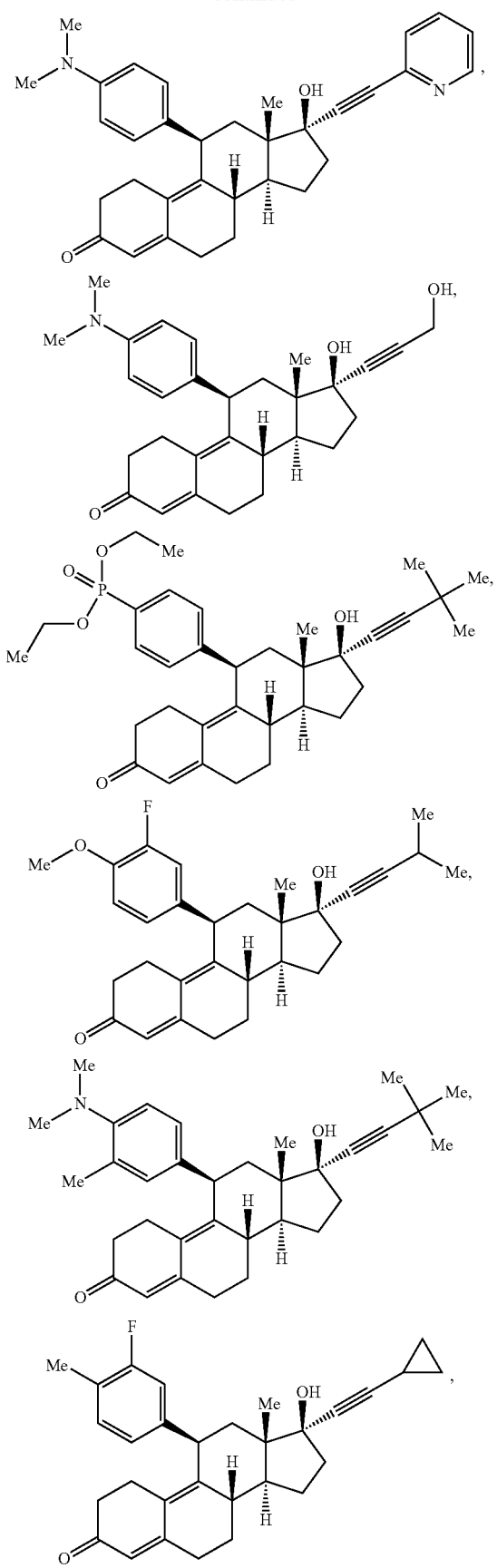
52
-continued
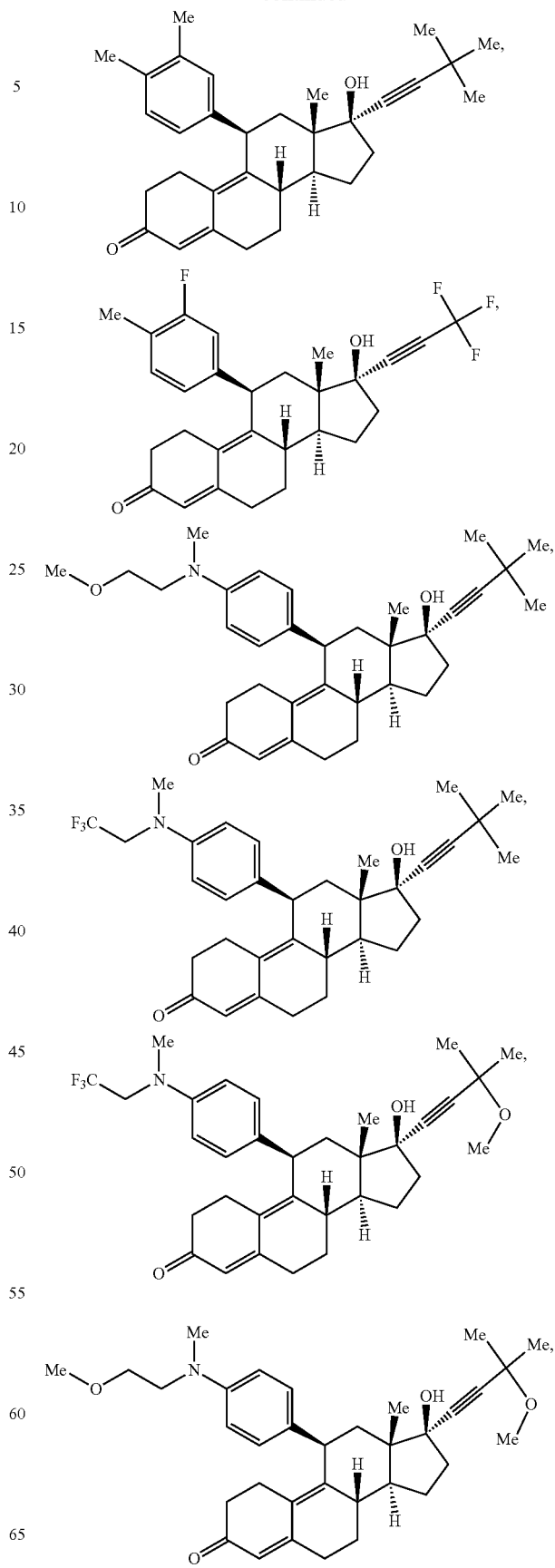

53
-continued
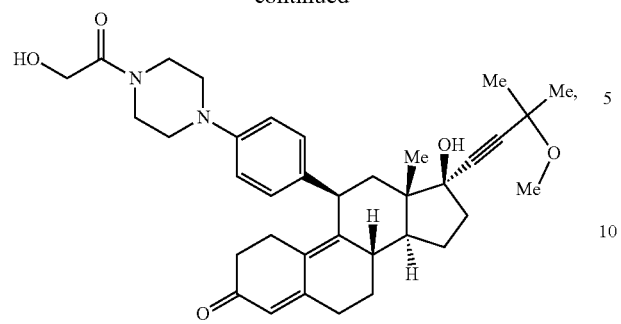
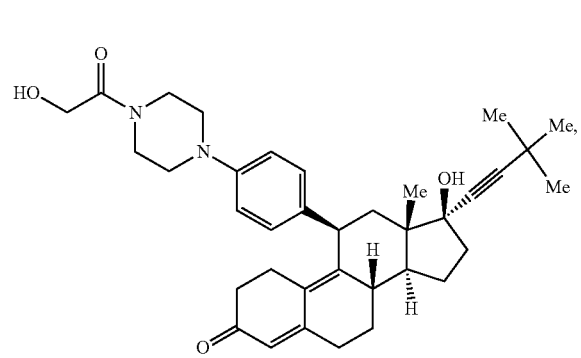
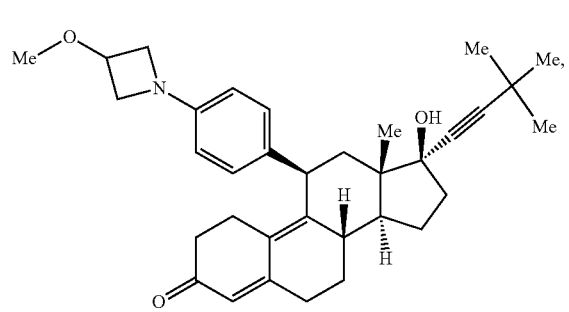
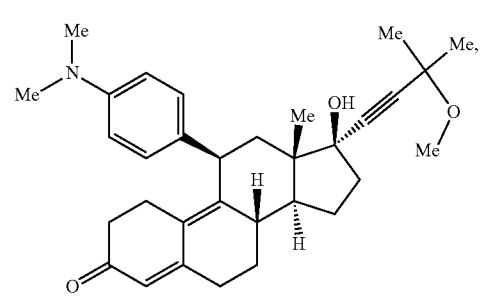
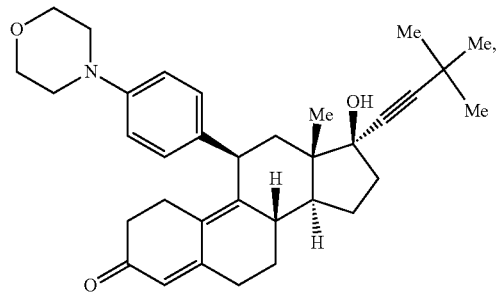
54
-continued
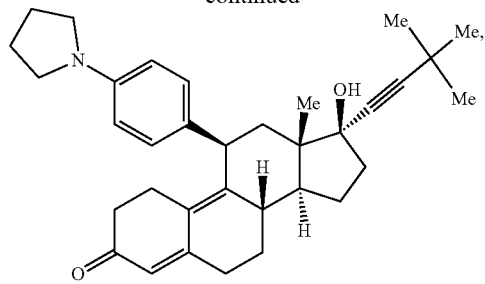
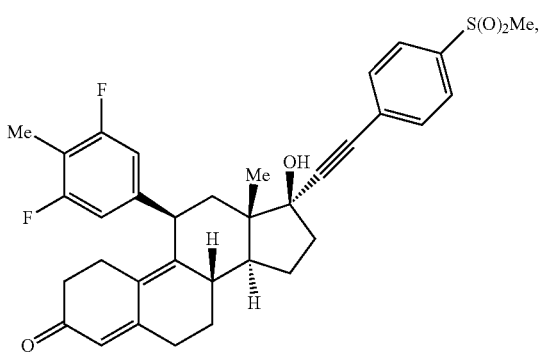
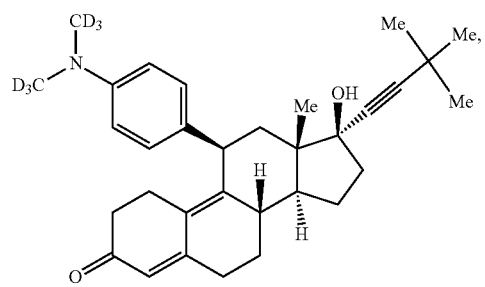
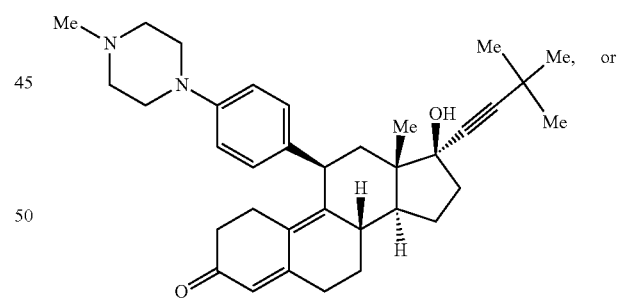
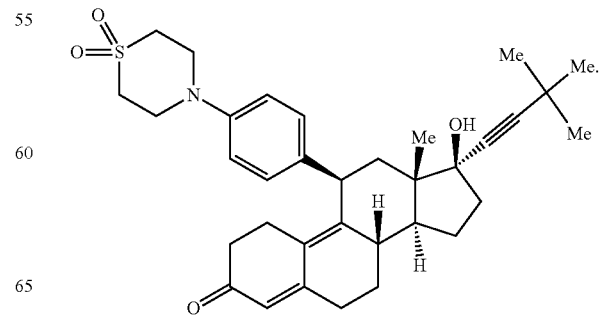

In some embodiments, a compound of formula (I) has the structure of

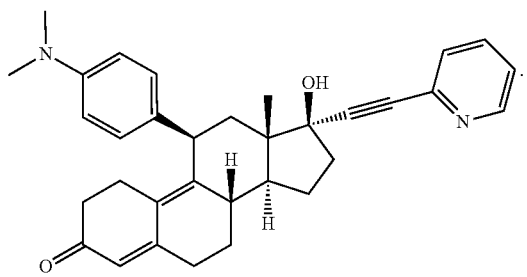

In some embodiments, a compound of formula (I) has the structure of

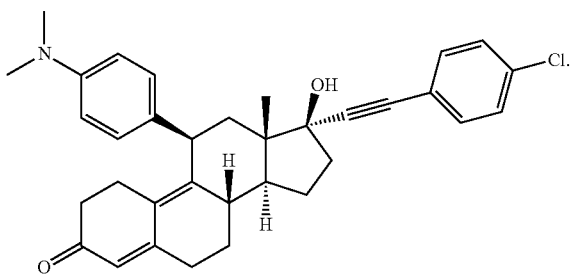

In some embodiments, a compound of formula (I) has the structure of

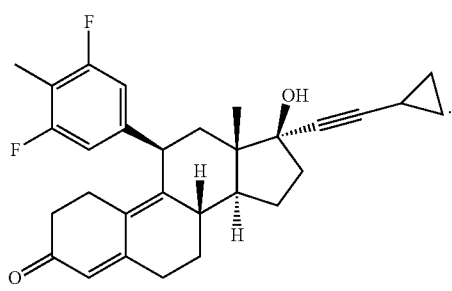

In some embodiments, a compound of formula (I) has the structure of

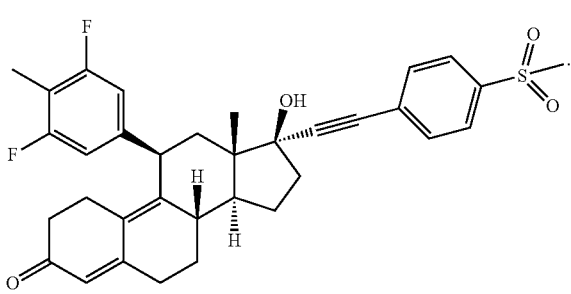

In some embodiments, a compound of formula (I) has the structure of

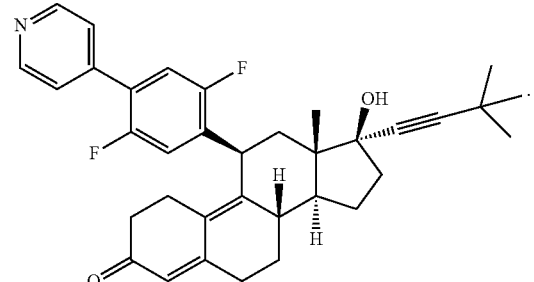

In some embodiments, a compound of formula (I) has the structure of

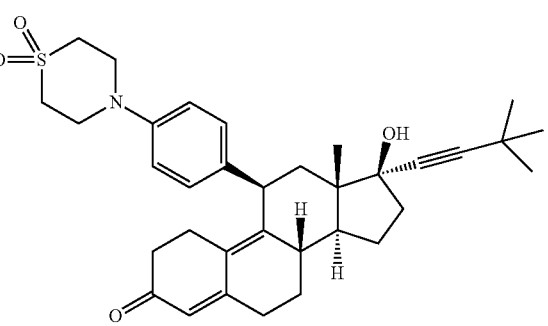

In some embodiments, a compound of formula (I) has the structure of

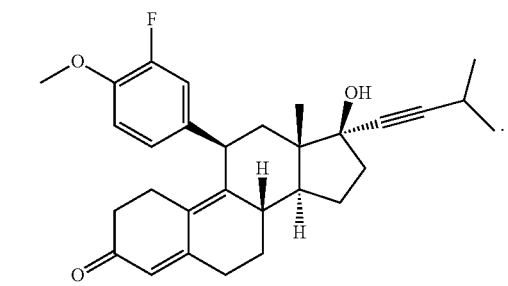

In some embodiments, a compound of formula (I) has the structure of

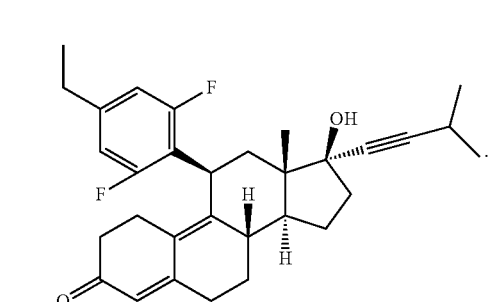

In some embodiments, a compound of formula (I) has the structure of

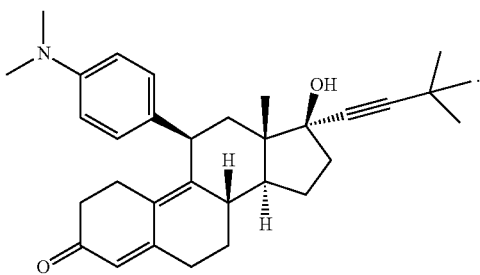

In some embodiments, a compound of formula (I) has the structure of

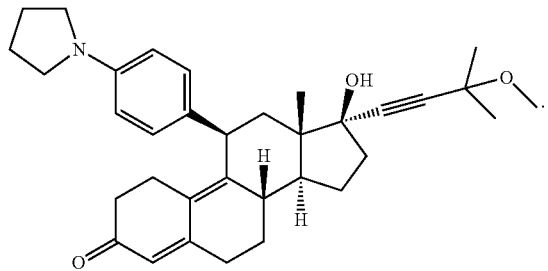

In some embodiments, a compound of formula (I) has the structure of

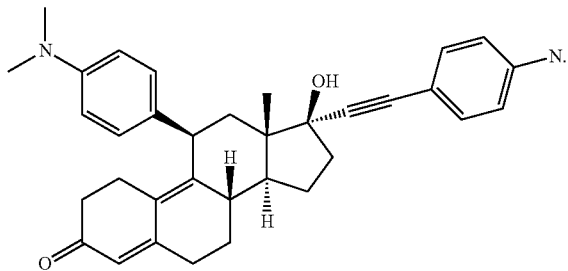

In some embodiments, a compound of formula (I) has the structure of

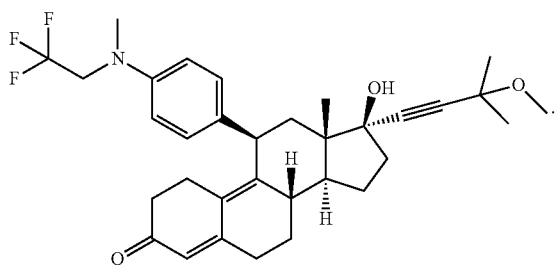

In some embodiments, a compound of formula (I) has the structure of

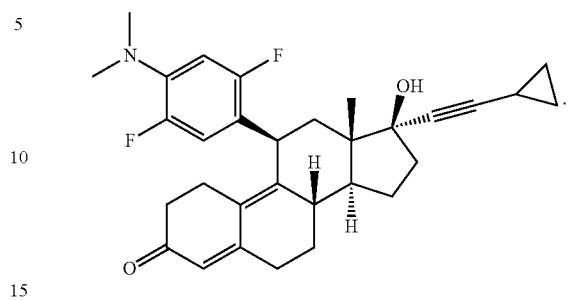

Some embodiments provided herein describe a compound having the structure of Formula (II), or a pharmaceutically acceptable salt or prodrug thereof:

Formula (II)

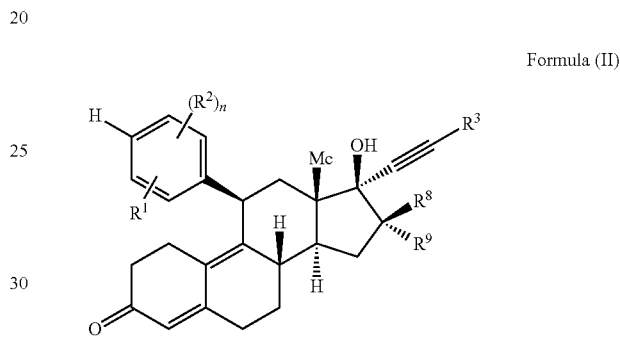

wherein $R^1$ is —$NR^4R^5$, optionally substituted alkyl$NR^4R^5$, halo, optionally substituted alkyl, haloalkyl, optionally substituted carbocyclyl, optionally substituted carbocyclylalkyl, optionally substituted alkylheteroalkyl, optionally substituted heterocyclyl, optionally substituted heterocyclylalkyl, optionally substituted hydroxyalkyl, optionally substituted aryl, optionally substituted heteroaryl, —C(O)$OR^6$, —C(O)$NR^4R^5$, —OC(O)$R^6$, —OC(O)$NR^4R^5$, —S(O)$_2NR^4R^5$, —S(O)$_2R^7$, —S(O)$R^7$, —$SR^7$, —$NR^4$S(O)$_2NR^4R^5$, —P(O)(O$R^6$)$_2$, —P(O)($R^6$)$_2$, —CN, —CO$_2$H, or —NO$_2$;

each $R^2$ is independently —$NR^4R^5$, optionally substituted alkyl$NR^4R^5$, halo, —O$R^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —C(O)$R^6$, —C(O)O$R^6$, —C(O)$NR^4R^5$, —OC(O)O$R^6$, —OC(O)$NR^4R^5$, —S(O)$_2NR^4R^5$, —S(O)$_2$R, —S(O)$R^7$, —$SR^7$, —$NR^4$S(O)$_2NR^4R^5$, —CN, —CO$_2$H, or —NO$_2$;

$R^3$ is optionally substituted $C_{2-10}$ alkyl, haloalkyl, halo, deuteroalkyl, optionally substituted carbocyclyl, optionally substituted carbocyclylalkyl, optionally substituted heterocyclyl, optionally substituted heterocyclylalkyl, optionally substituted aryl, optionally substituted heteroaryl, —Si($R^6$)$_3$, —O$R^6$, or —S(O)$_2R^7$;

$R^4$ and $R^5$ are each independently —H, optionally substituted alkyl, haloalkyl, optionally substituted carbocyclyl, optionally substituted aryl, optionally substituted heterocyclyl, optionally substituted heteroaryl, —S(O)$_2R^7$, —C(O)N($R^{10}$)$_2$, —C(O)$R^6$, or —C(O)O$R^6$;

or $R^4$ and $R^5$ attached to the same N atom are taken together with the N atom to which they are attached to form a substituted or unsubstituted heterocycle;

each $R^6$ is independently optionally substituted alkyl, haloalkyl, optionally substituted carbocyclyl, optionally substituted aryl, optionally substituted heterocyclyl, or optionally substituted heteroaryl;

$R^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

$R^8$ and $R^9$ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —$OR^6$, —$NR^4R^5$, —C(O)$NR^4R^5$, —CN, —S(O)$_2R^7$, —C(O)$_2$H, —C(O)$R^6$, or —C(O)$OR^6$;

or $R^8$ and $R^9$ are taken together with the atom to which they are attached to form a substituted or unsubstituted ring containing 0-2 heteroatoms selected from the group consisting of —O—, —NH—, —$NR^6$—, —S—, and —S(O)$_2$—;

each $R^{10}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl; and n is 0, 1, 2, or 3.

For any and all of the embodiments of Formula (II), substituents are selected from among a subset of the listed alternatives.

In some embodiments, $R^1$ is —$NR^4R^5$, optionally substituted alkyl$NR^4R^5$, halo, optionally substituted alkyl, fluoroalkyl, optionally substituted carbocyclyl, optionally substituted carbocyclylalkyl, optionally substituted heterocyclyl, optionally substituted heterocyclylalkyl, optionally substituted hydroxyalkyl, optionally substituted aryl, optionally substituted heteroaryl, —C(O)$N^4R^5$, —OC(O)$OR^6$, —OC(O)$N^4R^5$, —S(O)$_2NR^4R^5$, —S(O)$_2R^7$, —S(O)$R^7$, —$SR^7$, —$NR^4$S(O)$_2NR^4R^5$, —P(O)$(OR^6)_2$, —P(O)$(R^6)_2$, —CN, or —$NO_2$. In certain embodiments, $R^1$ is —$NR^4R^5$, optionally substituted alkyl$NR^4R^5$, halo, optionally substituted alkyl, fluoroalkyl, optionally substituted carbocyclyl, optionally substituted carbocyclylalkyl, optionally substituted heterocyclyl, optionally substituted heterocyclylalkyl, optionally substituted aryl, optionally substituted heteroaryl, —C(O)$NR^4R^5$, S(O)$_2NR^4R^5$, —S(O)$_2R^7$, —$NR^4$S(O)$_2NR^4R^5$, —P(O)$(OR^6)_2$, or —CN. In some embodiments, $R^1$ is —$NR^4R^5$, halo, —$OC_{3-10}$alkyl, optionally substituted alkyl, fluoroalkyl, optionally substituted carbocyclyl, optionally substituted heterocyclyl, optionally substituted aryl, optionally substituted heteroaryl, —C(O)$NR^4R^5$, —S(O)$_2NR^4R^5$, —S(O)$_2R^7$, —$NR^4$S(O)$_2NR^4R^5$, —P(O)$(R^6)_2$, —P(O)$(OR^6)_2$, or —CN. In some embodiments, $R^1$ is —$NR^4R^5$, halo, alkyl, fluoroalkyl, carbocyclyl, heterocyclyl, aryl, heteroaryl, —S(O)$_2NR^4R^5$, —S(O)$_2R^7$, —$NR^4$S(O)$_2NR^4R^5$, —P(O)$(OR^6)_2$, or —CN. In some embodiments, $R^1$ is —$NR^4R^5$, halo, —$OC_{3-10}$alkyl, $C_{1-6}$alkyl, $C_{1-6}$fluoroalkyl, $C_{3-6}$carbocyclyl, $C_{3-6}$heterocyclyl, aryl, heteroaryl, —C(O)$NR^4R^5$, —S(O)$_2NR^4R^5$, —S(O)$_2R^7$, —$NR^4$S(O)$_2NR^4R^5$, —P(O)$(R^6)_2$, —P(O)$(OR^6)_2$, or —CN. In some embodiments, $R^1$ is —$NR^4R^5$, halo, —$OR^6$, —S(O)$_2NR^4R^5$, —$NR^4$S(O)$_2NR^4R^5$, —P(O)$(R^6)_2$, or —P(O)$(OR^6)_2$. In certain embodiments, $R^1$ is —$NR^4R^5$, halo, —S(O)$_2NR^4R^5$, or —P(O)$(OR^6)_2$. In certain embodiments, $R^1$ is alkyl, fluoroalkyl, carbocyclyl, or heterocyclyl. In other embodiments, $R^1$ is —$NMe_2$, —NHMe, —$NH_2$, methyl, ethyl, propyl, iso-propyl, butyl, iso-butyl, sec-butyl, tert-butyl, propoxy, iso-propoxy, morpholino, or pyrrolidino. In certain embodiments, $R^1$ is $C_{1-6}$alkyl, fluoroalkyl, $C_{3-6}$carbocyclyl, or $C_{3-6}$heterocyclyl. In some embodiments, $R^1$ is —$NR^4R^5$. In some embodiments, $R^1$ is —$NMe_2$. In some embodiments, $R^1$ is —NHMe. In some embodiments, $R^1$ is —$NH_2$. In some embodiments, $R^1$ is —NMeEt. In some embodiments, $R^1$ is —$NEt_2$. In some embodiments, $R^1$ is halo. In some embodiments, $R^1$ is fluoro. In some embodiments, $R^1$ is chloro. In some embodiments, $R^1$ is bromo. In some embodiments, $R^1$ is $C_{1-6}$alkyl. In some embodiments, $R^1$ is methyl. In some embodiments, $R^1$ is ethyl. In some embodiments, $R^1$ is propyl. In some embodiments, $R^1$ is iso-propyl. In some embodiments, $R^1$ is carbocyclyl. In some embodiments, $R^1$ is cyclopropyl. In some embodiments, $R^1$ is cyclobutyl. In some embodiments, $R^1$ is cyclopentyl. In some embodiments, $R^1$ is cyclohexyl. In certain embodiments, $R^1$ is —$OR^6$. In certain embodiments, $R^1$ is methoxy. In some embodiments, $R^1$ is ethoxy. In some embodiments, $R^1$ is propoxy. In some embodiments, $R^1$ is iso-propoxy. In some embodiments, $R^1$ is heterocyclyl. In some embodiments, $R^1$ is azetadino, morpholino, thiomorpholino, piperidino, piperazino, or pyrrolidino. In some embodiments, $R^1$ is morpholino. In some embodiments, $R^1$ is pyrrolidino. In some embodiments, $R^1$ is azetadino.

In other embodiments, $R^1$ is optionally substituted monocyclic aryl, optionally substituted bicyclic aryl, optionally substituted monocyclic heteroaryl, or optionally substituted bicyclic heteroaryl. In certain embodiments, $R^1$ is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, $R^1$ is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, $R^1$ is pyrimidinyl, pyridinyl, pyrazinyl, triazinyl, or thiazolyl. In certain embodiments, $R^1$ is C-bound imidazolyl. In certain embodiments, $R^1$ is N-bound imidazolyl. In certain embodiments, $R^1$ is pyrimidinyl. In some embodiments, $R^1$ is pyrimidinyl optionally substituted with alkyl or alkoxy. In some embodiments, $R^1$ is pyrazinyl. In some embodiments, $R^1$ is triazinyl. In some embodiments, $R^1$ is thiazolyl.

In certain embodiments, $R^1$ is optionally substituted with halo, alkyl, hydroxy, alkoxy, or fluoroalkyl. In certain embodiments, $R^1$ is optionally substituted with halo, alkyl, or alkoxy. In some embodiments, $R^1$ is optionally substituted with fluoro or $C_{1-6}$alkyl. In some embodiments, $R^1$ is optionally substituted with fluoro or methyl. In some embodiments, $R^1$ is optionally substituted with methyl or methoxy.

In some embodiments, each $R^2$ is independently —$NR^4R^5$, optionally substituted alkyl$NR^4R^5$, halo, —$OR^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —C(O)$R^6$, —C(O)$NR^4R^5$, —S(O)$_2NR^4R^5$, —S(O)$_2R^7$, —$NR^4$S(O)$_2NR^4R^5$, or —CN. In some embodiments, each $R^2$ is independently —NR⁴R⁵, alkylNR⁴R⁵, halo, —OR⁶, —OH, alkyl, haloalkyl, carbocyclyl, carbocyclylalkyl, heteroalkyl, heterocyclyl, heterocyclylalkyl, hydroxyalkyl, —C(O)R⁶, —C(O)NR⁴R⁵, —S(O)₂NR⁴R⁵, —S(O)₂R⁷, —NR⁴S(O)₂NR⁴R⁵, or —CN. In certain embodiments, each R² is independently —NR⁴R⁵, halo, —OR⁶, —OH, optionally substituted alkyl, fluoroalkyl, optionally substituted carbocyclyl, optionally substituted heteroalkyl, optionally substituted heterocyclyl, optionally substituted hydroxyalkyl, —S(O)₂NR⁴R⁵, —S(O)₂R⁷, —NR⁴S(O)₂NR⁴R⁵, or —CN. In some embodiments, each R² is independently —NR⁴R⁵, $C_{1-6}$alkylNR⁴R⁵, halo, —OR⁶, —OH, $C_{1-6}$alkyl, $C_{1-6}$fluoroalkyl, $C_{3-6}$carbocyclyl, $C_{1-6}$alkyl$C_{3-6}$carbocyclyl, $C_{1-6}$heteroalkyl, $C_{3-6}$heterocyclyl, $C_{1-6}$alkyl$C_{3-6}$heterocyclyl, $C_{1-6}$hydroxyalkyl, or —CN. In some embodiments, each R² is independently —C(O)R⁶, —C(O)NR⁴R⁵, —S(O)₂NR⁴R⁵, —S(O)₂R⁷, —NR⁴S(O)₂NR⁴R⁵, or —CN. In some embodiments, each R² is independently —NR⁴R⁵, halo, —OR⁶, $C_{1-6}$alkyl, $C_{1-6}$fluoroalkyl, $C_{3-6}$carbocyclyl, $C_{1-6}$heteroalkyl, $C_{3-6}$heterocyclyl, or —CN. In some embodiments, each R² is independently —NR⁴R⁵, halo, alkyl, carbocyclyl, alkoxy, or —CN. In some embodiments, each R² is independently —NR⁴R⁵, halo, alkyl, or alkoxy. In some embodiments, each R² is independently methyl, methoxy, ethyl, propyl, iso-propyl, cyclopropyl, fluoro, chloro, or —NMe₂. In some embodiments, each R² is independently methyl, methoxy, iso-propyl, cyclopropyl, fluoro, chloro, or —NMe₂. In some embodiments, R² is methoxy. In some embodiments, R² is methyl. In some embodiments R² is ethyl. In some embodiments, R² is iso-propyl. In some embodiments, R² is propyl. In some embodiments, R² is cyclopropyl. In some embodiments, R² is cyclobutyl. In some embodiments, R² is fluoro. In some embodiments, R² is chloro. In some embodiments, R² is —NMe₂. In some embodiments, R² is —NH₂. In some embodiments, R² is —NHMe. In some embodiments, R² is —NMeEt. In some embodiments, n is 1, 2, or 3, and each R² is independently halo, optionally substituted alkyl, or haloalkyl. In some embodiments, n is 2, and each R² is independently fluoro, chloro, methyl, ethyl, propyl, or butyl. In some embodiments, n is 3, and each R² is independently fluoro, chloro, methyl, ethyl, propyl, or butyl.

In certain embodiments, each R² is independently optionally substituted with halo, alkyl, hydroxy, alkoxy, or fluoroalkyl. In some embodiments, each R² is independently optionally substituted with fluoro or $C_{1-6}$alkyl. In some embodiments, each R² is independently optionally substituted with fluoro or methyl.

In some embodiments, R³ is $C_{2-10}$ alkyl, haloalkyl, halo, deuteroalkyl, carbocyclyl, carbocyclylalkyl, heterocyclyl, heterocyclylalkyl, aryl, heteroaryl, —Si(R⁶)₃, —OR⁶, or —S(O)₂R⁷. In some embodiments, R³ is optionally substituted $C_{2-10}$ alkyl, haloalkyl, halo, deuteroalkyl, carbocyclyl, optionally substituted aryl, optionally substituted heteroaryl, —Si(R⁶)₃, —OR⁶, or —S(O)₂R⁷, wherein R³ is optionally substituted with halo, alkyl, alkoxy, hydroxy, —NR⁴R⁵, or —S(O)₂R⁷. In some embodiments, R³ is $C_{3-6}$ alkyl, $C_{1-6}$ haloalkyl, halo, $C_{1-6}$ deuteroalkyl, $C_{3-6}$ carbocyclyl, $C_{3-6}$ carbocyclyl$C_{1-6}$ alkyl, $C_{3-6}$heterocyclyl, $C_{3-6}$ heterocyclyl$C_{1-6}$ alkyl. In some embodiments, R³ is $C_{2-6}$ alkyl, $C_{1-6}$ fluoroalkyl, halo, carbocyclyl, or heterocyclylalkyl. In some embodiments, R³ is $C_{2-6}$ alkyl. In some embodiments, R³ is $C_{3-6}$ alkyl. In some embodiments, R³ is i-propyl. In some embodiments, R³ is t-butyl. In some embodiments, R³ is butyl. In some embodiments, R³ is isobutyl. In some embodiments, R³ is sec-butyl. In some embodiments, R³ is carbocyclyl. In some embodiments, R³ is cyclopropyl. In some embodiments, R³ is cyclobutyl. In some embodiments, R³ is cyclopentyl. In some embodiments, R³ is cyclohexyl. In some embodiments, R³ is halo. In some embodiments, R³ is fluoro. In some embodiments, R³ is chloro. In some embodiments, R³ is bromo. In some embodiments, R³ is trifluoromethyl. In some embodiments, R³ is hydroxyalkyl. In some embodiments, R³ is deuteromethyl. In some embodiments, R³ is —Si(R⁶)₃. In some embodiments, R³ is —Si(Me)₃. In some embodiments, R³ is —Si(Ph)₃. In some embodiments, R³ is —OR⁶. In some embodiments, R³ is —S(O)₂R⁷.

In other embodiments, R³ is optionally substituted aryl or optionally substituted heteroaryl. In certain specific embodiments, R³ is phenyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments, R³ is phenyl optionally substituted with halo, alkyl, alkoxy, hydroxy, —NR⁴R⁵, or —S(O)₂R⁷. In some embodiments, R³ is pyridinyl optionally substituted with halo, alkyl, alkoxy, hydroxy, —NR⁴R⁵, or —S(O)₂R⁷. In some embodiments, R³ is phenyl. In some embodiments, R³ is pyridinyl. In some embodiments, R³ is $C_1$ deuteroalkyl, $C_2$ deuteroalkyl, $C_3$ deuteroalkyl, $C_4$ deuteroalkyl, or $C_5$ deuteroalkyl. In some embodiments, R³ is $C_1$ monodeuteroalkyl, $C_1$ dideuteroalkyl, or $C_1$ trideuteroalkyl. In some embodiments, R³ is substituted $C_{2-10}$ alkyl, wherein substituents are selected from halo, alkyl, hydroxy, alkoxy, chloroalkyl, or fluoroalkyl.

In certain embodiments, R³ is optionally substituted with halo, alkyl, hydroxy, alkoxy, —NR⁴R⁵, —S(O)₂R⁷ or fluoroalkyl. In some embodiments, R³ is optionally substituted with chloro, fluoro, methyl, ethyl, propyl, iso-propyl, butyl, iso-butyl, sec-butyl, tert-butyl, hydroxy, methoxy, ethoxy, propoxy, iso-propoxy, cyano, dimethylamino, diethylamino, methylamino, amino, —S(O)₂Me, or trifluoromethyl. In certain embodiments, R³ is optionally substituted with chloro, fluoro, methyl, hydroxy, methoxy, cyano, dimethylamino, —S(O)₂Me, or trifluoromethyl. In certain embodiments, R³ is phenyl substituted with chloro, fluoro, methyl, ethyl, propyl, butyl, hydroxy, methoxy, cyano, —S(O)₂Me, or trifluoromethyl. In some embodiments, R³ is phenyl substituted with methyl, ethyl, propyl, t-butyl, cyano, —S(O)₂Me, or trifluoromethyl. In certain embodiments, R³ is pyridyl substituted with chloro, fluoro, methyl, ethyl, propyl, butyl, hydroxy, methoxy, cyano, —S(O)₂Me, or trifluoromethyl. In some embodiments, R³ is pyridyl substituted with methyl, ethyl, propyl, t-butyl, cyano, —S(O)₂Me, or trifluoromethyl.

In some embodiments, R³ is optionally substituted heterocyclyl, wherein the heterocyclyl is

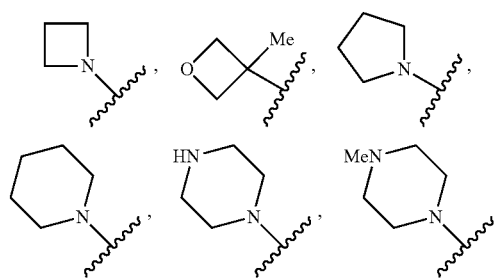

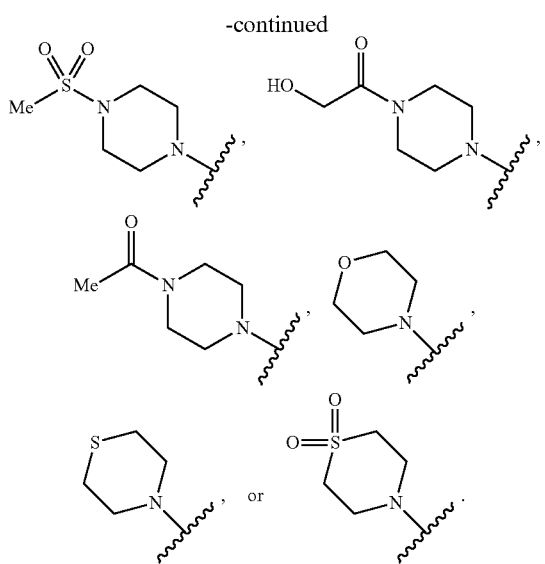

In some embodiments, R³ is heterocyclyl, wherein the heterocyclyl is

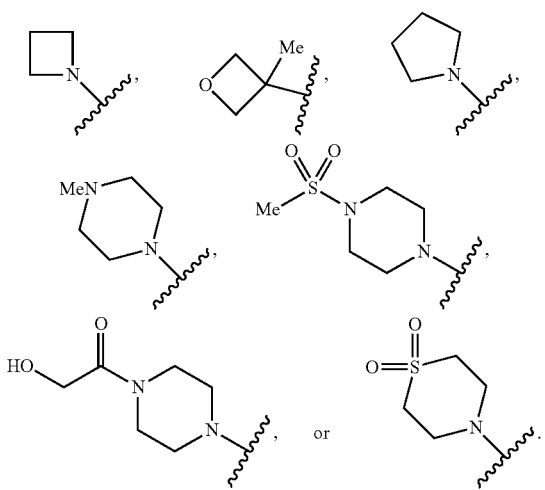

In some embodiments, R⁴ and R⁵ are each independently —H, optionally substituted alkyl, fluoroalkyl, optionally substituted carbocyclyl, optionally substituted carbocyclylalkyl, optionally substituted heterocyclyl, optionally substituted heterocyclylalkyl, —S(O)₂R⁷, or —C(O)N(R¹⁰)₂. In some embodiments, R⁴ and R⁵ are each independently —H, $C_{1-6}$ alkyl, $C_{1-6}$ fluoroalkyl, $C_{3-6}$ carbocyclyl, $C_{1-6}$ carbocyclylalkyl, $C_{2-6}$ heterocyclyl, $C_{1-6}$ alkyl$C_{3-6}$heterocyclyl, —S(O)₂R⁷, or —C(O)N(R¹⁰)₂. In some embodiments, R⁴ and R⁵ are each independently —H, $C_{1-6}$alkyl, $C_{1-6}$fluoroalkyl, $C_{3-6}$carbocyclyl, $C_{3-5}$heterocyclyl, or —S(O)₂R⁷. In some embodiments, R⁴ and R⁵ are each independently —H, $C_{1-6}$alkyl, or —S(O)₂R⁷. In some embodiments, R⁴ and R⁵ are each independently —H, methyl, ethyl, propyl, isopropyl, butyl, sec-butyl, iso-butyl, tert-butyl, or —S(O)₂R⁷. In some embodiments, R⁴ is methyl. In some embodiments, R⁴ is ethyl. In some embodiments, R⁴ is propyl. In some embodiments, R⁵ is methyl, ethyl, or propyl. In some embodiments, R⁴ is —C(O)N(R¹⁰)₂. In some embodiments, R⁴ is $C_{1-6}$alkyl$C_{3-6}$heterocyclyl. In some embodiments, R⁴ is —S(O)₂R⁷. In some embodiments, R⁴ and R⁵ are —H. In some embodiments, R⁴ and R⁵ are methyl. In some embodiments, R⁴ and R⁵ are each independently —H or —C(O)N(R¹⁰)₂.

In some embodiments, R⁴ and R⁵ are each independently $C_{1-6}$alkyl, optionally substituted with substituents selected from halo, alkyl, hydroxy, alkoxy, chloroalkyl, or fluoroalkyl. In some embodiments, R⁴ and R⁵ are each independently substituted with chloro, fluoro, cyano, methoxy, ethoxy, propoxy, chloroalkyl, or fluoroalkyl.

In other embodiments, R⁴ and R⁵ attached to the same N atom are taken together with the N atom to which they are attached to form a substituted or unsubstituted 4-, 5-, or 6-membered ring heterocycle additionally containing 0-3 heteroatoms selected from —O—, —NH—, —NR⁶—, —S—, and —S(O)₂—. In some embodiments, R⁴ and R⁵ attached to the same N atom are taken together with the N atom to which they are attached to form a 4-, 5- or 6-membered heterocycle additionally containing 0 or 1 oxygen heteroatom. In other embodiments, R⁴ and R⁵ attached to the same N atom are taken together with the N atom to which they are attached to form a substituted or unsubstituted 4-, 5-, or 6-membered ring heterocycle additionally containing 1 heteroatoms selected from —O—, —NH—, —NR⁶—, —S—, and —S(O)₂—. In other embodiments, R⁴ and R⁵ attached to the same N atom are taken together with the N atom to which they are attached to form a 4-, 5-, or 6-membered ring heterocycle additionally containing 1 oxygen heteroatom. In other embodiments, R⁴ and R⁵ attached to the same N atom are taken together with the N atom to which they are attached to form a substituted or unsubstituted 4-, 5-, or 6-membered ring. In some embodiments, the substituted or unsubstituted 4-, 5-, or 6-membered ring is

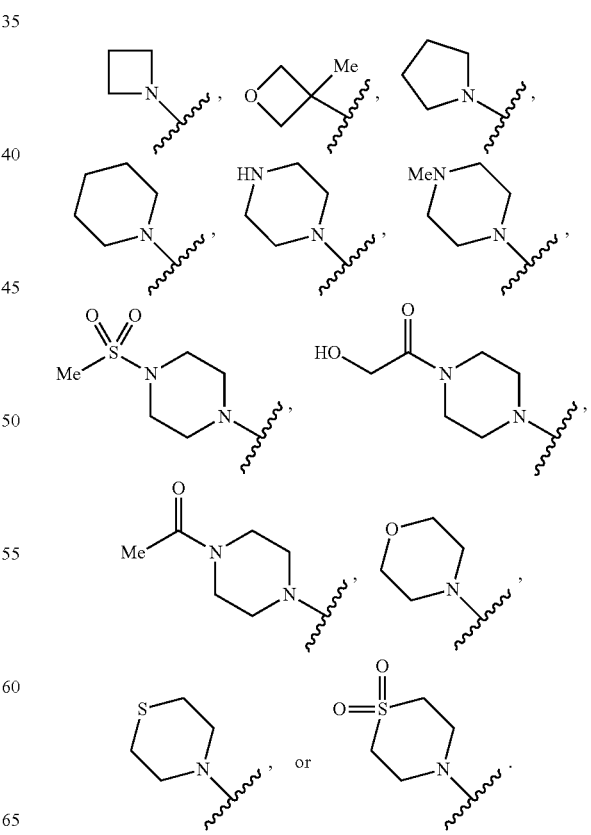

In some embodiments, 5-membered ring is

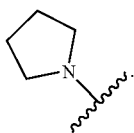 [SMILES: *N1CCCC1]

In some embodiments, the 6-membered ring is

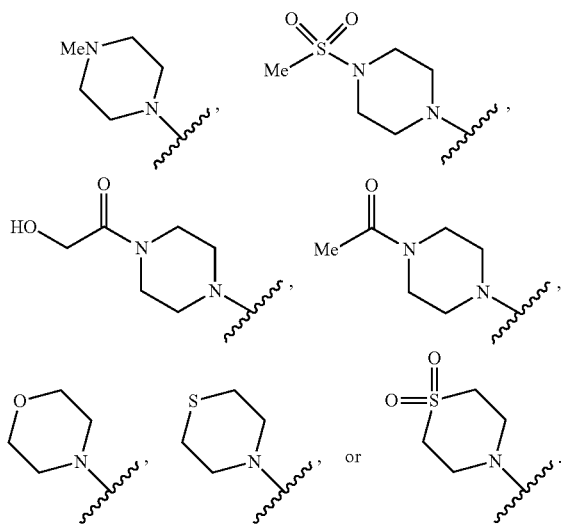

In other embodiments, $R^4$ and $R^5$ attached to the same N atom are taken together with the N atom to which they are attached to form a substituted 4-, 5-, or 6-membered ring, wherein the substituents are selected from halo, alkyl, hydroxy, alkoxy, chloroalkyl, or fluoroalkyl. In some embodiments, the heterocycle is substituted with chloro, fluoro, cyano, methoxy, ethoxy, chloroalkyl, or fluoroalkyl.

In certain embodiments, $R^4$ and $R^5$ are each independently optionally substituted with halo, alkyl, hydroxy, alkoxy, or fluoroalkyl. In some embodiments, $R^4$ and $R^5$ are each independently optionally substituted with fluoro or $C_{1-6}$alkyl. In some embodiments, $R^4$ and $R^5$ are each independently optionally substituted with fluoro or methyl.

In some embodiments, $R^6$ is optionally substituted alkyl, fluoroalkyl, optionally substituted aryl, optionally substituted carbocyclyl, or optionally substituted heterocyclyl. In some embodiments, $R^6$ is optionally substituted alkyl, fluoroalkyl, optionally substituted carbocyclyl, or optionally substituted heterocyclyl. In some embodiments, $R^6$ is alkyl, carbocyclyl, or heterocyclyl. In some embodiments, $R^6$ is alkyl, aryl, carbocyclyl, or heterocyclyl. In some embodiments, $R^6$ is alkyl, carbocyclyl, or fluoroalkyl. In some embodiments, $R^6$ is $C_{1-6}$alkyl, $C_{1-6}$fluoroalkyl, $C_{3-6}$carbocyclyl, or $C_{3-6}$heterocyclyl. In certain embodiments, $R^6$ is $C_{1-6}$alkyl. In certain embodiments, $R^6$ is methyl, ethyl, propyl, iso-propyl, butyl, sec-butyl, iso-butyl, or tert-butyl. In some embodiments, $R^6$ is optionally substituted phenyl.

In some embodiments, $R^7$ is alkyl, carbocyclyl, optionally substituted aryl, optionally substituted aralkyl, or optionally substituted heterocyclyl. In some embodiments, $R^7$ is $C_{1-6}$alkyl, $C_{3-6}$carbocyclyl, or aryl optionally substituted with halo or alkyl. In some embodiments, $R^7$ is $C_{1-6}$alkyl, $C_{3-6}$carbocyclyl, or phenyl optionally substituted with halo or alkyl. In some embodiments, $R^7$ is optionally substituted benzyl. In some embodiments, $R^7$ is $C_{3-6}$carbocyclyl. In some embodiments, $R^7$ is phenyl. In some embodiments, $R^7$ is phenyl substituted with 1-4 $C_{1-6}$alkyl or fluoro substituents. In some embodiments, $R^7$ is phenyl substituted with a $C_{1-6}$alkyl or fluoro substituent. In some embodiments, $R^7$ is alkyl, carbocyclyl, aralkyl, or heterocyclyl.

In certain embodiments, $R^7$ is optionally substituted with halo, alkyl, hydroxy, alkoxy, or fluoroalkyl. In some embodiments, $R^7$ is optionally substituted with fluoro or $C_{1-6}$alkyl. In some embodiments, $R^7$ is optionally substituted with fluoro or methyl.

In some embodiments, $R^8$ and $R^9$ are each independently —H, $C_{1-6}$alkyl, $C_{1-6}$haloalkyl, halo, $C_{3-6}$carbocyclyl, $C_{1-6}$alkyl$C_{3-6}$carbocyclyl, $C_{1-6}$heteroalkyl, $C_{3-6}$heterocyclyl, $C_{1-6}$alkyl$C_{3-6}$heterocyclyl, —OH, $OR^6$, —$NR^4R^5$, —$C(O)NR^4R^5$, —CN, —$S(O)_2R^7$, —$C(O)_2H$, —$C(O)R^6$, or —$C(O)OR^6$ or $R^8$ and $R^9$ are taken together with the atom to which they are attached to form a ring containing 0-2 heteroatoms selected from the group consisting of —O—, —$NR^6$—, —S—, and —$S(O)_2$—. In some embodiments, $R^8$ and $R^9$ are each independently —H, $C_{1-6}$alkyl, or $C_{3-6}$carbocyclyl, methoxy, ethoxy, propoxy, iso-propoxy, —$NH_2$, —$NMe_2$, —NHMe, —$NEt_2$, —$C(O)NH_2$, —$C(O)NMe_2$, —$C(O)NHMe$, or —CN. In some embodiments, $R^8$ and $R^9$ are each independently —H, $C_{1-6}$alkyl, $C_{1-6}$fluoroalkyl, halo or $C_{3-6}$carbocyclyl. In some embodiments, $R^8$ and $R^9$ are each independently —H, $C_{1-6}$alkyl, or $C_{3-6}$carbocyclyl. In some embodiments, $R^8$ is —H and $R^9$ is $C_{1-6}$alkyl, $C_{1-6}$fluoroalkyl, halo, or $C_{3-6}$carbocyclyl. In some embodiments, $R^8$ is —H and $R^9$ is alkyl. In some embodiments, $R^8$ is $C_{1-6}$alkyl, $C_{1-6}$fluoroalkyl, halo, or $C_{3-6}$carbocyclyl and $R^9$ is —H. In some embodiments, $R^8$ is methyl and $R^9$ is —H. In some embodiments, $R^8$ and $R^9$ are —H. In some embodiments, $R^8$ and $R^9$ are $C_{1-6}$alkyl. In some embodiments, $R^8$ and $R^9$ are methyl.

In other embodiments, $R^8$ and $R^9$ are taken together with the atom to which they are attached to form a 3-, 4-, 5-, or 6-membered ring containing 0-2 heteroatoms selected from the group consisting of —O—, —NH—, —$NR^6$—, —S—, and —$S(O)_2$—. In some embodiments, $R^8$ and $R^9$ are taken together with the atom to which they are attached to form a 3-, 4-, 5-, or 6-membered carbocyclic ring.

In some embodiments, each $R^{10}$ is independently hydrogen, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl. In some embodiments, each $R^{10}$ is independently hydrogen, optionally substituted alkyl, optionally substituted carbocyclyl, optionally substituted heteroalkyl, or optionally substituted aryl. In some embodiments, each $R^{10}$ is independently optionally substituted alkyl, optionally substituted carbocyclyl, optionally substituted heteroalkyl, optionally substituted aryl, or heteroaryl. In some embodiments, each $R^{10}$ is independently alkyl or aryl. In some embodiments, each $R^{10}$ is independently hydrogen or $C_{1-6}$ alkyl. In some embodiments, each $R^{10}$ is independently hydrogen, methyl, ethyl, propyl, iso-propyl, butyl, iso-butyl, sec-butyl, tert-butyl, pentyl or hexyl. In some embodiments, each $R^1$ is independently hydrogen, methyl, ethyl, propyl, iso-propyl, butyl, or tert-butyl. In some embodiments, each $R^{10}$ is independently hydrogen or methyl. In some embodiments, $R^{10}$ is H. In other embodiments, $R^{10}$ is alkyl. In other embodiments, $R^{10}$ is methyl. In some embodiments, $R^{10}$ is ethyl. In other embodiments, $R^{10}$ is propyl. In other embodiments, $R^{10}$ is substituted alkyl. In some embodiments, $R^{10}$ is methyl substituted with halo, —OH, or —CN. In some embodiments, $R^{10}$ is ethyl substituted with halo, —OH, or —CN. In some embodiments, $R^{10}$ is propyl substituted with halo, —OH, or —CN. In other embodiments, $R^{10}$ is aryl.

In some embodiments, n is 0, 1, or 2. In some embodiments, n is 0. In some embodiments, n is 1 or 2. In some embodiments, n is 1. In some embodiments, n is 2. In some embodiments, n is 3.

In some embodiments, compounds described herein have the following structure of Formula (IIa):

Formula (IIa)

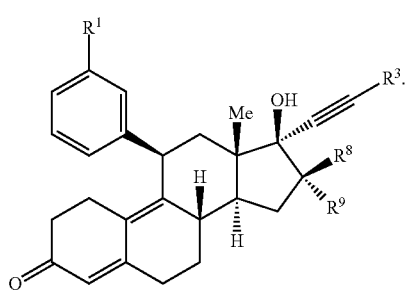

In some embodiments, compounds described herein have the following structure of Formula (IIb):

Formula (IIb)

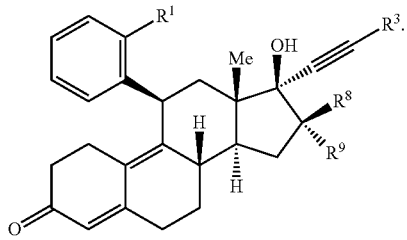

In some embodiments, compounds described herein have the following structure of Formula (IIc):

Formula (IIc)

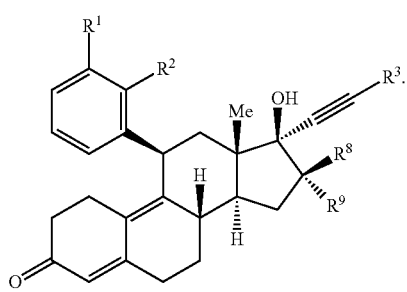

In some embodiments, compounds described herein have the following structure of Formula (IId):

Formula (IId)

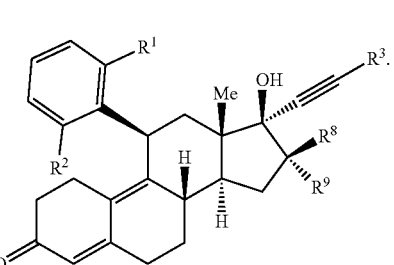

In some embodiments, compounds described herein have the following structure of Formula (IIe):

Formula (IIe)

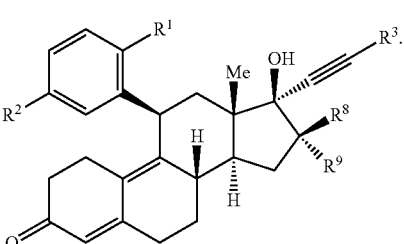

In some embodiments, compounds described herein have the following structure of Formula (IIf):

Formula (IIf)

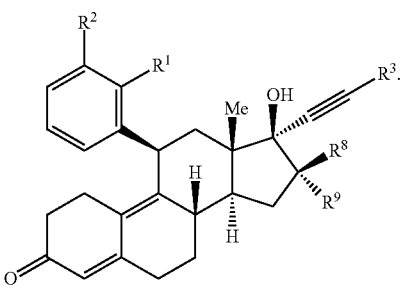

In some embodiments, compounds described herein have the following structure of Formula (IIg):

Formula (IIg)

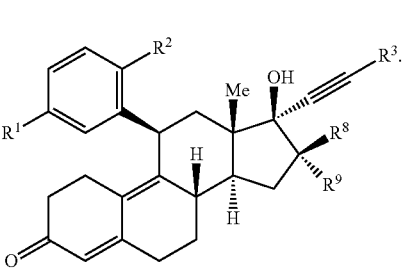

In some embodiments, compounds described herein have the following structure of Formula (IIh):

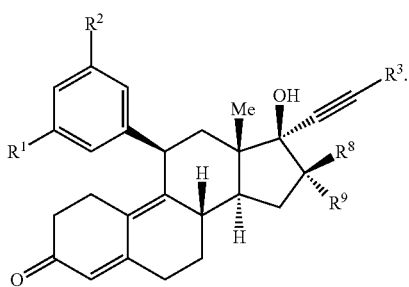

Formula (IIh)

In some embodiments, compounds described herein have the following structure of Formula (IIi):

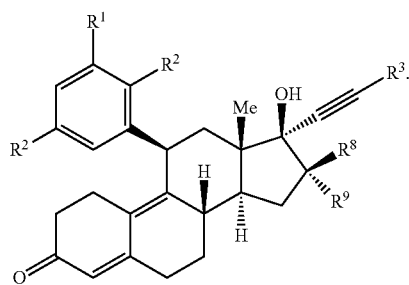

Formula (IIi)

In some embodiments, compounds described herein have the following structure of Formula (IIj):

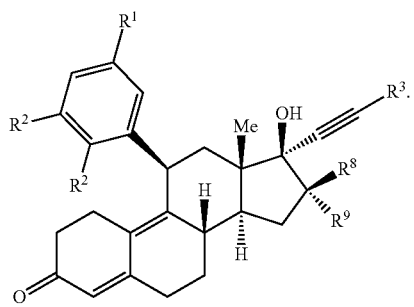

Formula (IIj)

In some embodiments, compounds described herein have the following structure of Formula (IIk):

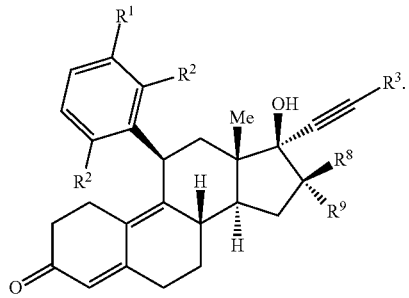

Formula (IIk)

In some embodiments, compounds described herein have the following structure of Formula (IIm):

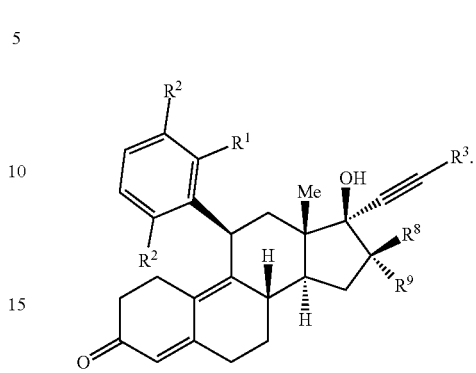

Formula (IIm)

In some embodiments, compounds described herein have the following structure of Formula (IIn):

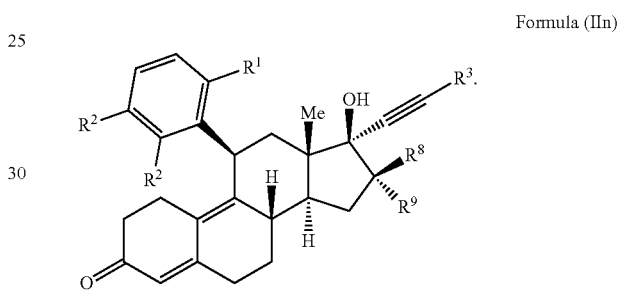

Formula (IIn)

In some embodiments, compounds described herein have the following structure of Formula (IIo):

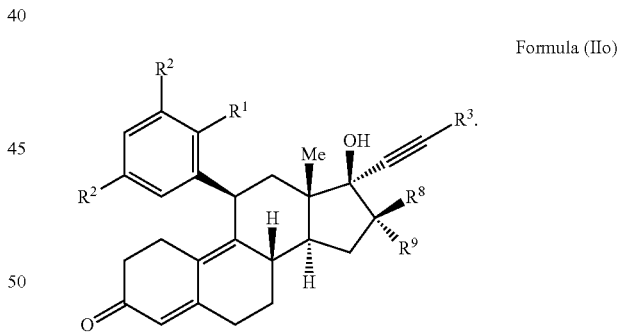

Formula (IIo)

Some embodiments provided herein describe a compound having the structure:

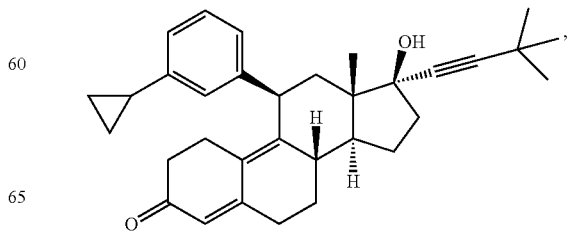

-continued
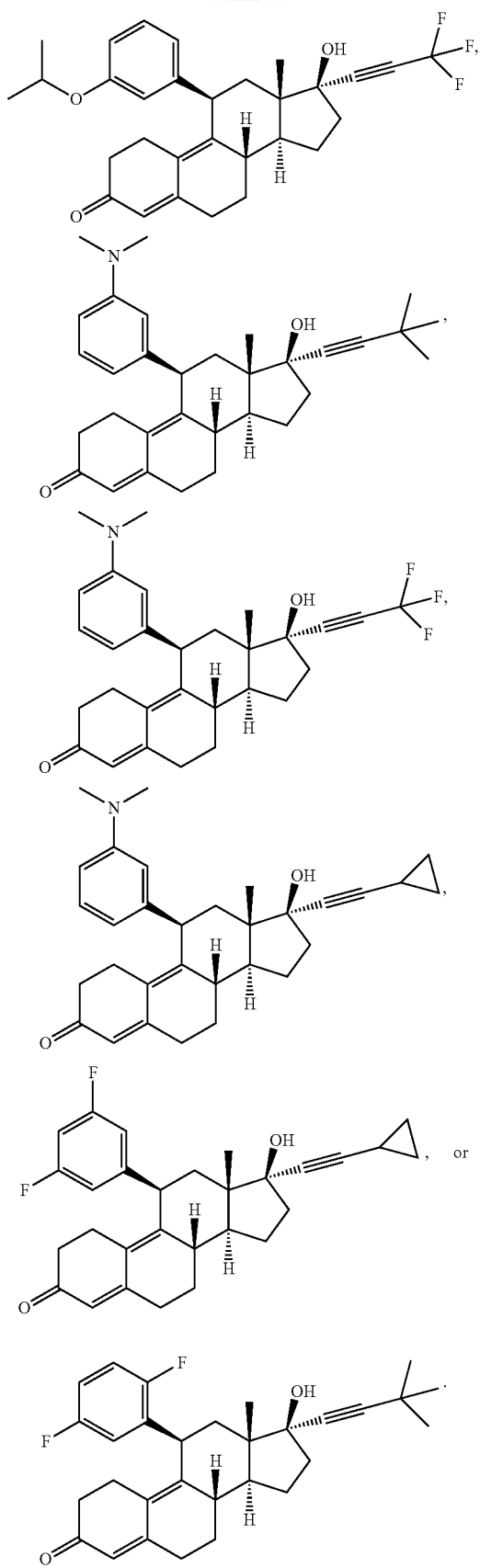
In some embodiments, a compound of formula (II) has the structure of
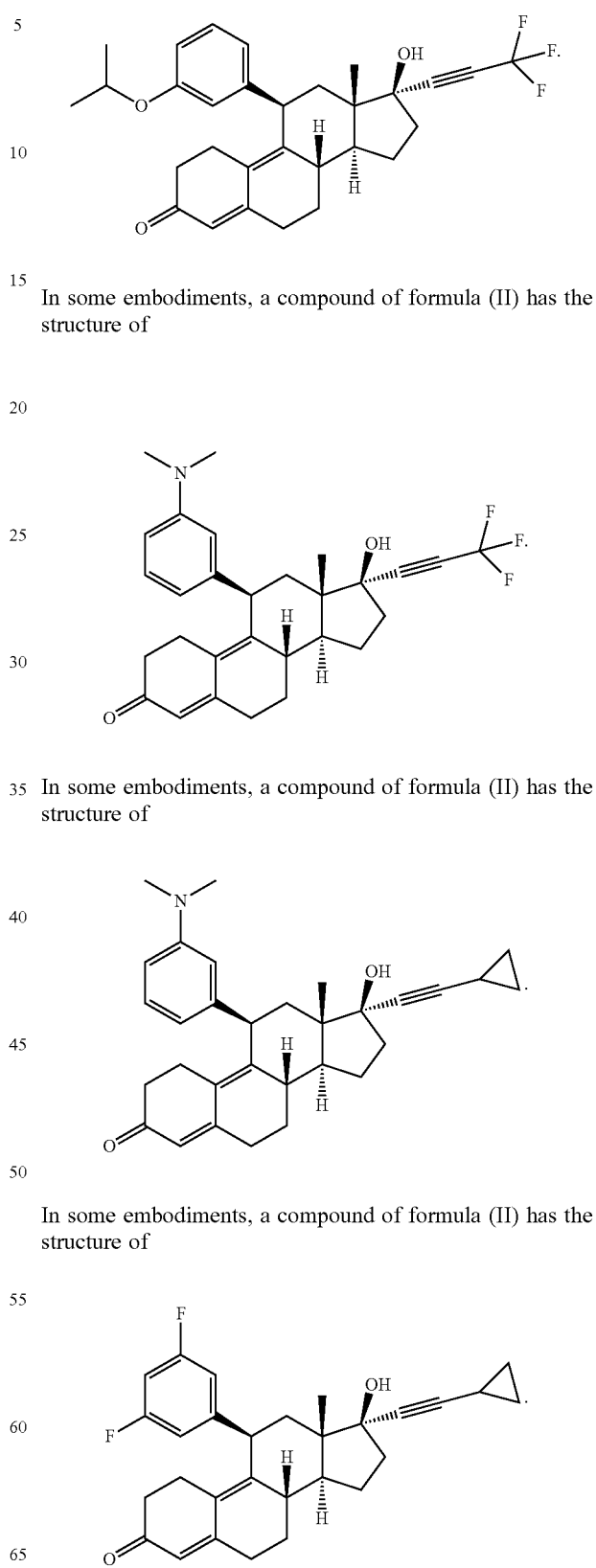
In some embodiments, a compound of formula (II) has the structure of
In some embodiments, a compound of formula (II) has the structure of
In some embodiments, a compound of formula (II) has the structure of In some embodiments, a compound of formula (II) has the structure of

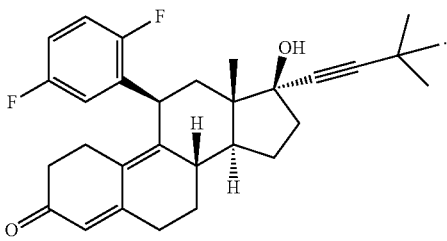

Some embodiments provided herein describe a compound having the structure of Formula (III), or a pharmaceutically acceptable salt or prodrug thereof:

Formula (III)

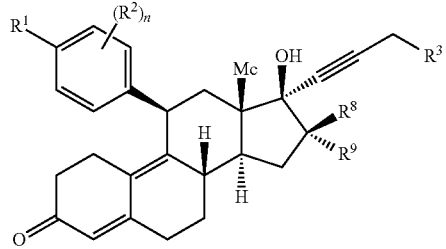

wherein
$R^1$ is —$NR^4R^5$, optionally substituted alkyl$NR^4R^5$, halo, —$OR^6$, —OH, optionally substituted alkyl, fluoroalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —$C(O)OR^6$, —$C(O)NR^4R^5$, —$OC(O)OR^6$, —$OC(O)NR^4R^5$, —$S(O)_2NR^4R^5$, —$S(O)_2R^7$, —$S(O)R^7$, —$SR^7$, —$NR^4S(O)_2NR^4R^5$, —$P(O)(OR^6)_2$, —$P(O)(R^6)_2$, —CN, —$CO_2H$, or —$NO_2$;

$R^2$ is —$NR^4R^5$, optionally substituted alkyl$NR^4R^5$, halo, —$OR^6$, —OH, optionally substituted alkyl, fluoroalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, —$C(O)R^6$, —$C(O)OR^6$, —$C(O)NR^4R^5$, —$OC(O)OR^6$, —$OC(O)NR^4R^5$, —$S(O)_2NR^4R^5$, —$S(O)_2R^7$, —$S(O)R^7$, —$SR^7$, —$NR^4S(O)_2NR^4R^5$, —CN, —$CO_2H$, or —$NO_2$;

$R^3$ is optionally substituted heteroalkyl, optionally substituted alkyl, fluoroalkyl, halo, deuteroalkyl, optionally substituted carbocyclyl, optionally substituted carbocyclylalkyl, optionally substituted heterocyclyl, optionally substituted heterocyclylalkyl, optionally substituted aryl, optionally substituted heteroaryl, —$Si(R^6)_3$, —$OR^6$, or —$S(O)_2R^7$;

$R^4$ and $R^5$ are each independently —H, optionally substituted alkyl, fluoroalkyl, optionally substituted $C_{3-5}$ carbocyclyl, optionally substituted aryl, optionally substituted heterocyclyl, optionally substituted heteroaryl, —$S(O)_2R^7$, —$C(O)N(R^{10})_2$, —$C(O)R^6$, or —$C(O)OR^6$;
or $R^4$ and $R^5$ attached to the same N atom are taken together with the N atom to which they are attached to form a substituted or unsubstituted heterocycle;

each $R^6$ is independently optionally substituted alkyl, fluoroalkyl, optionally substituted carbocyclyl, optionally substituted aryl, optionally substituted heterocyclyl, or optionally substituted heteroaryl;

$R^7$ is optionally substituted alkyl, fluoroalkyl, optionally substituted carbocyclyl, optionally substituted aryl, optionally substituted heterocyclyl, or optionally substituted heteroaryl;

$R^8$ and $R^9$ are each independently —H, optionally substituted alkyl, fluoroalkyl, halo, optionally substituted carbocyclyl, optionally substituted carbocyclylalkyl, optionally substituted heteroalkyl, optionally substituted heterocyclyl, optionally substituted heterocyclylalkyl, —OH, —$OR^6$, —$NR^4R^5$, —$C(O)NR^4R^5$, —CN, —$S(O)_2R^7$, —$C(O)_2H$, —$C(O)R^6$, or —$C(O)OR^6$;
or $R^8$ and $R^9$ are taken together with the atom to which they are attached to form a substituted or unsubstituted ring containing 0-2 heteroatoms selected from the group consisting of —O—, —NH—, —$NR^6$—, —S—, and —$S(O)_2$—; and each $R^{10}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

n is 0, 1, 2, 3, or 4.

For any and all of the embodiments of Formula (III), substituents are selected from among a subset of the listed alternatives provided for Formula (I).

Some embodiments provided herein describe a compound having the structure of Formula (IV), or a pharmaceutically acceptable salt or prodrug thereof:

Formula (IV)

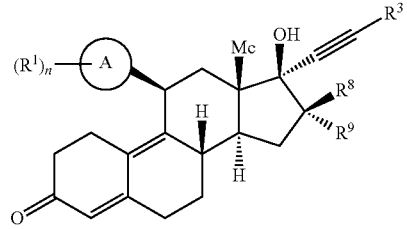

wherein
ring A is a heteroaryl, aryl, carbocyclyl, or heterocyclyl;
$R^1$ is —H, —$NR^4R^5$, optionally substituted alkyl$NR^4R^5$, halo, —$OR^6$, —OH, optionally substituted alkyl, fluoroalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —$C(O)OR^6$, —$C(O)NR^4R^5$, —$OC(O)OR^6$, —$OC(O)NR^4R^5$, —$S(O)_2NR^4R^5$, —$S(O)_2R^7$, —$S(O)R^7$, —$SR^7$, —$NR^4S(O)_2NR^4R^5$, —$P(O)(OR^6)_2$, —$P(O)(R^6)_2$, —CN, —$CO_2H$, or —$NO_2$;

$R^3$ is optionally substituted $C_{2-10}$ alkyl, fluoroalkyl, halo, deuteroalkyl, optionally substituted carbocyclyl, optionally substituted carbocyclylalkyl, optionally substituted heterocyclyl, optionally substituted heterocyclylalkyl, optionally substituted aryl, optionally substituted heteroaryl, —$Si(R^6)_3$, —$OR^6$, or —$S(O)_2R^7$;

$R^4$ and $R^5$ are each independently —H, optionally substituted alkyl, fluoroalkyl, optionally substituted carbocyclyl, optionally substituted aryl, optionally substituted heterocyclyl, optionally substituted heteroaryl, —S(O)$_2$R$^7$, —C(O)N(R$^{10}$), —C(O)R$^6$, or —C(O)OR$^6$;

or R$^4$ and R$^5$ attached to the same N atom are taken together with the N atom to which they are attached to form a substituted or unsubstituted heterocycle;

each R$^6$ is independently optionally substituted alkyl, fluoroalkyl, optionally substituted carbocyclyl, optionally substituted aryl, optionally substituted heterocyclyl, or optionally substituted heteroaryl;

R$^7$ is optionally substituted alkyl, fluoroalkyl, optionally substituted carbocyclyl, optionally substituted heteroalkyl, optionally substituted aryl, optionally substituted aralkyl, optionally substituted heterocyclyl, or optionally substituted heteroaryl;

R$^8$ and R$^9$ are each independently —H, optionally substituted alkyl, fluoroalkyl, halo, optionally substituted carbocyclyl, optionally substituted carbocyclylalkyl, optionally substituted heteroalkyl, optionally substituted heterocyclyl, optionally substituted heterocyclylalkyl, —OH, —OR$^6$, —NR$^4$R$^5$, —C(O)NR$^4$R$^5$, —CN, —S(O)$_2$R$^7$, —C(O)$_2$H, —C(O)R$^6$, or —C(O)OR$^6$;

or R$^8$ and R$^9$ are taken together with the atom to which they are attached to form a substituted or unsubstituted ring containing 0-2 heteroatoms selected from the group consisting of —O—, —NH—, —NR$^6$—, —S—, and —S(O)$_2$—;

each R$^{10}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl.

n is 0, 1, 2, 3, or 4.

Some embodiments provided herein describe a compound having the structure of Formula (IV), wherein ring A is a heteroaryl, aryl, carbocyclyl, or heterocyclyl;

R$^1$ is —H, —NR$^4$R$^5$, optionally substituted alkylNR$^4$R$^5$, halo, —OR$^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —C(O)OR$^6$, —C(O)NR$^4$R$^5$, —OC(O)R$^6$, —OC(O)NR$^4$R$^5$, —S(O)$_2$NR$^4$R$^5$, —S(O)$_2$R$^7$, —S(O)R$^7$, —SR$^7$, —NR$^4$S(O)$_2$NR$^4$R$^5$, —P(O)(OR$^6$)$_2$, —P(O)(R$^6$)$_2$, —CN, —CO$_2$H, or —NO$_2$;

R$^3$ is optionally substituted alkyl, fluoroalkyl, halo, deuteroalkyl, optionally substituted carbocyclyl, optionally substituted carbocyclylalkyl, optionally substituted heterocyclyl, optionally substituted heterocyclylalkyl, optionally substituted aryl, optionally substituted heteroaryl, —Si(R$^6$)$_3$, —OR$^6$, or —S(O)$_2$R$^7$;

R$^4$ and R$^5$ are each independently —H, optionally substituted alkyl, haloalkyl, optionally substituted carbocyclyl, optionally substituted aryl, optionally substituted heterocyclyl, optionally substituted heteroaryl, —S(O)$_2$R$^7$, —C(O)N(R$^{10}$)$_2$, —C(O)R$^6$, or —C(O)OR$^6$;

or R$^4$ and R$^5$ attached to the same N atom are taken together with the N atom to which they are attached to form a substituted or unsubstituted heterocycle;

each R$^6$ is independently optionally substituted alkyl, haloalkyl, optionally substituted carbocyclyl, optionally substituted aryl, optionally substituted heterocyclyl, or optionally substituted heteroaryl;

R$^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

R$^8$ and R$^9$ are each independently —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —OR$^6$, —NR$^4$R$^5$, —C(O)NR$^4$R$^5$, —CN, —S(O)$_2$R$^7$, —C(O)$_2$H, —C(O)R$^6$, or —C(O)OR$^6$;

R$^9$ is —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —OR, —NR$^4$R$^5$, —C(O)NR$^4$R$^5$, —CN, —S(O)$_2$R$^7$, —C(O)$_2$H, —C(O)R$^6$, or —C(O)OR$^6$;

or R$^8$ and R$^9$ are taken together with the atom to which they are attached to form a substituted or unsubstituted ring containing 0-2 heteroatoms selected from the group consisting of —O—, —NH—, —NR$^6$—, —S—, and —S(O)$_2$—;

each R$^{10}$ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

and n is 0, 1, 2, 3, or 4.

Other embodiments provided herein describe a compound having the structure of Formula (IV), wherein ring A is a heteroaryl, aryl, carbocyclyl, or heterocyclyl;

R$^1$ is —H, —NR$^4$R$^5$, optionally substituted alkylNR$^4$R$^5$, halo, —OR$^6$, —OH, optionally substituted alkyl, haloalkyl, optionally substituted carbocyclyl, optionally substituted carbocyclylalkyl, optionally substituted heteroalkyl, optionally substituted heterocyclyl, optionally substituted heterocyclylalkyl, optionally substituted hydroxyalkyl, optionally substituted aryl, optionally substituted heteroaryl, —C(O)OR$^6$, —C(O)NR$^4$R$^5$, —OC(O)OR$^6$, —OC(O)NR$^4$R$^5$, —S(O)$_2$NR$^4$R$^5$, —S(O)$_2$R$^7$, —S(O)R$^7$, —SR$^7$, —NR$^4$S(O)$_2$NR$^4$R$^5$, —P(O)(OR$^6$)$_2$, —P(O)(R$^6$)$_2$, —CN, —CO$_2$H, or —NO$_2$;

R$^3$ is optionally substituted alkyl, fluoroalkyl, halo, deuteroalkyl, optionally substituted carbocyclyl, optionally substituted carbocyclylalkyl, optionally substituted heterocyclyl, optionally substituted heterocyclylalkyl, optionally substituted aryl, optionally substituted heteroaryl, —Si(R$^6$)$_3$, —OR$^6$, or —S(O)$_2$R$^7$;

R$^4$ and R$^5$ are each independently —H, optionally substituted alkyl, haloalkyl, optionally substituted carbocyclyl, optionally substituted aryl, optionally substituted heterocyclyl, optionally substituted heteroaryl, —S(O)$_2$R$^7$, —C(O)N(R$^{10}$)$_2$, —C(O)R$^6$, or —C(O)OR$^6$;

or R$^4$ and R$^5$ attached to the same N atom are taken together with the N atom to which they are attached to form a substituted or unsubstituted heterocycle;

each R$^6$ is independently optionally substituted alkyl, haloalkyl, optionally substituted carbocyclyl, optionally substituted aryl, optionally substituted heterocyclyl, or optionally substituted heteroaryl;

R$^7$ is optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

R$^8$ is —H, optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —OR, —NR⁴R⁵, —C(O)NR⁴R⁵, —CN, —S(O)₂R⁷, —C(O)₂H, —C(O)R⁶, or —C(O)OR⁶;

R⁹ is optionally substituted alkyl, haloalkyl, halo, optionally substituted carbocyclyl, optionally substituted carbocyclylalkyl, optionally substituted heteroalkyl, optionally substituted heterocyclyl, optionally substituted heterocyclylalkyl, —OH, —OR⁶, —NR⁴R⁵, —C(O)NR⁴R⁵, —CN, —S(O)₂R⁷, —C(O)₂H, —C(O)R⁶, or —C(O)OR⁶;

or R⁸ and R⁹ are taken together with the atom to which they are attached to form a substituted or unsubstituted ring containing 0-2 heteroatoms selected from the group consisting of —O—, —NH—, —NR⁶—, —S—, and —S(O)₂—;

each R¹⁰ is independently H, optionally substituted alkyl, haloalkyl, optionally substituted carbocyclyl, optionally substituted heteroalkyl, optionally substituted aryl, optionally substituted aralkyl, optionally substituted heterocyclyl, or optionally substituted heteroaryl;

and n is 0, 1, 2, 3, or 4.

For any and all of the embodiments of Formula (IV), substituents are selected from among a subset of the listed alternatives provided for Formula (I) and the listed alternatives below.

In some embodiments, ring A is a bicyclic heteroaryl. In some embodiments, ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments, ring A is a monocyclic heteroaryl, bicyclic heteroaryl, or naphthyl. In some embodiments, ring A is a bicyclic heteroaryl. In other embodiments, ring A is a monocyclic heteroaryl. In some embodiments, ring A is pyridyl. In some embodiments, ring A is 1,3-benzodioxolyl or 1,4-benzodioxanyl.

In some embodiments, R⁸ is —H and R⁹ is C₁₋₆alkyl, C₁₋₆haloalkyl, halo, C₃₋₆carbocyclyl, C₁₋₆alkylC₃₋₆carbocyclyl, C₁₋₆heteroalkyl, C₃₋₆heterocyclyl, C₁₋₆alkylC₃₋₆heterocyclyl, —OH, —OR⁵, —NR³R⁴, —C(O)NR³R⁴, —CN, —S(O)₂R⁶, —C(O)₂H, —C(O)R⁵, or —C(O)OR⁵ or R⁸ and R⁹ are taken together with the atom to which they are attached to form a ring containing 0-2 heteroatoms selected from the group consisting of —O—, —N—, NR⁶—, —S—, and —S(O)₂—. In some embodiments, R⁸ is —H and R⁹ is C₁₋₆alkyl, C₁₋₆fluoroalkyl, halo, or C₃₋₆carbocyclyl. In some embodiments, R⁸ is —H and R⁹ is C₁₋₆alkyl, or C₃₋₆carbocyclyl. In some embodiments, R⁸ is —H and R⁹ is alkyl. In some embodiments, R⁸ is —H and R⁹ is methyl. In some embodiments, R⁸ is —H and R⁹ is ethyl.

In some embodiments, R⁹ is —H and R⁸ is C₁₋₆alkyl, C₁₋₆haloalkyl, halo, C₃₋₆carbocyclyl, C₁₋₆alkylC₃₋₆carbocyclyl, C₁₋₆heteroalkyl, C₃₋₆heterocyclyl, C₁₋₆alkylC₃₋₆heterocyclyl, —OH, —OR⁵, —NR³R⁴, —C(O)NR³R⁴, —CN, —S(O)₂R⁶, —C(O)₂H, —C(O)R⁵, or —C(O)OR⁵ or R⁹ and R⁸ are taken together with the atom to which they are attached to form a ring containing 0-2 heteroatoms selected from the group consisting of —O—, —N—, NR⁶—, —S—, and —S(O)₂—. In some embodiments, R⁹ is —H and R⁸ is C₁₋₆alkyl, C₁₋₆fluoroalkyl, halo, or C₃₋₆carbocyclyl. In some embodiments, R⁹ is —H and R⁸ is C₁₋₆alkyl, or C₃₋₆carbocyclyl. In some embodiments, R⁹ is —H and R⁸ is alkyl. In some embodiments, R⁹ is —H and R⁸ is methyl. In some embodiments, R⁹ is —H and R⁸ is ethyl.

In some embodiments, R⁸ and R⁹ are C₁₋₆alkyl. In some embodiments, R⁸ and R⁹ are methyl. In some embodiments, R⁸ and R⁹ are halo.

In other embodiments, R⁸ and R⁹ are taken together with the atom to which they are attached to form a 3-, 4-, 5-, or 6-membered ring containing 0-2 heteroatoms selected from the group consisting of —O—, —NH—, —NR⁶—, —S—, and —S(O)₂—. In some embodiments, R⁸ and R⁹ are taken together with the atom to which they are attached to form a 3-, 4-, 5-, or 6-membered carbocycle ring. In some embodiments, R⁸ and R⁹ are taken together with the atom to which they are attached to form a cyclopropyl.

In some embodiments, n is 0, 1, or 2. In some embodiments, n is 0. In some embodiments, n is 1. In some embodiments, n is 2. In some embodiments, n is 3 or 4.

In some embodiments, compounds of Formula (IV) described herein have the following structure of Formula (IVa) or Formula (IVb):

Formula (IVa)

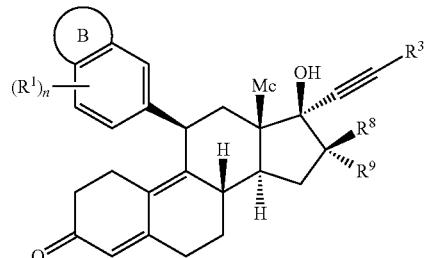

Formula (IVb)

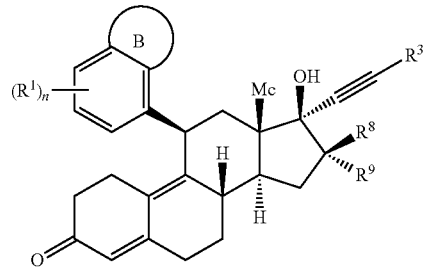

wherein ring B is an optionally substituted fused carbocyclyl, optionally substituted fused heterocyclyl, optionally substituted fused aryl, or optionally substituted fused heteroaryl;

and n is 0, 1, 2, or 3.

Some embodiments provided herein describe a compound having the structure:

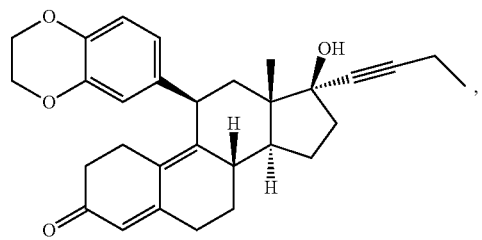

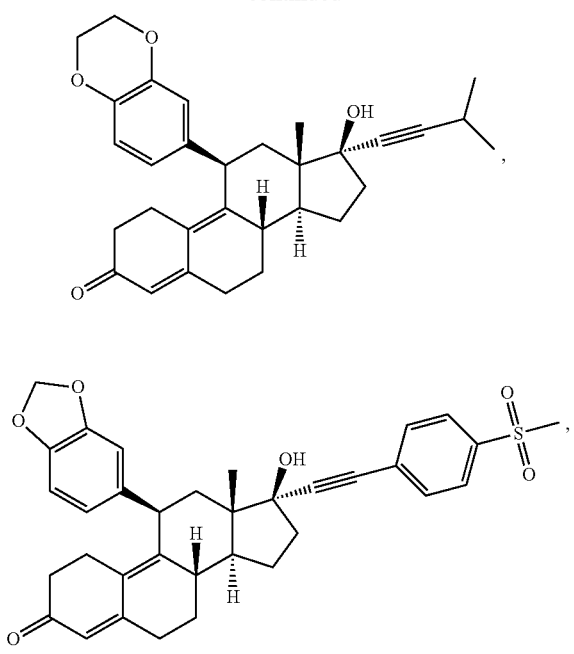
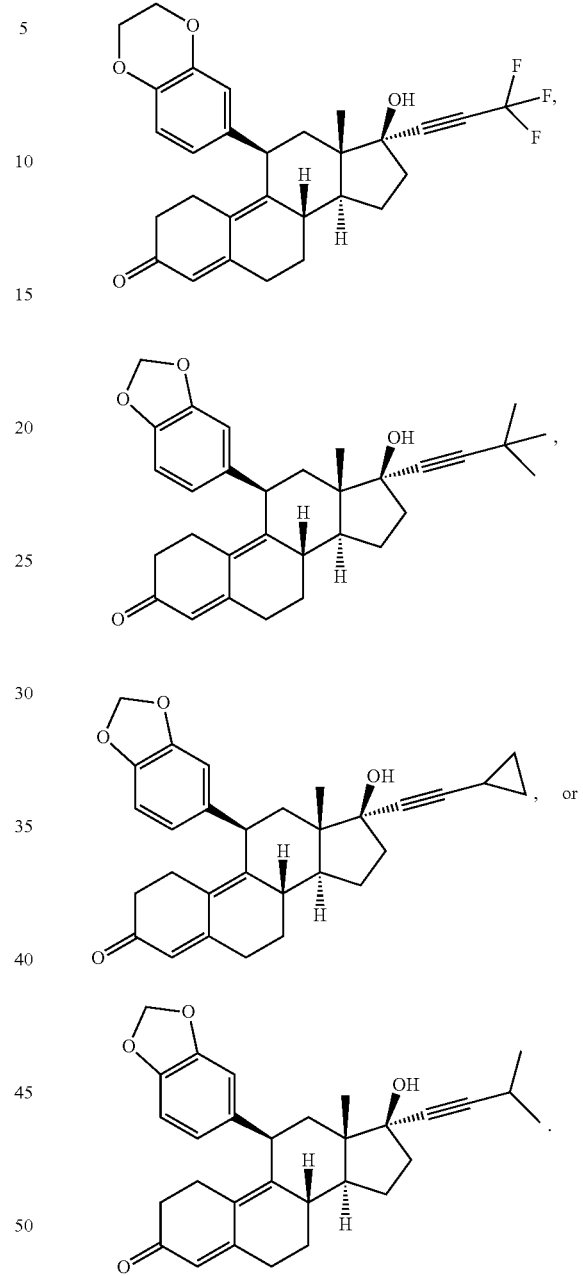
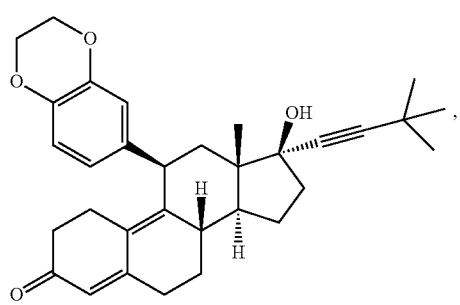
In some embodiments, a compound of formula (IV) has the structure of
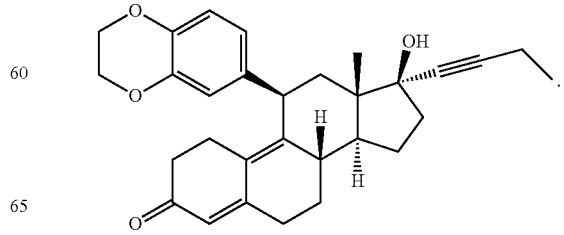

In some embodiments, a compound of formula (IV) has the structure of

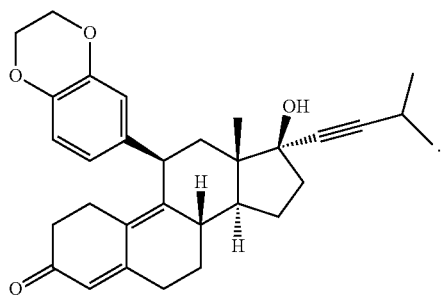

In some embodiments, a compound of formula (IV) has the structure of

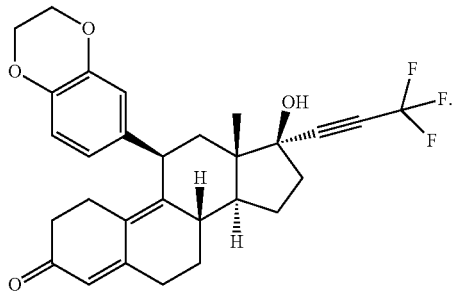

In some embodiments, a compound of formula (IV) has the structure of

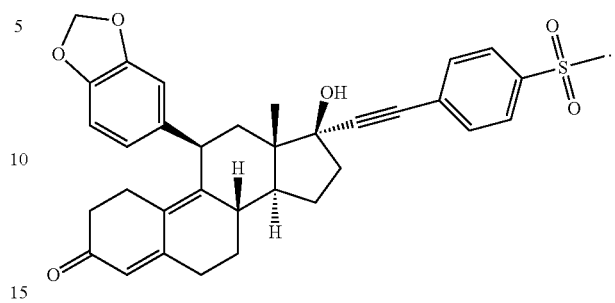

In some embodiments, a compound of formula (IV) has the structure of

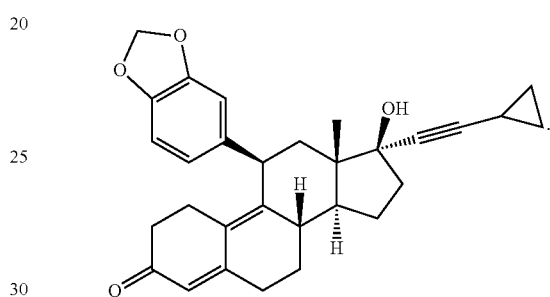

In some embodiments, the substituted steroidal derivative compound described in Formulas provided herein has a structure provided in Table 1.

TABLE 1

| Structure | Mass, [M + H]⁺ |
|---|---|
| 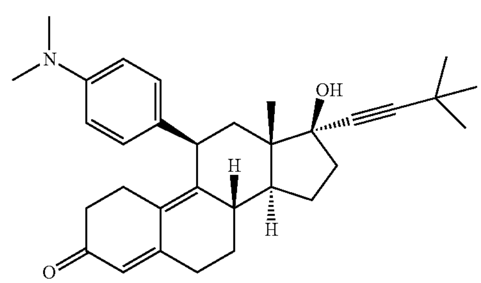 | 472.4 |
| 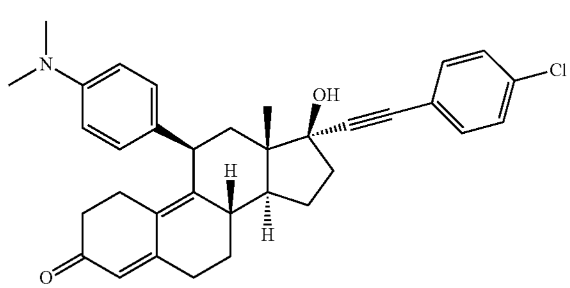 | 526.3 |

TABLE 1-continued

| Structure | Mass, [M + H]+ |
|---|---|
| 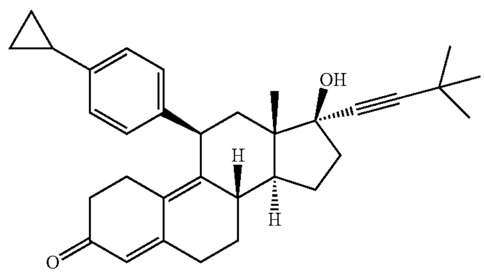 | 469.4 |
| 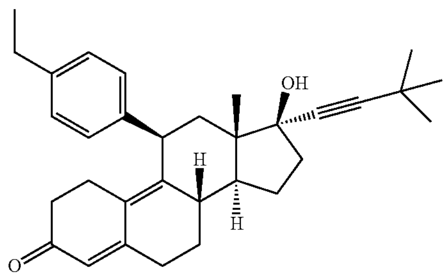 | 457.4 |
| 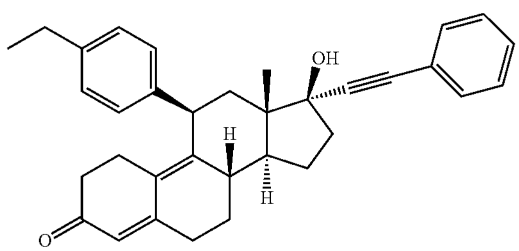 | 477.4 |
| 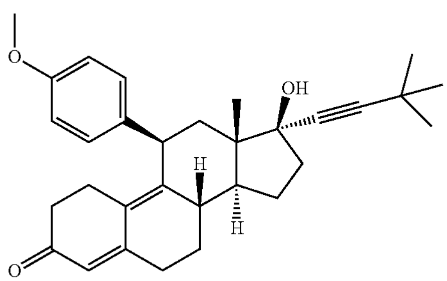 | 459.4 |
| 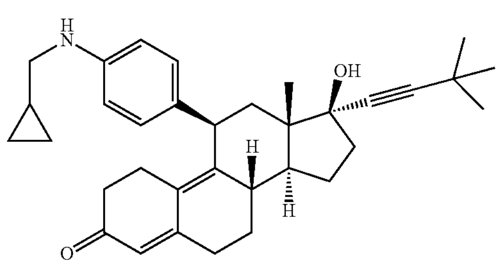 | 498.4 |

TABLE 1-continued

| Structure | Mass, [M + H]+ |
|---|---|
| 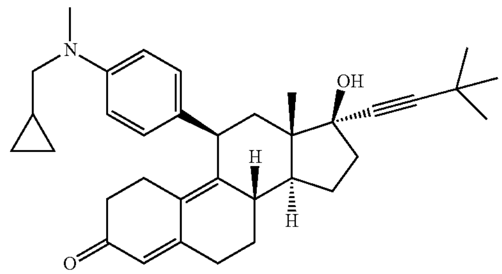 | 512.5 |
| 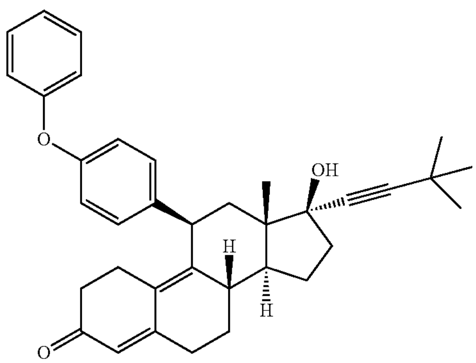 | 521.3 |
| 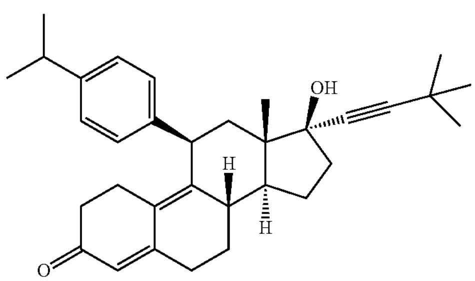 | 471.4 |
| 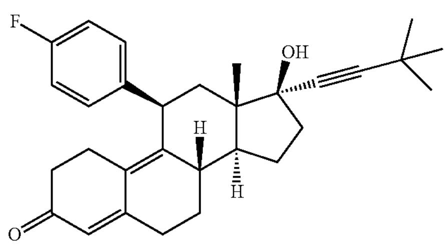 | 447.3 |
| 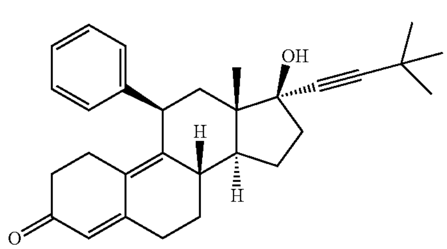 | 429.4 |

TABLE 1-continued
| Structure | Mass, [M + H]+ |
|---|---|
| 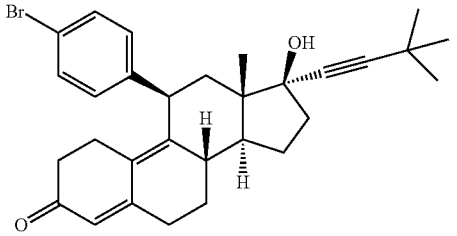 | 507.2 |
| 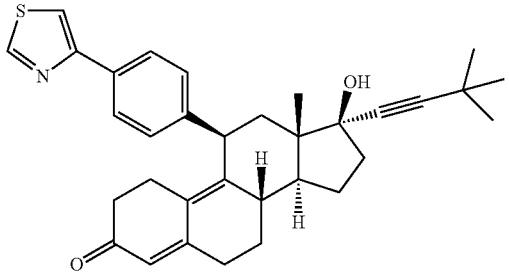 | 512.3 |
| 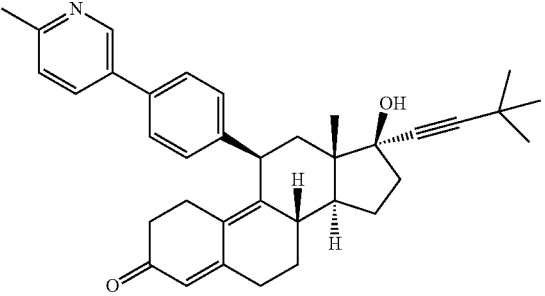 | 520.4 |
| 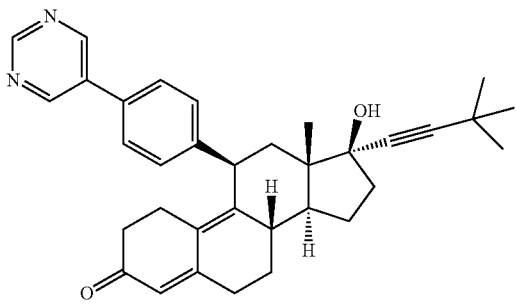 | 507.4 |
| 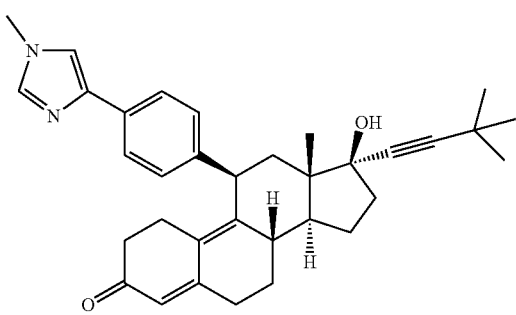 | 509.4 |

TABLE 1-continued
| Structure | Mass, [M + H]+ |
|---|---|
| 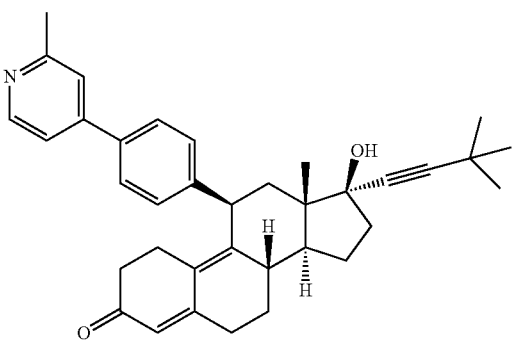 | 520.4 |
| 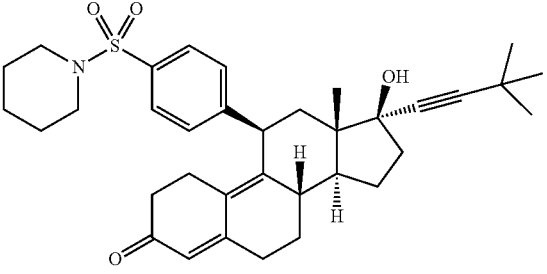 | 576.3 |
| 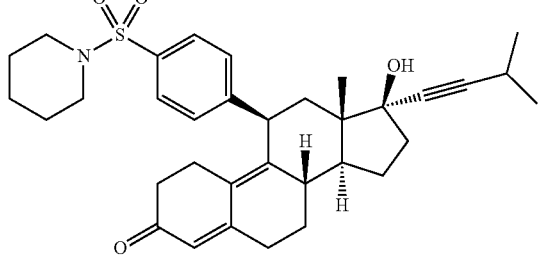 | 562.4 |
| 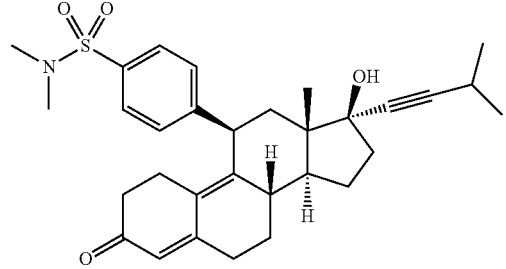 | 522.3 |
| 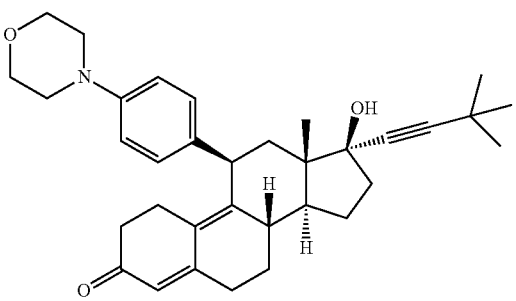 | 514.4 |

TABLE 1-continued

| Structure | Mass, [M + H]+ |
|---|---|
| 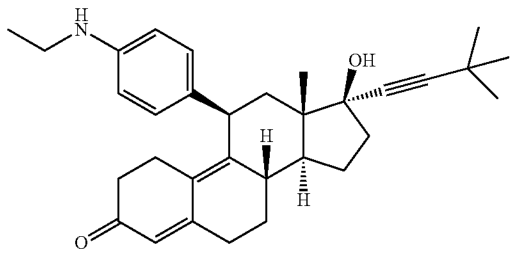 | 472.4 |
| 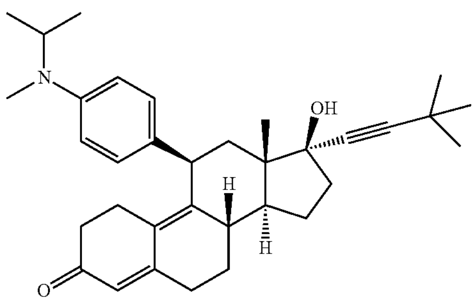 | 486.4 |
| 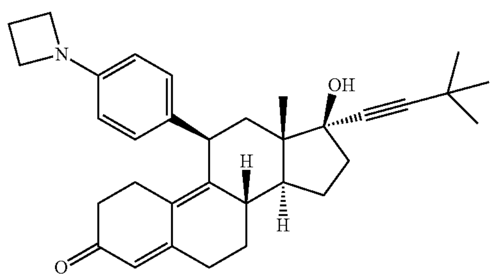 | 484.4 |
| 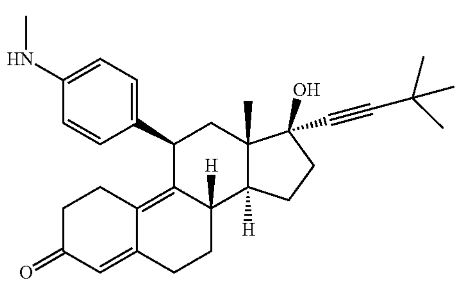 | 458.4 |
| 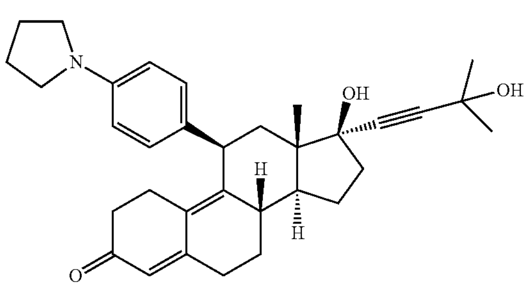 | 500.4 |

TABLE 1-continued

| Structure | Mass, [M + H]⁺ |
|---|---|
| 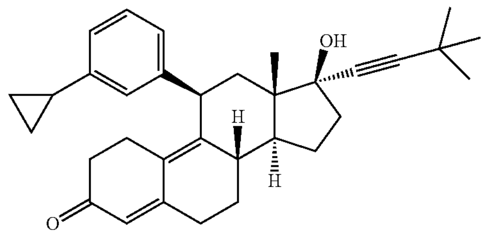 | 469.4 |
| 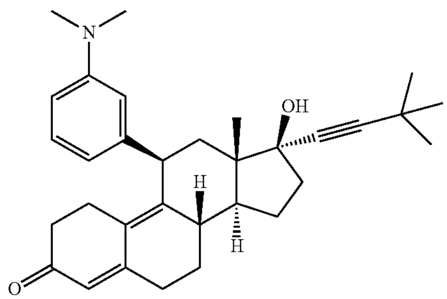 | 472.4 |
| 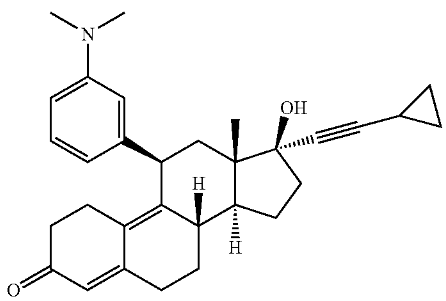 | 456.4 |
| 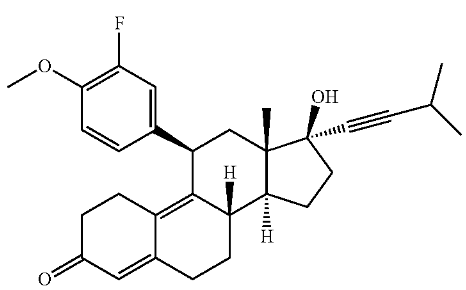 | 463.3 |
| 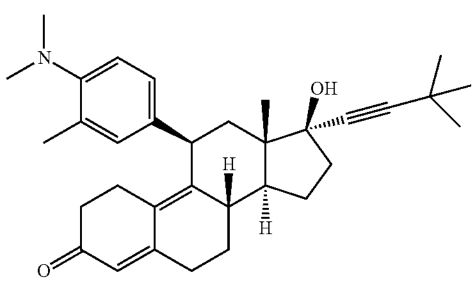 | 486.4 |

TABLE 1-continued

| Structure | Mass, [M + H]+ |
|---|---|
| 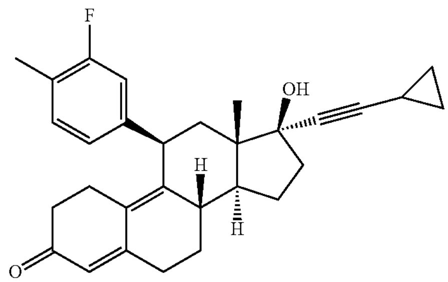 | 445.3 |
| 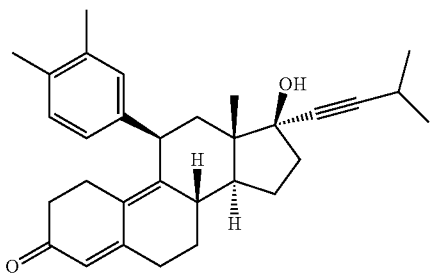 | 457.4 |
| 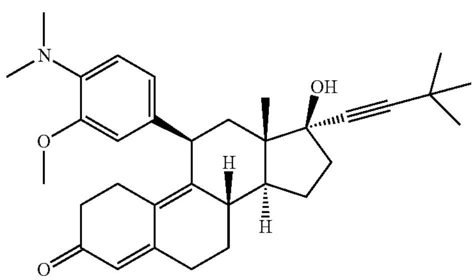 | 502.4 |
| 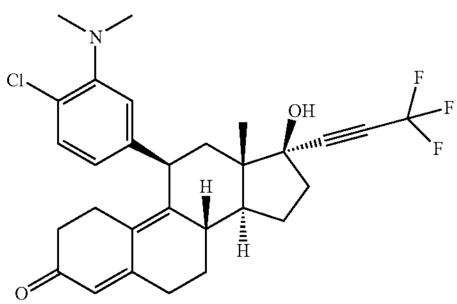 | 518.3 |
| 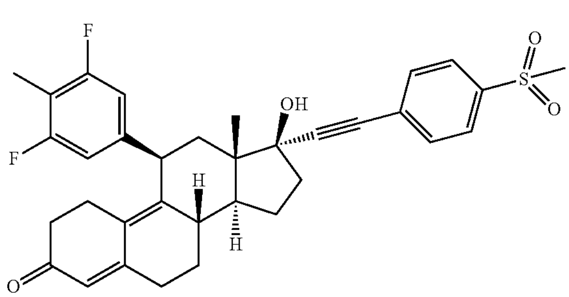 | 577.3 |

TABLE 1-continued

| Structure | Mass, [M + H]+ |
|---|---|
| 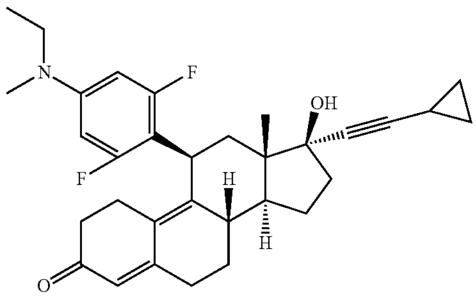 | 506.3 |
| 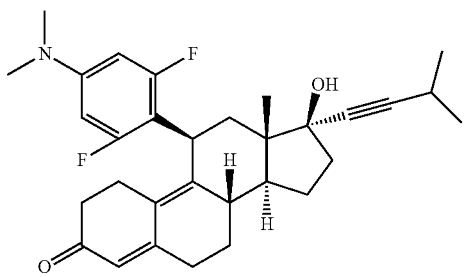 | 494.3 |
| 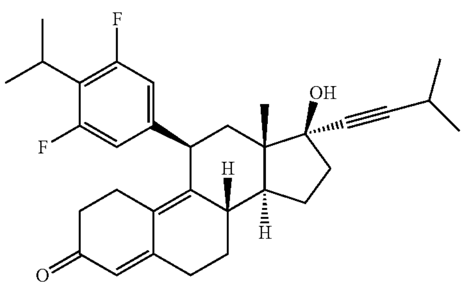 | 493.4 |
| 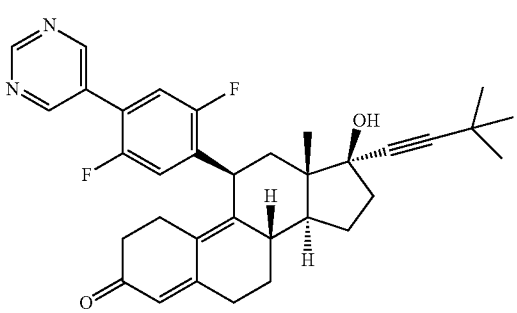 | 543.3 |
| 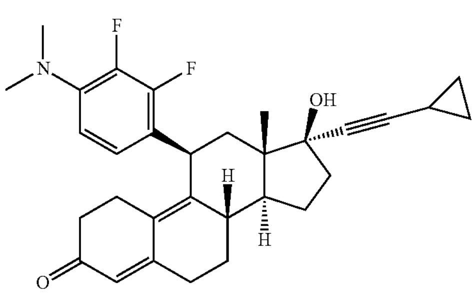 | 492.4 |

TABLE 1-continued

| Structure | Mass, [M + H]+ |
|---|---|
| 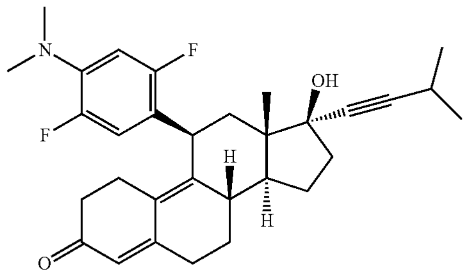 | 494.3 |
| 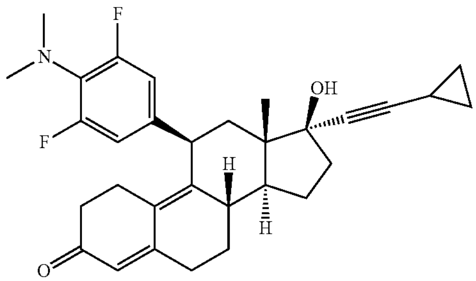 | 592.4 |
| 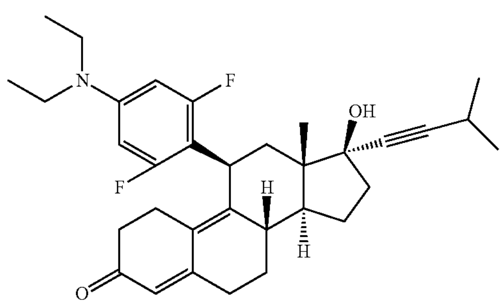 | 522.3 |
| 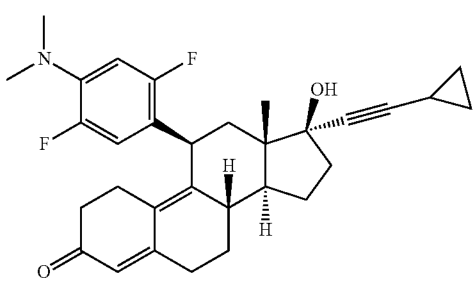 | 492.4 |
| 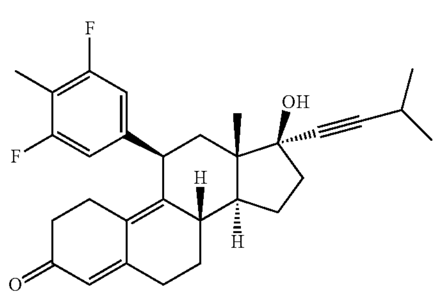 | 465.3 |

TABLE 1-continued

| Structure | Mass, [M + H]+ |
|---|---|
| 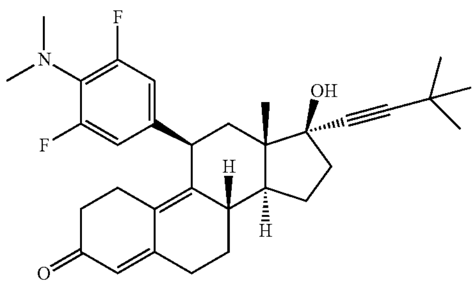 | 508.4 |
| 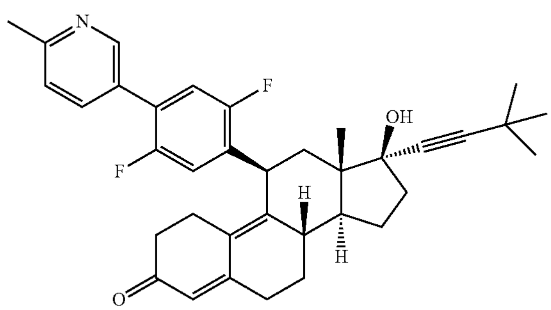 | 556.4 |
| 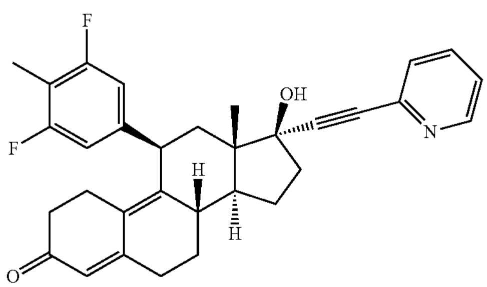 | 500.3 |
| 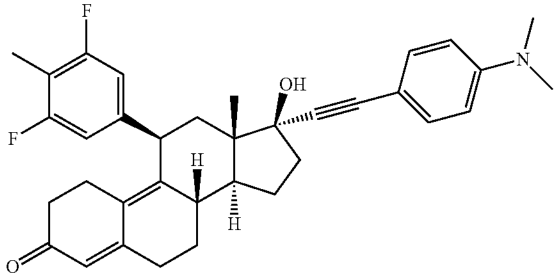 | 542.3 |
| 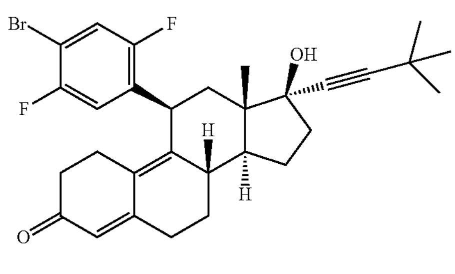 | 545.2 |

TABLE 1-continued

| Structure | Mass, [M + H]+ |
|---|---|
| 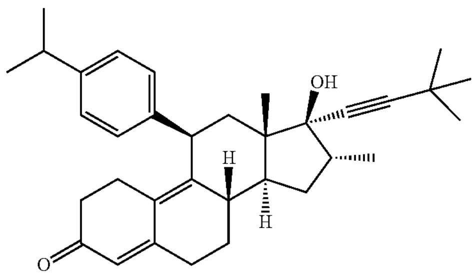 | 485.5 |
| | 473.3 |
| 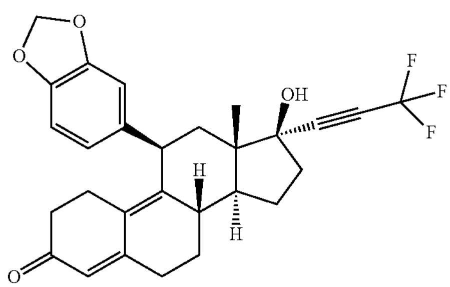 | 485.2 |
| 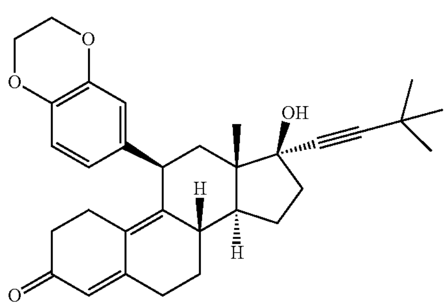 | 487.4 |
| | 473.3 |

TABLE 1-continued

| Structure | Mass, [M + H]+ |
|---|---|
| 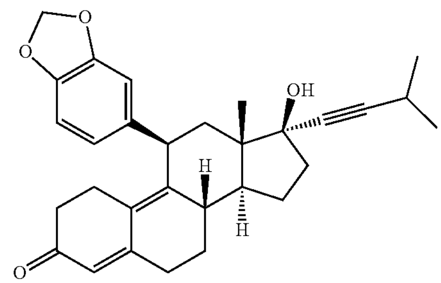 | 459.4 |
| 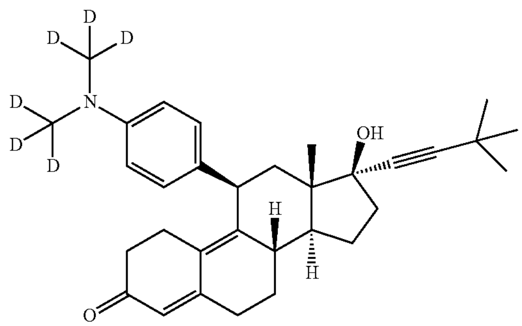 | 478.4 |
| 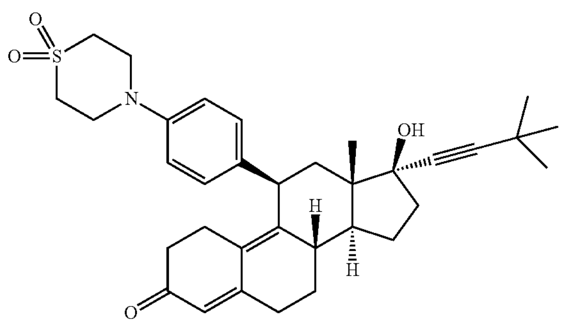 | 562.3 |
| 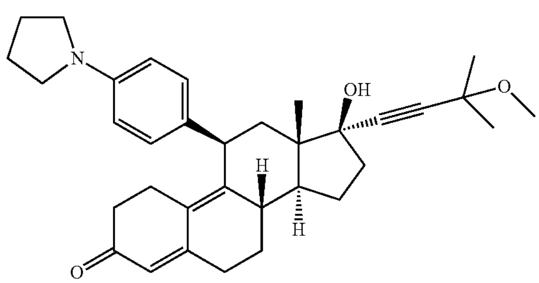 | 514.4 |
| 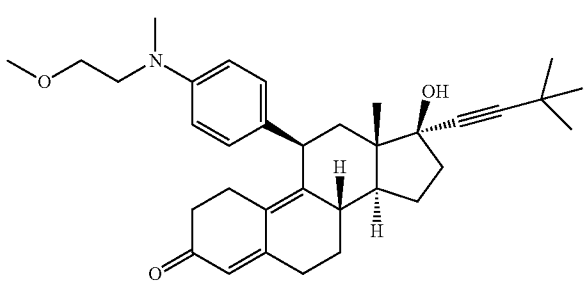 | 516.3 |

TABLE 1-continued

| Structure | Mass, [M + H]+ |
|---|---|
| 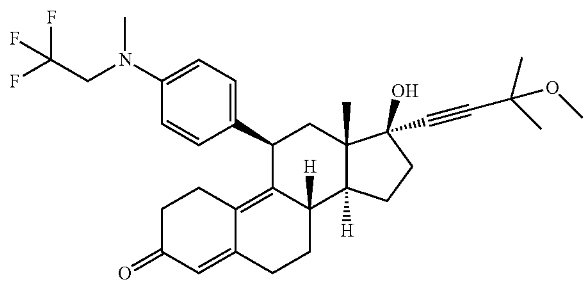 | 556.4 |
| 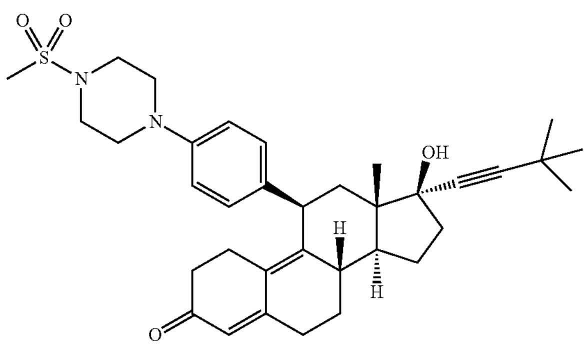 | 591.3 |
| 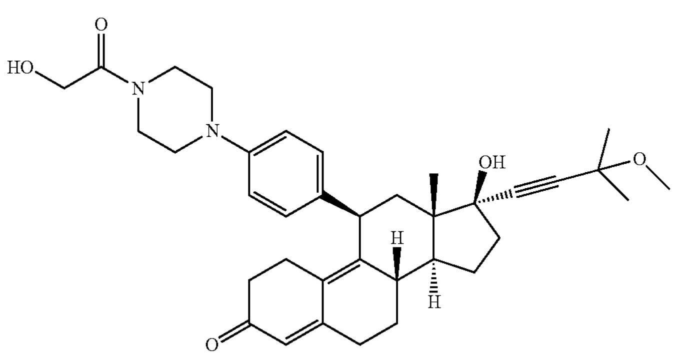 | 587.5 |
| 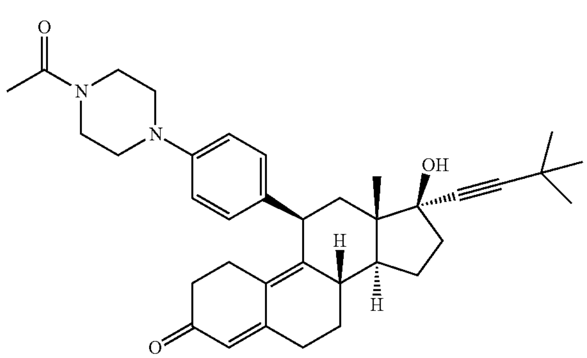 | 555.5 |

TABLE 1-continued

| Structure | Mass, [M + H]+ |
|---|---|
| 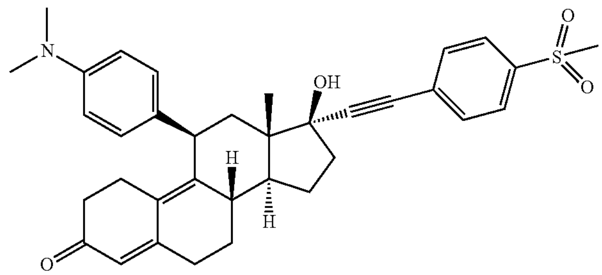 | 570.3 |
| 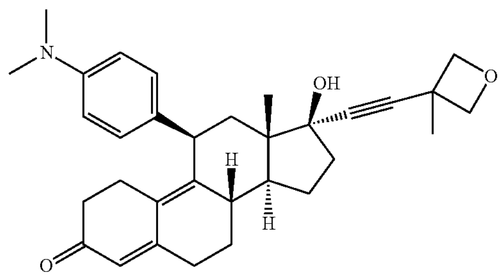 | 500.5 |
| 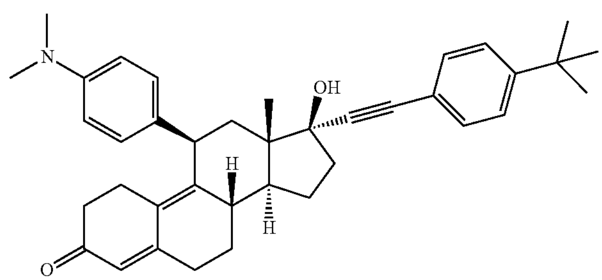 | 548.4 |
| 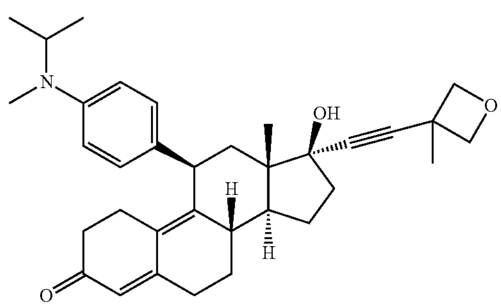 | 514.4 |
| 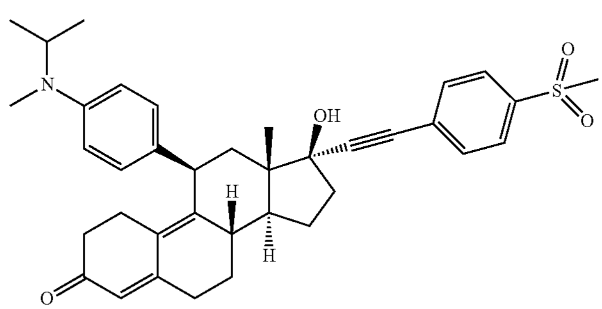 | 598.4 |

TABLE 1-continued

| Structure | Mass, [M + H]+ |
|---|---|
| 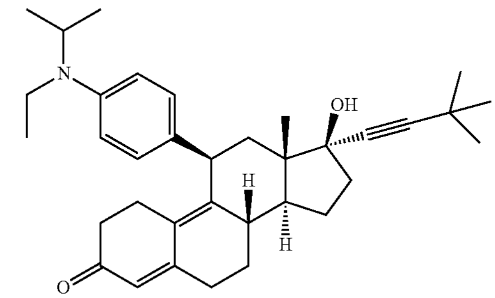 | 514.4 |
| 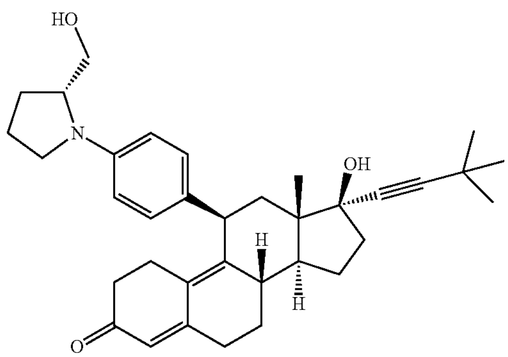 | 528.3 |
| 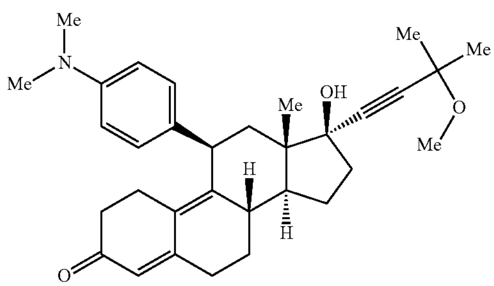 | 488.3 |
| 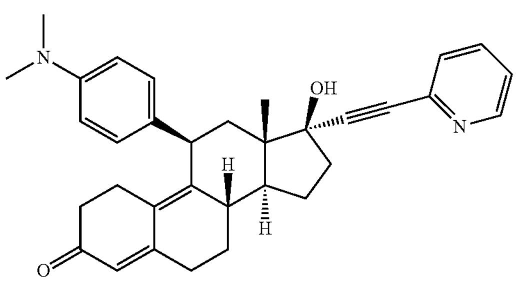 | 493.3 |
| 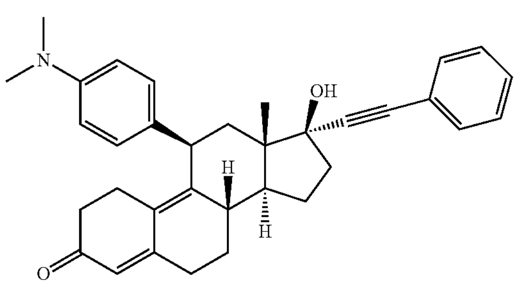 | 492.4 |

TABLE 1-continued

| Structure | Mass, [M + H]+ |
|---|---|
| 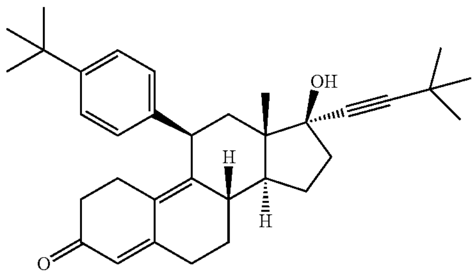 | 485.5 |
| 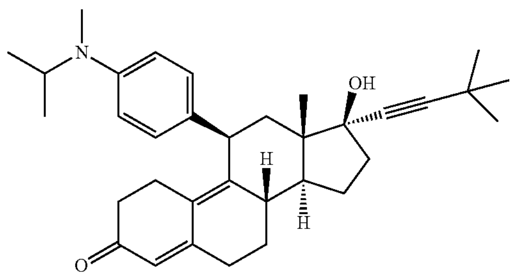 | 500.5 |
| 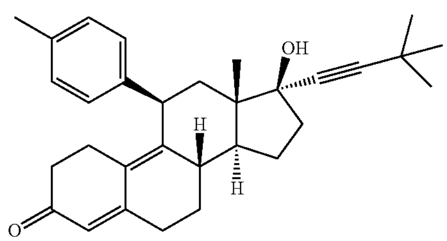 | 443.3 |
| 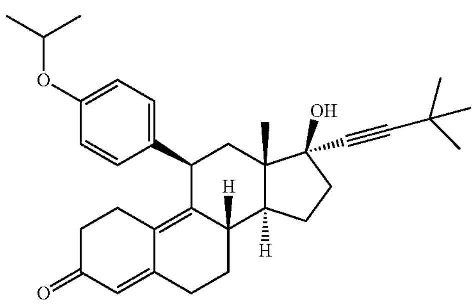 | 487.4 |
| 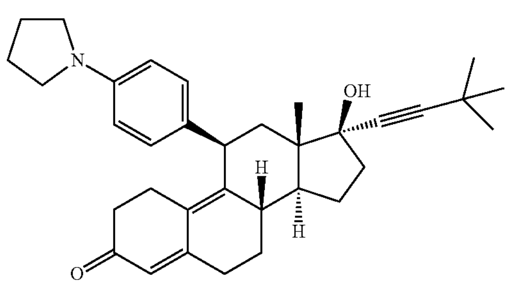 | 498.4 |

TABLE 1-continued

| Structure | Mass, [M + H]+ |
|---|---|
| 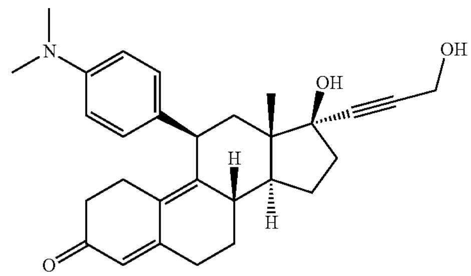 | 446.3 |
| 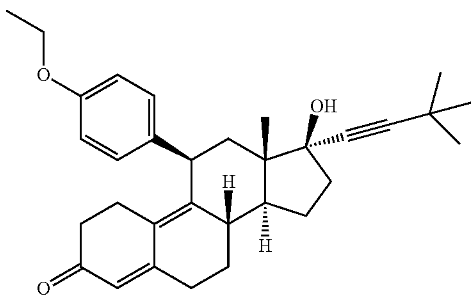 | 473.3 |
| 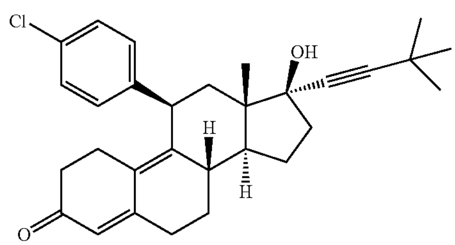 | 463.3 |
| 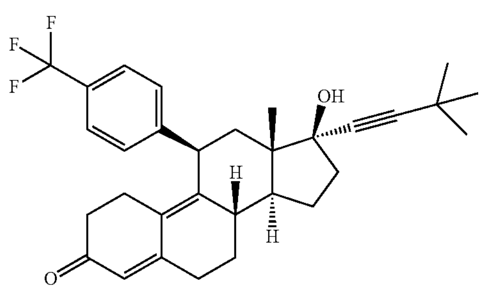 | 497.3 |
| 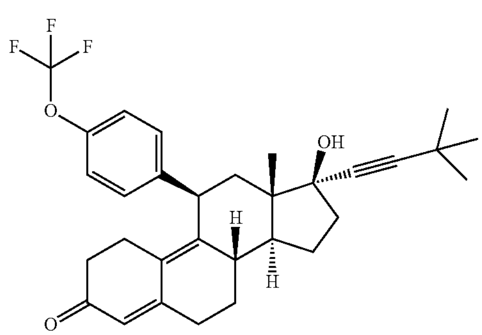 | 513.2 |

TABLE 1-continued

| Structure | Mass, [M + H]+ |
|---|---|
| 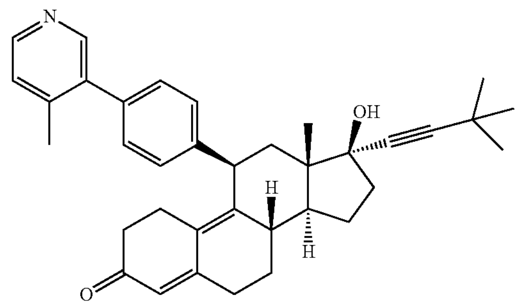 | 520.4 |
| 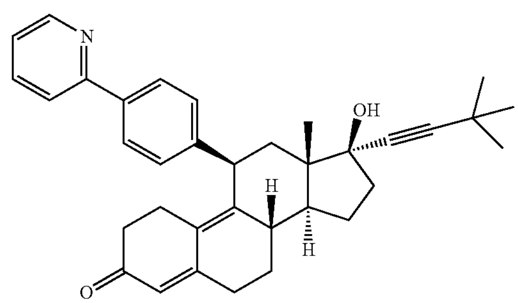 | 506.4 |
| 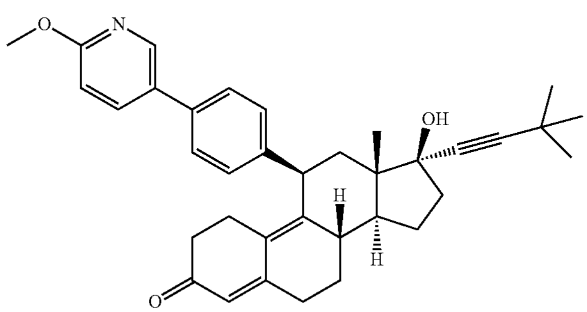 | 536.3 |
| 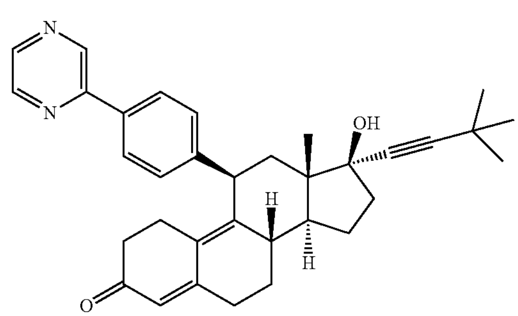 | 507.4 |
| 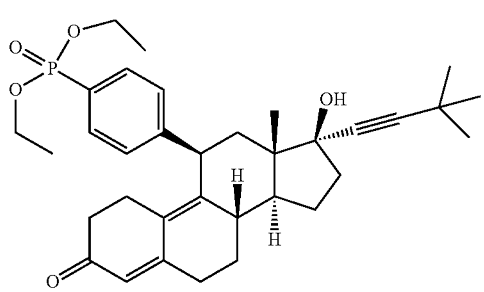 | 565.4 |

TABLE 1-continued

| Structure | Mass, [M + H]+ |
|---|---|
| 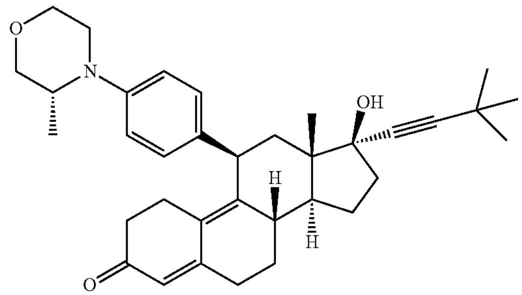 | 528.3 |
| 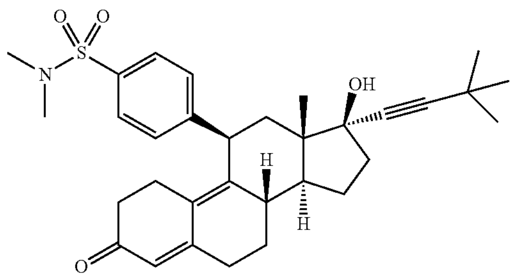 | 536.3 |
| 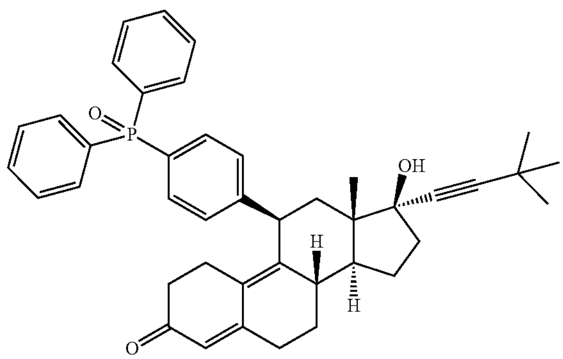 | 629.3 |
| 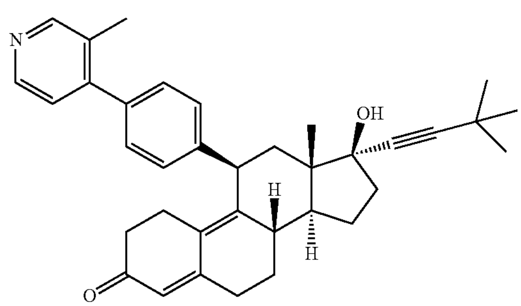 | 520.4 |
| 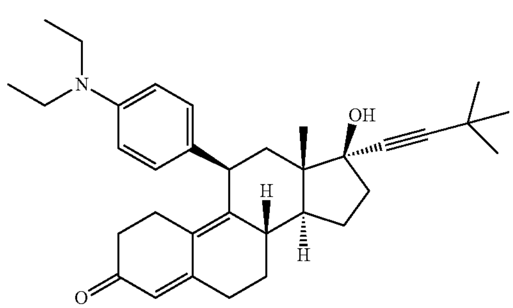 | 500.5 |

TABLE 1-continued

| Structure | Mass, [M + H]+ |
|---|---|
| 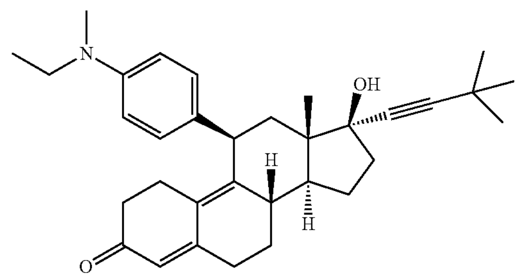 | 486.4 |
| 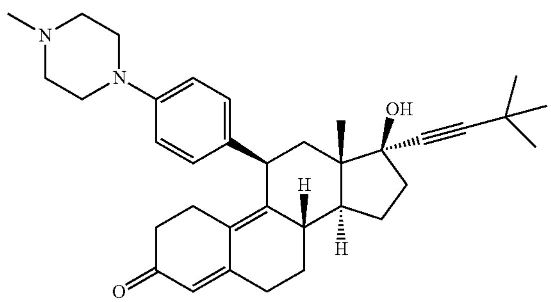 | 527.5 |
| 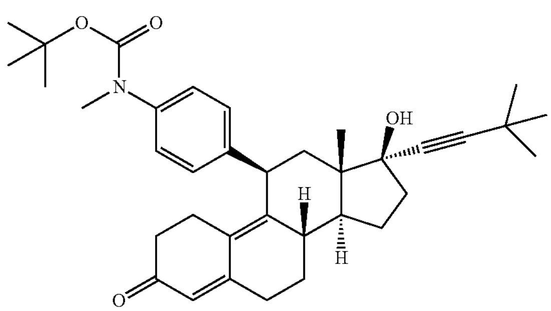 | 580.4 [M + Na]+ |
| 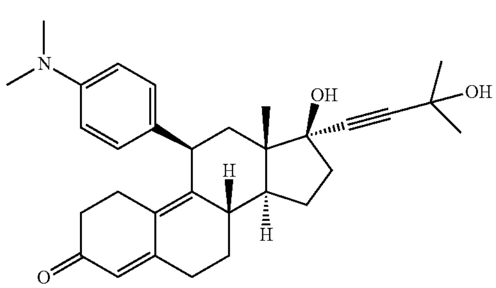 | 474.3 |
| 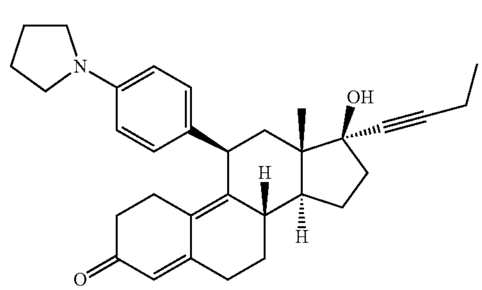 | 470.4 |

TABLE 1-continued

| Structure | Mass, [M + H]+ |
|---|---|
| 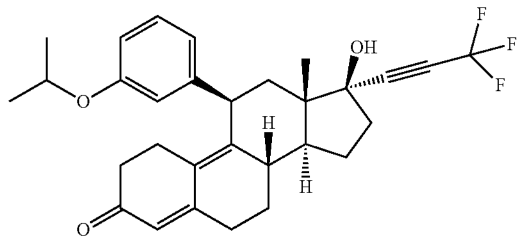 | 499.4 |
| 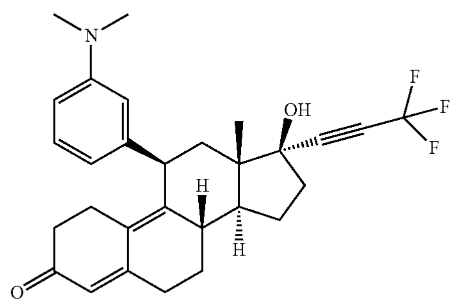 | 484.3 |
| 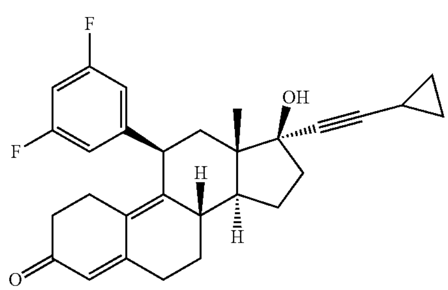 | 449.3 |
| 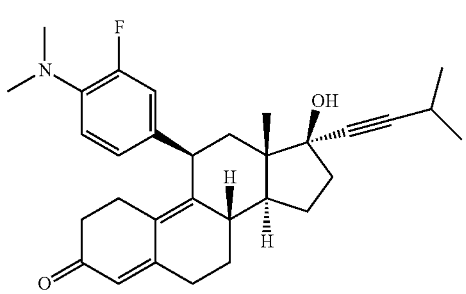 | 476.3 |
| 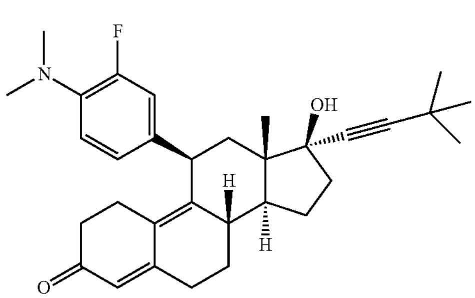 | 490.4 |

TABLE 1-continued

| Structure | Mass, [M + H]+ |
|---|---|
| 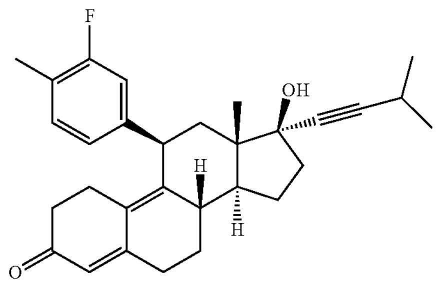 | 447.4 |
| 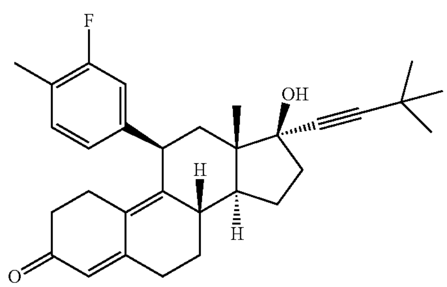 | 461.3 |
| 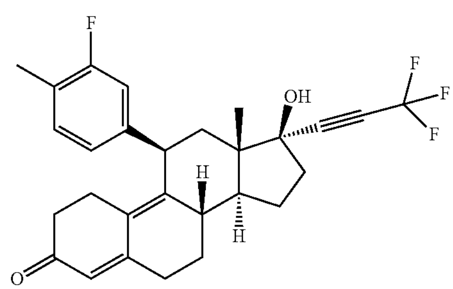 | 473.2 |
| 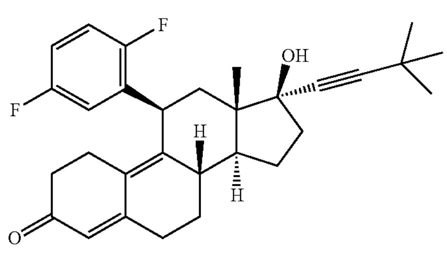 | 465.4 |
| 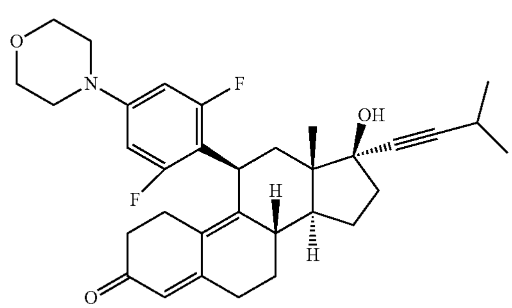 | 536.3 |

TABLE 1-continued

| Structure | Mass, [M + H]+ |
|---|---|
| 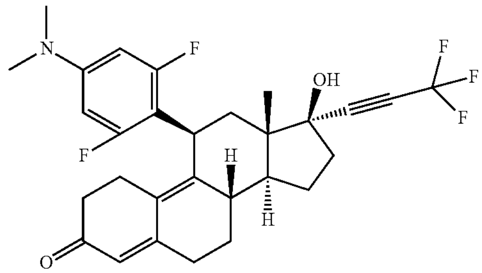 | 520.3 |
| | 508.4 |
| 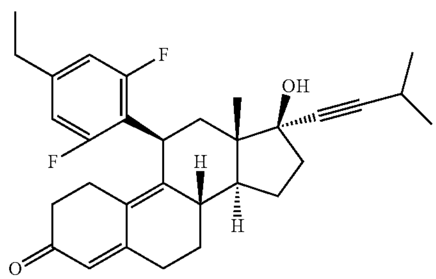 | 479.3 |
| | 508.4 |
| | 508.4 |

TABLE 1-continued

| Structure | Mass, [M + H]+ |
|---|---|
| 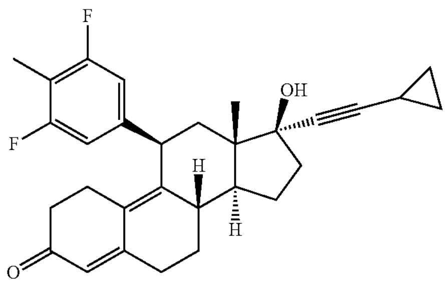 | 463.3 |
| 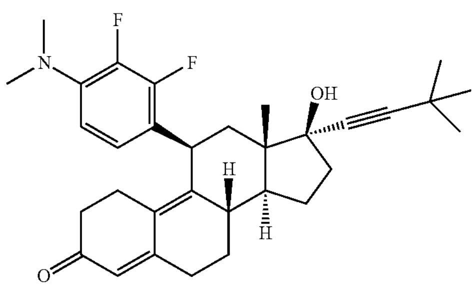 | 508.4 |
| 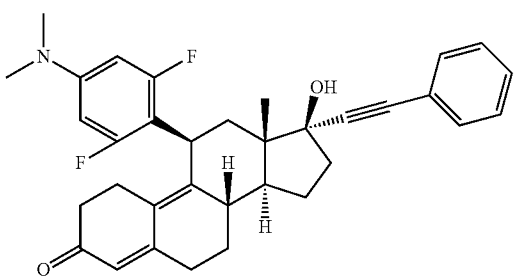 | 528.3 |
| 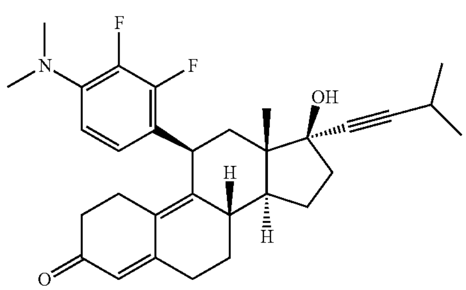 | 494.3 |
| 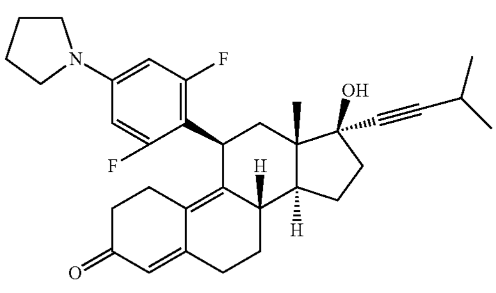 | 520.4 |

TABLE 1-continued

| Structure | Mass, [M + H]+ |
|---|---|
| 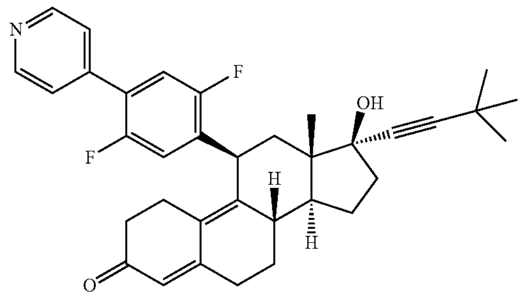 | 542.3 |
| 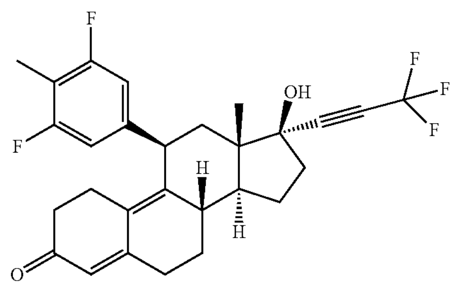 | 491.2 |
| 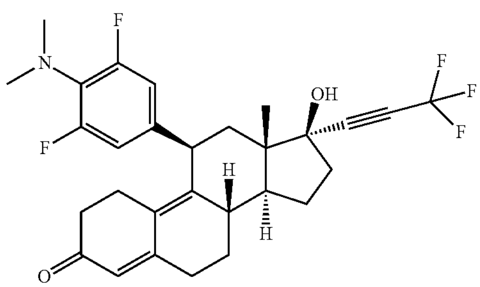 | 520.3 |
| 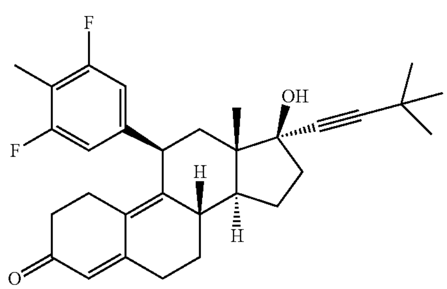 | 479.3 |
| 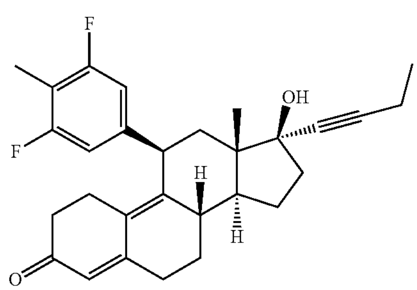 | 451.3 |

TABLE 1-continued

| Structure | Mass, [M + H]+ |
|---|---|
| 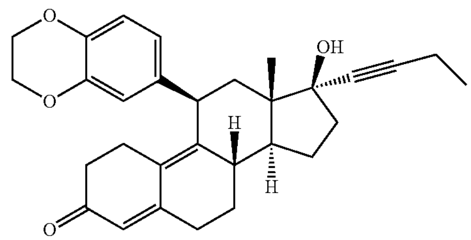 | 459.3 |
| 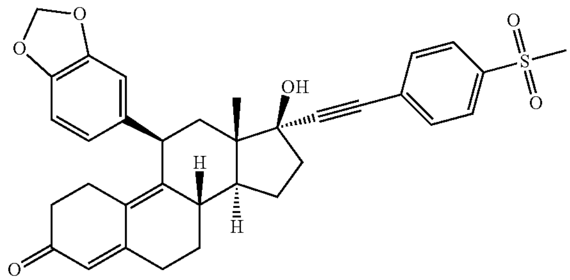 | 571.3 |
| 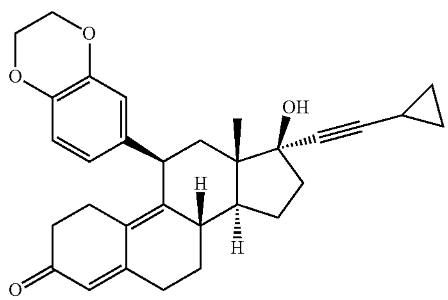 | 471.3 |
| 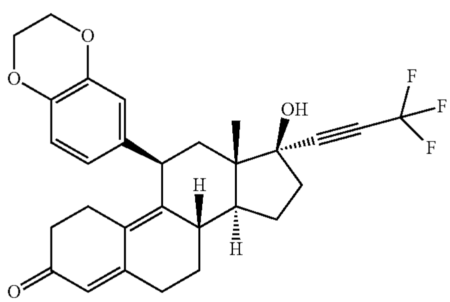 | 499.3 |
| 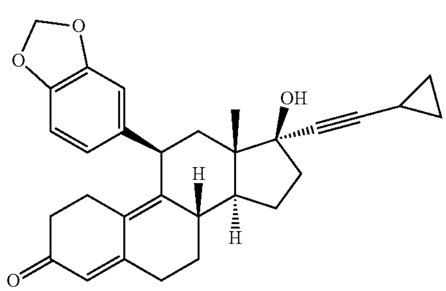 | 457.3 |

TABLE 1-continued

| Structure | Mass, [M + H]+ |
|---|---|
| 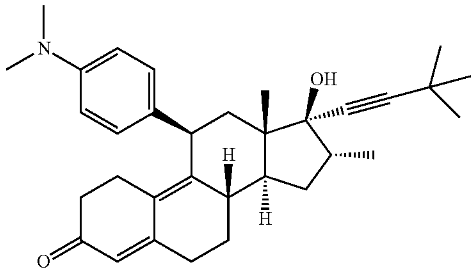 | 486.4 |
| 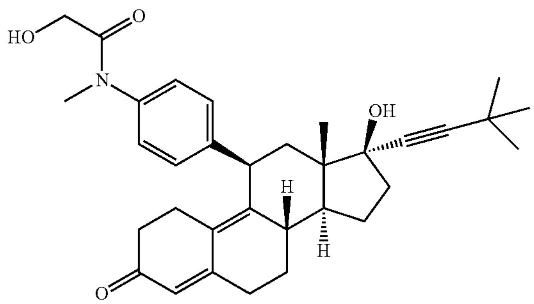 | 516.3 |
| 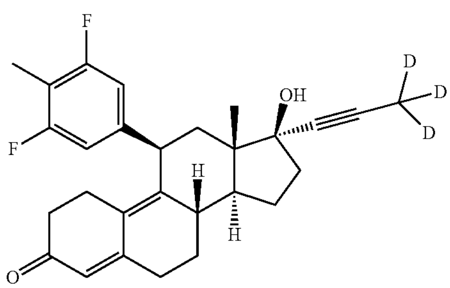 | 440.3 |
| 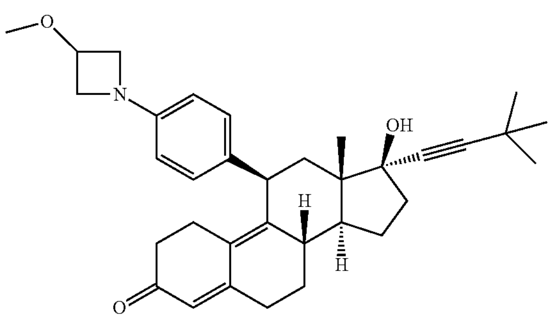 | 514.4 |
| 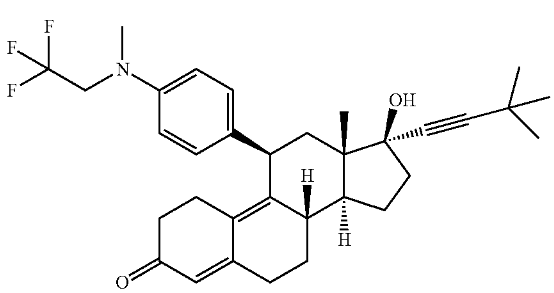 | 540.3 |

TABLE 1-continued

| Structure | Mass, [M + H]+ |
|---|---|
| 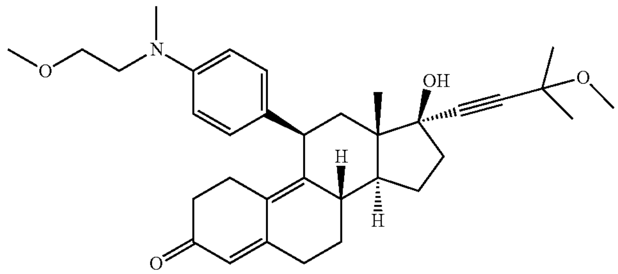 | 532.4 |
| 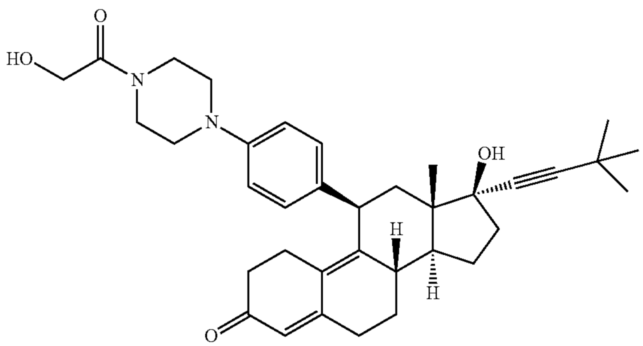 | 571.4 |
| 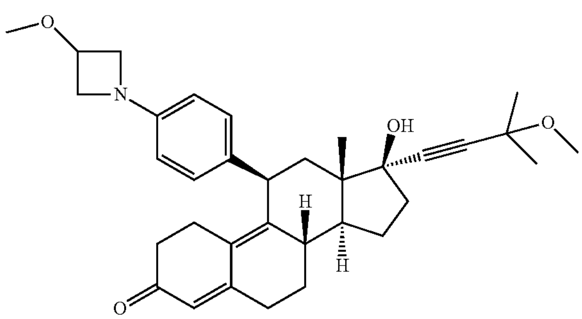 | 530.4 |
| 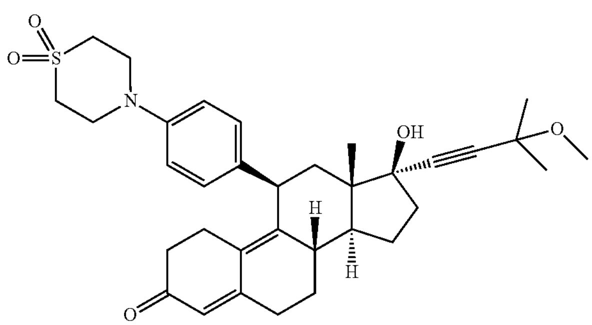 | 578.3 |
| 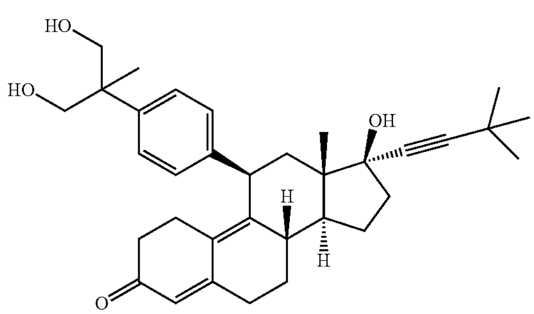 | 517.4 |

TABLE 1-continued

| Structure | Mass, [M + H]+ |
|---|---|
| 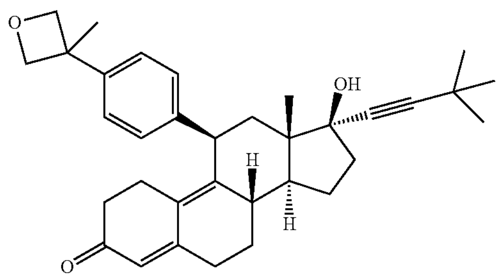 | 499.4 |
| 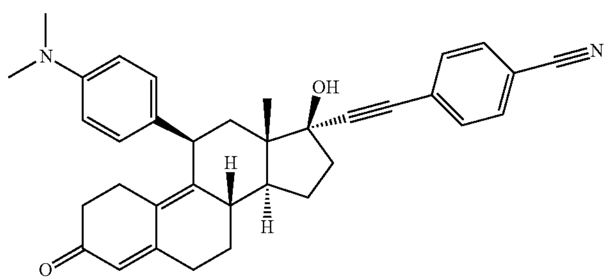 | 517.3 |
| | 501.4 |
| 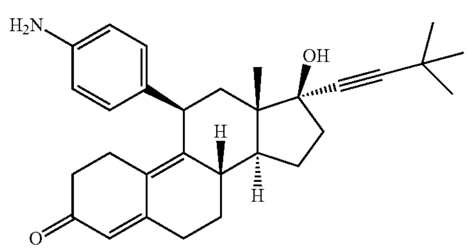 | 444.4 |
| | 501.4 |

TABLE 1-continued
| Structure | Mass, [M + H]+ |
|---|---|
| 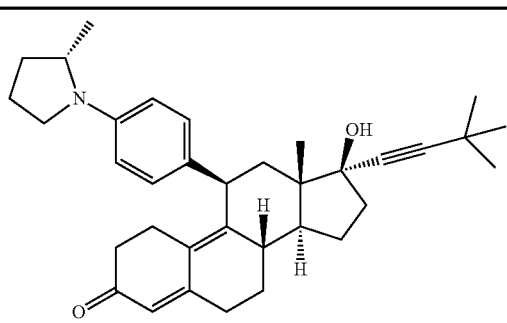 | 512.5 |
In some embodiments, the substituted steroidal derivative compound described in Formulas provided herein has a structure provided in Table 2.
TABLE 2
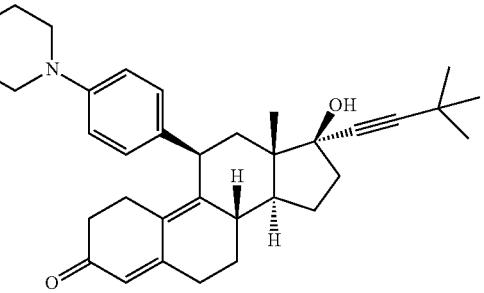
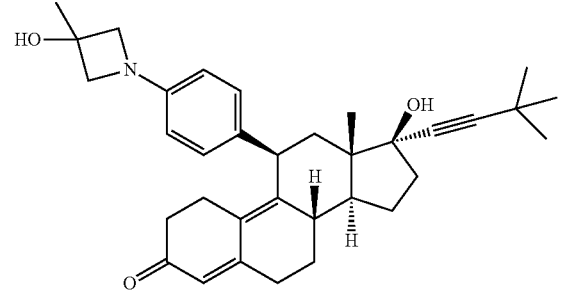
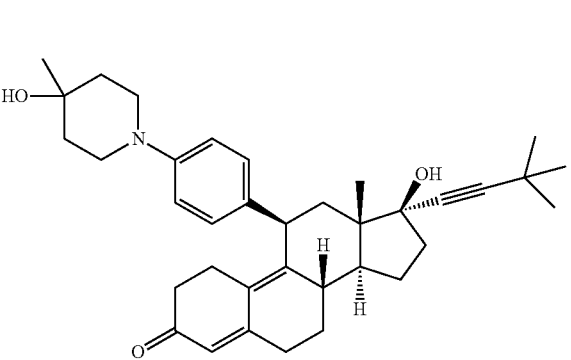
TABLE 2-continued
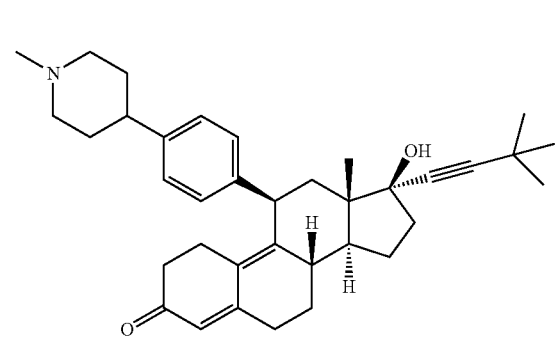
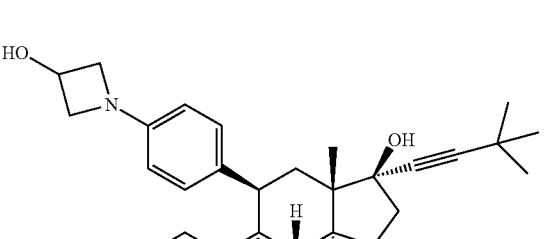
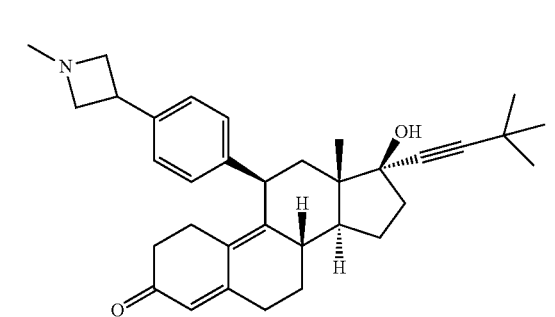

TABLE 2-continued

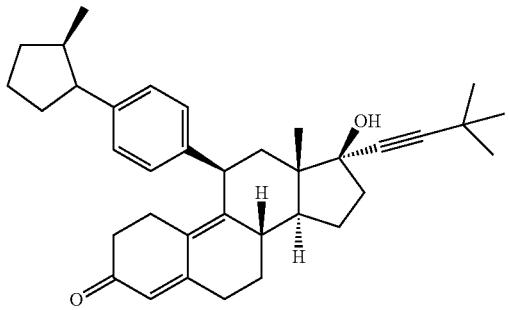

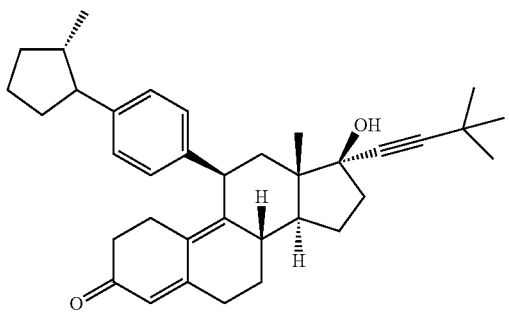

Preparation of the Substituted Steroidal Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the substituted steroidal derivative compounds described herein is P. H. Stahl & C. G. Wermuth "Handbook of Pharmaceutical Salts", Verlag Helvetica Chimica Acta, Zurich, 2002.

The substituted steroidal derivative compounds are prepared by the general synthetic route described below in Scheme 1.

Scheme 1

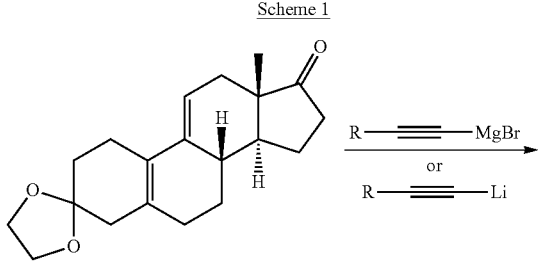

1

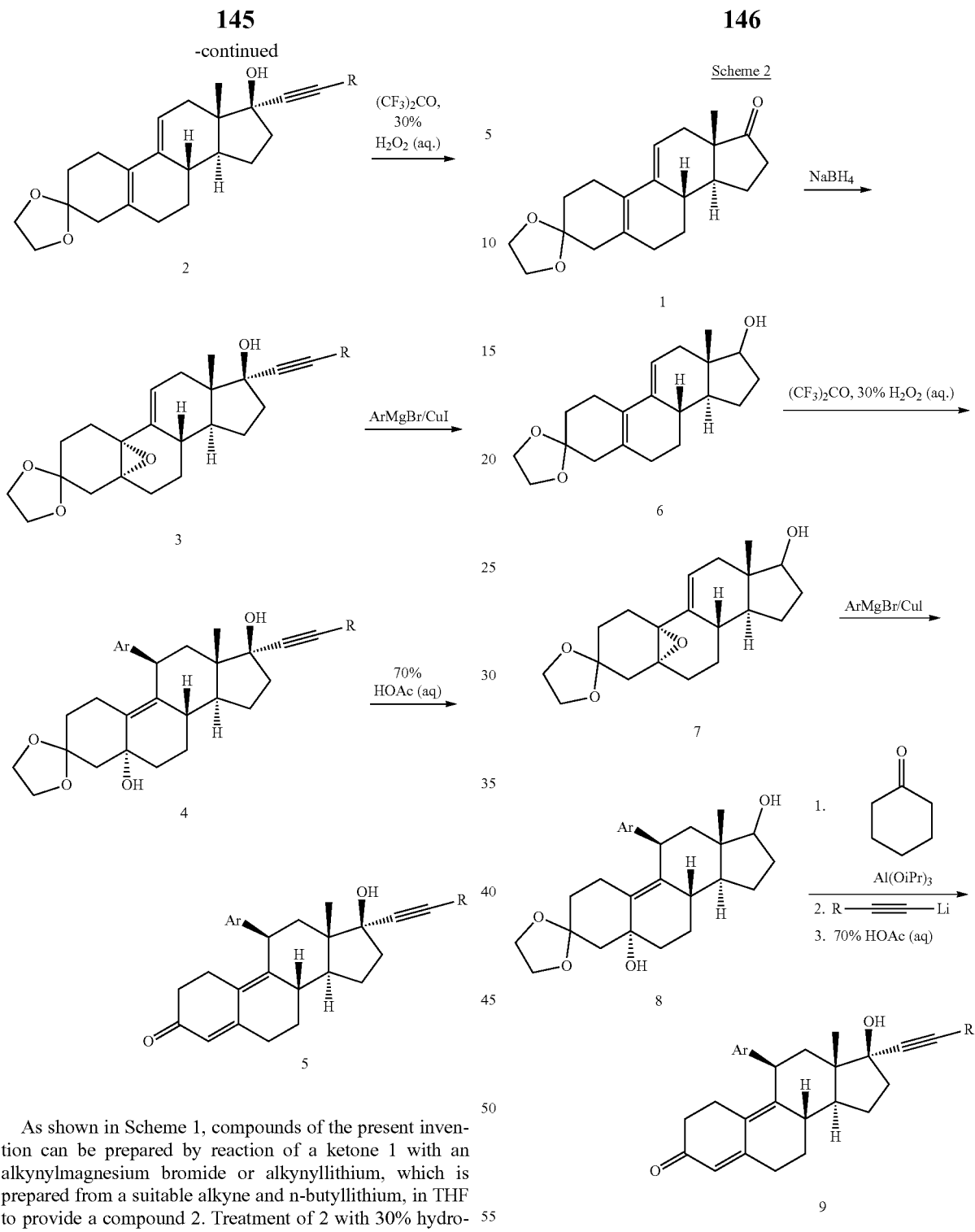

As shown in Scheme 1, compounds of the present invention can be prepared by reaction of a ketone 1 with an alkynylmagnesium bromide or alkynyllithium, which is prepared from a suitable alkyne and n-butyllithium, in THF to provide a compound 2. Treatment of 2 with 30% hydrogen peroxide and 1,1,1,3,3,3-hexafluoropropan-2-one trihydrate in the presence of Na$_2$HPO$_4$ in DCM produces an epoxide 3. Reaction of 3 with an arylmagnesium bromide in the presence of copper (I) iodide, followed by treatment with 70% acetic acid aq. solution gives compound 5. Arylmagnesium bromide is commercially available or prepared from a corresponding bromide or iodide using methods well known to those of ordinary skill in the art.

The substituted steroidal derivative compounds are prepared by the general synthetic route described below in Scheme 2.

Scheme 2 illustrates an alternative method for preparing compounds of the present invention. The ketone 1 can be reduced with NaBH$_4$ in a suitable solvent such as methanol to produce secondary alcohol 6, which was converted to an intermediate 8 by procedures similar to those described in Scheme 1 (from 2 to 4). The intermediate 8 can be oxidized with aluminum propan-2-olate in the presence of cyclohexanone to give a ketone, which can then be condensed with a suitable alkynyllithium, followed by treatment with 70% acetic acid aq. solution to give compound 9.

Pharmaceutical Compositions of the Substituted Steroidal Derivative Compounds

In certain embodiments, the substituted steroidal derivative compound as described herein is administered as a pure chemical. In other embodiments, the substituted steroidal derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one substituted steroidal derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of any of the Formulas provided herein, or a pharmaceutically acceptable salt thereof, and a pharmaceutically acceptable excipient.

In certain embodiments, the substituted steroidal derivative compound as described by any of the Formulas provided herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The dose of the composition comprising at least one substituted steroidal derivative compound as described herein differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Use of the Substituted Steroidal Derivative Compounds Glucocorticoid Receptor Modulators Mifepristone is a non-selective modulator of several nuclear receptors. Mifepristone has been referred to as a GR antagonist, a progesterone receptor (PR) antagonist, a GR partial agonist, an androgen receptor (AR) antagonist and an AR partial agonist in the scientific literature. The activity observed at multiple hormone receptors leads to various undesirable side effects and in some instances, the promotion of cancer. Thus, AR agonism is an undesirable feature for GR antagonists used in the treatment of cancer (e.g., AR positive or AR dependent cancers including "castration resistant" prostate cancer (CRPC), breast cancer, or ovarian cancer). Antagonists of GR that have minimized binding to other hormone receptors, such as the androgen receptor (AR), are needed to effectively treat the diseases described herein with reduced side effects.

Some embodiments provided herein describe compounds that are modulators of glucocorticoid receptors (GR). In some embodiments, the compounds alter the level and/or activity of GR. In some embodiments, the compounds described herein are GR inhibitors. In some embodiments, the GR inhibitors are GR antagonists. In some instances, glucocorticoid receptor antagonists bind to the receptor and prevent glucocorticoid receptor agonists from binding and eliciting GR mediated events, including transcription. Thus, in some embodiments, the compounds described herein inhibit GR transcriptional activation activity. In some embodiments, the compounds described herein are selective GR antagonists. In some embodiments, the compounds described herein are not GR agonists. In some embodiments, the compounds described herein are not GR partial agonists. In some embodiments, the GR inhibitors lessen cortisol activity in cells and make secondary therapeutic agents more effective.

GR antagonists are useful for treating or preventing weight gain (e.g., Olanzapine induced weight gain), uterine fibrosis, alcoholism, alcohol abuse disorders, cocaine dependence, bipolar depression, adrenal hypercortisolism, post-traumatic stress disorder, anxiety disorders, mood disorders, hyperglycemia, and to induce abortion.

In some embodiments, the GR inhibitors described herein are also androgen receptor (AR) signaling inhibitors. In certain embodiments, the AR signaling inhibitors are AR antagonists. In some instances, AR antagonists bind to AR and prevent AR agonists from binding and eliciting AR mediated events, including transcription. In other embodiments, the GR inhibitors are not androgen receptor (AR) signaling inhibitors. In these instances, the GR inhibitors do not significantly activate AR levels and/or activity.

In some embodiments, the GR inhibitors described herein have minimized binding to the androgen receptor (AR). In some embodiments, the compounds described herein are not AR agonists. In some embodiments, the compounds described herein are not partial AR agonists. In some embodiments, the compounds described herein have minimized partial AR agonism compared to mifepristone.

In some embodiments, the GR inhibitors described herein are not partial AR agonists or partial GR agonists.

In some embodiments, the GR inhibitors described herein do not modulate progesterone receptors. In some embodiments, the GR inhibitors described herein are not progesterone receptor (PR) inhibitors. In these instances, the GR inhibitors do not significantly activate PR levels and/or activity. In some embodiments, the GR inhibitors are not PR agonists. In some embodiments, the GR inhibitors are not PR partial agonists. In some embodiments, the GR inhibitors are not PR antagonists.

In some embodiments, the GR inhibitors (e.g., GR antagonists) are selective inhibitors. In some embodiments, use of the GR inhibitors in a patient does not cause or result in vaginal bleeding, cramping, nausea, vomiting, diarrhea, dizziness, back pain, weakness, tiredness, or combinations thereof. In certain embodiments, use of the GR inhibitors in a patient does not cause or result in vaginal bleeding. In certain embodiments, use of the GR inhibitors in a patient does not cause or result in cramping. In some embodiments, use of the GR inhibitors in a patient does not cause or result in allergic reactions, low blood pressure, loss of consciousness, shortness of breath, rapid heartbeat, or combinations thereof.

Methods of Treatment
Cancer

One embodiment provides a method of treating cancer in a subject in need thereof, comprising administering to the subject a compound of any of the Formulas provided herein, or a pharmaceutically acceptable salt thereof. In some embodiments, a GR inhibitor described herein is used in combination with a second therapeutic agent (e.g., an anti-cancer agent) for treating cancer. In some embodiments, the combination of the GR inhibitor with the second therapeutic agent (e.g., an anti-cancer agent) provides a more effective initial therapy for treating cancer compared to the second therapeutic agent (e.g., an anti-cancer agent) administered alone. In some embodiments, a GR inhibitor described herein is used in combination with one or more additional therapeutic agents (e.g., anti-cancer agents) for treating cancer. In some embodiments, the combination of the GR inhibitor with the one or more additional therapeutic agents (e.g., an anti-cancer agents) provides a more effective initial therapy for treating cancer compared to the one or more therapeutic agents (e.g., an anti-cancer agents) administered alone.

In some embodiments, the cancer is chemoresistant cancer, radio resistant cancer, or refractory cancer. In some embodiments, the cancer is relapsed cancer, persistent cancer, or recurrent cancer. Another embodiment provided herein describes a method of reducing incidences of cancer recurrence. Also provided here in some embodiments, is a method of for treating a chemo-resistant cancer.

Prostate Cancer

Prostate cancer is the second most common cause of cancer death in men in the United States, and approximately one in every six American men will be diagnosed with the disease during his lifetime. Treatment aimed at eradicating the tumor is unsuccessful in 30% of men.

One embodiment provides a method of treating prostate cancer in a subject in need thereof, comprising administering to the subject a compound of any of the Formulas provided herein, or a pharmaceutically acceptable salt thereof. In some embodiments, a GR inhibitor described herein is used in combination with a second therapeutic agent (e.g., an anti-cancer agent) for treating prostate cancer. In some embodiments, the combination of the GR inhibitor with the second therapeutic agent (e.g., an anti-cancer agent) provides a more effective initial therapy for treating prostate cancer compared to the second therapeutic agent (e.g., an anti-cancer agent) administered alone. In some embodiments, a GR inhibitor described herein is used in combination with one or more additional therapeutic agents (e.g., anti-cancer agents) for treating prostate cancer. In some embodiments, the combination of the GR inhibitor with the one or more additional therapeutic agents (e.g., an anti-cancer agents) provides a more effective initial therapy for treating prostate cancer compared to the one or more therapeutic agents (e.g., an anti-cancer agents) administered alone.

In some embodiments, the prostate cancer is chemoresistant cancer, radio resistant cancer, antiandrogen resistant, or refractory cancer. In some embodiments, the prostate cancer is relapsed cancer, persistent cancer, or recurrent cancer.

In some embodiments, the prostate cancer is acinar adenocarcinoma, atrophic carcinoma, foamy carcinoma, colloid carcinoma, or signet ring carcinoma. In some embodiments, the prostate cancer is ductal adenocarcinoma, transitional cell cancer, urothelial cancer, squamous cell cancer, carcinoid cancer, small cell cancer, sarcoma cancer, or sarcomatoid cancer. In some embodiments, the prostate cancer is metastatic castration-resistant prostate cancer, doubly-resistant prostate cancer, castration-resistant prostate cancer, hormone-resistant prostate cancer, androgen-independent, or androgen-refractory cancer.

In some instances, antiandrogens are useful for the treatment of prostate cancer during its early stages. In some instances, prostate cancer cells depend on androgen receptor (AR) for their proliferation and survival. Some prostate cancer patients are physically castrated or chemically castrated by treatment with agents that block production of testosterone (e.g. GnRH agonists), alone or in combination with antiandrogens, which antagonize effects of any residual testosterone.

In some instances, prostate cancer advances to a hormone-refractory state in which the disease progresses despite continued androgen ablation or antiandrogen therapy. The hormone-refractory state to which most patients eventually progresses in the presence of continued androgen ablation or anti-androgen therapy is known as "castration resistant" prostate cancer (CRPC). CRPC is associated with an overexpression of AR. AR is expressed in most prostate cancer cells and overexpression of AR is necessary and sufficient for androgen-independent growth of prostate cancer cells. Failure in hormonal therapy, resulting from development of androgen-independent growth, is an obstacle for successful management of advanced prostate cancer.

While a small minority of CRPC does bypass the requirement for AR signaling, the vast majority of CRPC, though frequently termed "androgen independent prostate cancer" or "hormone refractory prostate cancer," retains its lineage dependence on AR signaling.

Recently approved therapies that target androgen receptor (AR) signaling such as abiraterone and enzalutamide have been utilized for treating CRPC. Despite these successes, sustained response with these agents is limited by acquired resistance which typically develops within 6-12 months. Doubly resistant prostate cancer is characterized in that tumor cells have become castration resistant and overexpress AR, a hallmark of CRPC. However, cells remain resistant when treated with second generation antiandrogens. Doubly resistant prostate cancer cells are characterized by a lack of effectiveness of second generation antiandrogens in inhibiting tumor growth.

As discussed above, resistant prostate cancer (e.g., doubly resistant and castration resistant prostate cancers) occurs when cancer cells overexpress androgen receptors (AR). AR target gene expression is inhibited when the cells are treated with a second generation antiandrogen. In some instances, increased signaling through the glucocorticoid receptor (GR) compensates for inhibition of androgen receptor signaling in resistant prostate cancer. Double resistant prostate cancer develops when expression of a subset of those AR target genes is restored. In some instances, GR activation is responsible for this target gene activation. In some embodiments, GR transcription is activated in patients susceptible to or suffering from resistant prostate cancer (e.g., doubly resistant and castration resistant prostate cancers). In some instances, GR upregulation in cancer cells confers resistance to antiandrogens.

Some embodiments provided herein describe the use of the GR inhibitors for treating prostate cancer in a subject in need thereof, including doubly resistant prostate cancer and castration resistant prostate cancer. In some embodiments, the subject in need has elevated tumor GR expression. In some embodiments, the GR inhibitor is also an AR signaling inhibitor or antiandrogen.

In some embodiments, the GR inhibitor is used in combination with a second therapeutic agent. In some embodiments, the GR inhibitor is used in combination with one or more additional therapeutic agents. In some embodiments, the second or additional agent is an anti-cancer agent. In certain embodiments, the anti-cancer agent is useful for AR positive or AR negative prostate cancer.

In some embodiments, the second or additional agent is an AR signaling inhibitor or antiandrogen. In certain embodiments, the AR signaling inhibitor is an AR antagonist. In some embodiments, the second or additional therapeutic agent is selected from finasteride, dutasteride, alfatradiol, cyproterone acetate, spironolactone, danazol, gestrinone, ketoconazole, abiraterone acetate, enzalutamide, ARN-509, danazol, gestrinone, danazol, simvastatin, aminoglutethimide, atorvastatin, simvastatin, progesterone, cyproterone acetate, medroxyprogesterone acetate, megestrol acetate, chlormadinone acetate, spironolactone, drospirenone, estradiol, ethinyl estradiol, diethylstilbestrol, conjugated equine estrogens, buserelin, deslorelin, gonadorelin, goserelin, histrelin, leuprorelin, nafarelin, triptorelin, abarelix, cetrorelix, degarelix, ganirelix, or any combinations or any salts thereof. In some embodiments, the second or additional therapeutic agent is selected from flutamide, nilutamide, bicalutamide, enzalutamide, apalutamide, cyproterone acetate, megestrol acetate, chlormadinone acetate, spironolactone, canrenone, drospirenone, ketoconazole, topilutamide, cimetidine, or any combinations or any salts thereof. In some embodiments, the AR signaling inhibitor is 3,3'-diindolylmethane (DIM), abiraterone acetate, ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, turosteride, or any combinations thereof. In some embodiments, the AR signaling inhibitor is flutamide, nilutamide, bicalutamide, or megestrol. In some embodiments, the AR signaling inhibitor is ARN-509. In other embodiments, the AR signaling inhibitor is enzalutamide.

In some embodiments, the anti-cancer agent is mitoxantrone, estramustine, etoposide, vinblastine, carboplatin, vinorelbine, paclitaxel, daunomycin, darubicin, epirubicin, docetaxel, cabazitaxel, or doxorubicin. In some embodiments, the anti-cancer agent is paclitaxel, daunomycin, darubicin, epirubicin, docetaxel, cabazitaxel, or doxorubicin. In certain embodiments, the anti-cancer agent is docetaxel.

Breast Cancer

Breast cancer is the second leading cause of cancer among women in the United States. Triple-negative breast cancers are among the most aggressive and difficult to treat of all the breast cancer types. Triple-negative breast cancer is a form of the disease in which the three receptors that fuel most breast cancer growth—estrogen, progesterone and the HER-2—are not present. Because the tumor cells lack these receptors, treatments that target estrogen, progesterone and HER-2 are ineffective. Approximately 40,000 women are diagnosed with triple-negative breast cancer each year. It is estimated that more than half of these women's tumor cells express significant amounts of GR.

In some instances, GR expression is associated with a poor prognosis in estrogen receptor (ER)-negative early stage breast cancer. In some instances, GR activation in triple-negative breast cancer cells initiates an anti-apoptotic gene expression profile that is associated with inhibiting chemotherapy-induced tumor cell death. GR activity in these cancer cells correlate with chemotherapy resistance and increased recurrence of cancer.

Provided herein in some embodiments are methods of treating breast cancer, the method comprising administering to a subject in need thereof a compound of any of the Formulas provided herein, or a pharmaceutically acceptable salt thereof. In some embodiments, a GR inhibitor described herein is used in combination with a second therapeutic agent (e.g., a chemotherapeutic agent) for treating breast cancer. In some embodiments, the combination of the GR inhibitor with the second therapeutic agent (e.g., a chemotherapeutic agent) provides a more effective initial therapy for treating breast cancer compared to the second therapeutic agent (e.g., a chemotherapeutic agent) administered alone. In some embodiments, a GR inhibitor described herein is used in combination with one or more additional therapeutic agents (e.g., anti-cancer agents) for treating breast cancer. In some embodiments, the combination of the GR inhibitor with the one or more additional therapeutic agents (e.g., an anti-cancer agents) provides a more effective initial therapy for treating breast cancer compared to the one or more therapeutic agents (e.g., an anti-cancer agents) administered alone.

In some embodiments, the breast cancer is chemoresistant cancer, radio resistant cancer, or refractory cancer. In some embodiments, the breast cancer is relapsed cancer, persistent cancer, or recurrent cancer. Breast cancers may include, but are not limited to, ductal carcinoma, invasive ductal carcinoma, tubular carcinoma of the breast, medullary carcinoma of the breast, mecinous carcinoma of the breast, papillary carcinoma of the breast, cribriform carcinoma of the breast, invasive lobular carcinoma, inflammatory breast cancer, lobular carcinoma in situ, male breast cancer, Paget disease of the nipple, phyllodes tumor of the breast, recurrent and metastatic breast cancer, triple-negative breast cancer, or combinations thereof.

In some embodiments, the breast cancer is recurrent and metastatic breast cancer, triple-negative breast cancer, or combinations thereof. In some embodiments, the breast cancer is chemoresistant triple-negative breast cancer or estrogen receptor (ER) negative breast cancer. In some embodiments, the breast cancer is chemoresistant triple-negative breast cancer. In some embodiments, the breast cancer is estrogen receptor (ER) negative breast cancer. In some embodiments, the breast cancer is GR+ triple-negative breast cancer. In some embodiments, the breast cancer is GR+ estrogen receptor (ER) negative breast cancer.

Some embodiments provided herein describe the use of GR inhibitors for treating breast cancer in a patient, including triple negative breast cancer or ER negative breast cancer. In some embodiments, GR inhibitors inhibit the anti-apoptotic signaling pathways of GR and increase the cytotoxic efficiency of secondary chemotherapeutic agents.

In some embodiments, the GR inhibitors described herein enhance the efficacy of chemotherapy in breast cancer patients, such as triple negative breast cancer patients. In some embodiments, the breast cancer patient has elevated tumor GR expression.

In some embodiments, a GR inhibitor described herein is used in combination with a second therapeutic agent, such as chemotherapy or immunotherapy. In some embodiments, a GR inhibitor described herein is used in combination with one or more additional therapeutic agents. In some embodiments, the second or additional chemotherapeutic agent is cisplatin, carboplatin, cyclophosphamide, capecitabine, gemcitabine, paclitaxel, nab-paclitaxel, altretamine, docetaxel, epirubicin, melphalan, methotrexate, mitoxantrone, ixabepilone, ifosfamide, irinotecan, eribulin, etoposide, doxorubicin, liposomal doxorubicin, camptothecin, pemetrexed, topotecan, vinorelbine, daunorubicin, fluorouracil, mitomycin, thiotepa, vincristine, everolimus, veliparib, glembatumumabg vedotin, pertuzumab, trastuzumab, or any combinations or any salts thereof. In some embodiments, the second or additional therapeutic agent is an anti-PD-L1 agent. In certain embodiments, the anti-PD-L1 agent is MPDL3280A or avelumab. In some embodiments, the second or additional therapeutic agent is an anti-PD1 agent. In certain embodiments, the anti-PD1 agent is nivolumab or permbrolizumab.

Some embodiments provided herein describe methods of treating estrogen positive breast cancer. In some instances, estrogen positive breast cancer patients become resistant to estrogen receptor modulators. In some embodiments, the GR inhibitors described herein enhance the efficacy of estrogen receptor modulators in estrogen positive breast cancer patients. In some embodiments, the breast cancer patient has elevated tumor GR expression. In some embodiments, a GR inhibitor described herein is used in combination with an estrogen receptor modulator. In some embodiments, the estrogen receptor modulator is tamoxifen, raloxifene, toremifene, tibolone, fulvestrant, lasofoxifene, clomifene, ormeloxifene, or ospemifene. In some embodiments, the estrogen receptor modulator is tamoxifen, raloxifene, toremifene, tibolone, or fulvestrant. In some embodiments, the estrogen receptor modulator is tamoxifen, raloxifene, or toremifene. In certain embodiments, the estrogen receptor modulator is tamoxifen.

Ovarian Cancer

Ovarian cancer is the leading cause of death from gynecologic malignancies. Some ovarian cancers (e.g., high grade serous ovarian cancer) are initially sensitive to platinum-based therapy, but relapse rates remain high.

One embodiment provides a method of treating ovarian cancer in a patient in need thereof, comprising administering to the patient a compound of any of the Formulas provided herein, or a pharmaceutically acceptable salt thereof. In some embodiments, the patient has elevated tumor GR expression. In some embodiments, a GR inhibitor described herein is used in combination with a second therapeutic agent (e.g., a chemotherapeutic agent) for treating ovarian cancer. In some embodiments, the combination of the GR inhibitor with the second therapeutic agent (e.g., a chemotherapeutic agent) provides a more effective initial therapy for treating ovarian cancer compared to the second therapeutic agent (e.g., a chemotherapeutic agent) administered alone. In some embodiments, a GR inhibitor described herein is used in combination with one or more additional therapeutic agents (e.g., anti-cancer agents) for treating ovarian cancer. In some embodiments, the combination of the GR inhibitor with the one or more additional therapeutic agents (e.g., an anti-cancer agents) provides a more effective initial therapy for treating ovarian cancer compared to the one or more therapeutic agents (e.g., an anti-cancer agents) administered alone.

In some instances, GR activation increases resistance to chemotherapy in ovarian cancer (e.g., high-grade serous ovarian cancer). In some instances, GR activation significantly inhibits chemotherapy induced apoptosis in ovarian cancer cells. Provided herein in some embodiments are methods of treating ovarian cancer in a subject, the method comprising treating the subject with a GR inhibitor (e.g., GR antagonist) to improve sensitivity to chemotherapy. In some embodiments, the ovarian cancer has become resistant to chemotherapy. In some embodiments, the ovarian cancer cells are resistant to cisplatin, paclitaxel, carboplatin, gemcitabine, alone or in combination. In some embodiments, the GR inhibitor or antagonist reverses the cell survival effect.

Ovarian cancers may include, but are not limited to, epithelial ovarian cancers, such as serous epithelial ovarian cancer, endometrioid epithelial ovarian cancer, clear cell epithelial ovarian cancer, mucinous epithelial ovarian cancer, undifferentiated or unclassifiable epithelial ovarian cancer, refractory ovarian cancer, sex cord-stromal tumors, Sertoli and Sertoli-Leydig cell tumors, germ cell tumors, such as dysgerminoma and nondysgerminomatous tumors, Brenner tumors, primary peritoneal carcinoma, fallopian tube cancer, or combinations thereof.

In some embodiments, the GR inhibitor is used in combination with at least a second therapeutic agent, such as chemotherapy or immunotherapy. In some embodiments, the GR inhibitor is used in combination with one or more additional therapeutic agents. In some embodiments, the second or additional chemotherapeutic agent is cisplatin, carboplatin, cyclophosphamide, capecitabine, gemcitabine, paclitaxel, nab-paclitaxel, altretamine, docetaxel, epirubicin, melphalan, methotrexate, mitoxantrone, ixabepilone, ifosfamide, irinotecan, eribulin, etoposide, doxorubicin, liposomal doxorubicin, camptothecin, pemetrexed, topotecan, vinorelbine, daunorubicin, fluorouracil, mitomycin, thiotepa, vincristine, everolimus, veliparib, glembatumumab vedotin, pertuzumab, trastuzumab, or any combinations or any salts thereof. In some embodiments, the second or additional chemotherapeutic agent is gemcitabine. In some embodiments, the second or additional chemotherapeutic agent is carboplatin. In some embodiments, the second or additional chemotherapeutic agent is cisplatin. In some embodiments, the second or additional agent is paclitaxel. In some embodiments, the GR inhibitor is used in combination with gemcitabine and carboplatin. In some embodiments, the GR inhibitor is used in combination with carboplatin and cisplatin. In some embodiments, the second or additional therapeutic agent is an anti-PD-L1 agent. In certain embodiments, the anti-PD-L1 agent is MPDL3280A or avelumab. In some embodiments, the second or additional therapeutic agent is an anti-PD1 agent. In certain embodiments, the anti-PD1 agent is nivolumab or permbrolizumab.

Non-Small Cell Lung Cancer

One embodiment provides a method of treating non-small cell lung cancer (NSCLC) in a patient in need thereof, comprising administering to the patient a compound of any of the Formulas provided herein, or a pharmaceutically acceptable salt thereof. In some embodiments, the patient has elevated tumor GR expression. In some embodiments, a GR inhibitor described herein is used in combination with a second therapeutic agent (e.g., a chemotherapeutic agent) for treating NSCLC. In some embodiments, the combination of the GR inhibitor with the second therapeutic agent (e.g., a chemotherapeutic agent) provides a more effective initial therapy for treating NSCLC compared to the second therapeutic agent (e.g., a chemotherapeutic agent) administered alone. In some embodiments, a GR inhibitor described herein is used in combination with one or more additional therapeutic agents (e.g., anti-cancer agents) for treating NSCLC. In some embodiments, the combination of the GR inhibitor with the one or more additional therapeutic agents (e.g., an anti-cancer agents) provides a more effective initial therapy for treating NSCLC compared to the one or more therapeutic agents (e.g., an anti-cancer agents) administered alone.

In some embodiments, the GR inhibitor is used in combination with at least a second therapeutic agent, such as a chemotherapeutic agent or immunotherapy. In some embodiments, the GR inhibitor is used in combination with one or more additional therapeutic agents. In some embodiments, the second or additional chemotherapeutic agent is cisplatin, carboplatin, cyclophosphamide, capecitabine, gemcitabine, paclitaxel, nab-paclitaxel, altretamine, docetaxel, epirubicin, melphalan, methotrexate, mitoxantrone, ixabepilone, ifosfamide, irinotecan, eribulin, etoposide, doxorubicin, liposomal doxorubicin, camptothecin, pemetrexed, topotecan, vinorelbine, vinblastine, daunorubicin, fluorouracil, mitomycin, thiotepa, vincristine, everolimus, veliparib, glembatumumab vedotin, pertuzumab, trastuzumab, or any combinations or any salts thereof. In some embodiments, the second or additional chemotherapeutic agent is gemcitabine. In some embodiments, the second or additional chemotherapeutic agent is carboplatin. In some embodiments, the second or additional chemotherapeutic agent is cisplatin. In some embodiments, the second or additional agent is paclitaxel. In some embodiments, the GR inhibitor is used in combination with gemcitabine and carboplatin. In some embodiments, the GR inhibitor is used in combination with carboplatin and cisplatin. In some embodiments, the second or additional therapeutic agent is an anti-PD-L1 agent. In certain embodiments, the anti-PD-L1 agent is MPDL3280A or avelumab. In some embodiments, the second or additional therapeutic agent is an anti-PD1 agent. In certain embodiments, the anti-PD1 agent is nivolumab or permbrolizumab.

Hypercortisolism/Cushing's Disease

One embodiment provides a method of treating hypercortisolism or Cushing's disease in a patient in need thereof, comprising administering to the patient a compound of any of the Formulas provided herein, or a pharmaceutically acceptable salt thereof.

Types of Cushing's disease include, but are not limited to, recurrent Cushing's disease, refractory Cushing's disease, persistent Cushing's disease, endogenous Cushing's disease, spontaneous hypercortisolism, Adrenocorticotropic hormone dependent, Adrenocorticotropic hormone independent, or combinations thereof.

Causes of hypercortisolism may include, but are not limited to, prolonged exposure to cortisol, a tumor that produces excessive cortisol, a tumor that results in the excess production of cortisol, or combinations thereof.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

The substituted steroidal derivative compounds are prepared by the general synthetic route described in Schemes 1 and 2.

Example 1. (8S,11R,13S,14S,17S)-11-(4-(Dimethylamino)phenyl)-17-(3,3-dimethylbut-1-yn-1-yl)-17-hydroxy-13-methyl-1,2,6,7,8,11,12,13,14,15,16,17-dodecahydro-3H-cyclopenta[a]phenanthren-3-one

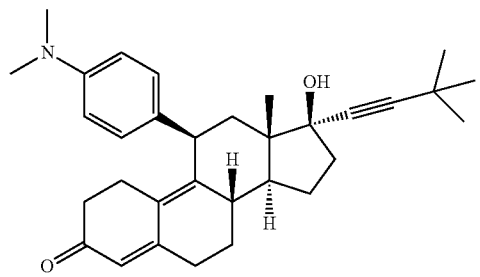

Step A: (8S,13S,14S,17S)-17-(3,3-Dimethylbut-1-yn-1-yl)-13-methyl-1,2,4,6,7,8,12,13,14,15,16,17-dodecahydrospiro[cyclopenta[a]phenanthrene-3,2'-[1,3]dioxolan]-17-ol

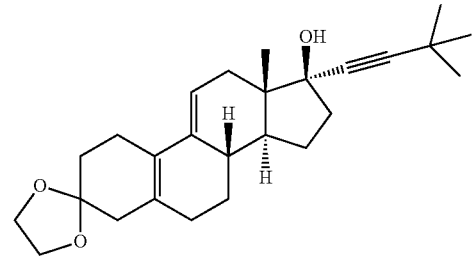

To a solution of 3,3-dimethylbut-1-yne (3.34 g, 40.7 mmol) in THF (85 mL) at −78° C. was added dropwise n-butyllithium (1.6 N, 24.6 mL, 39.4 mmol). After it was stirred at −78° C. for 25 min, a solution of (8S,13S,14S)-13-methyl-1,4,6,7,8,12,13,14,15,16-decahydrospiro[cyclopenta[a]phenanthrene-3,2'-[1,3]dioxolan]-17(2H)-one (8.0 g, 25.4 mmol) in THF (100 ml) was added slowly. The mixture was stirred at −78° C. for 17 min and then at rt for 40 min. The reaction mixture was quenched by slow addition to aq. NH$_4$Cl solution and concentrated to remove the majority of THF. The residue was extracted with EtOAc (400 ml). The organic phase was washed with brine and dried over anhydrous Na$_2$SO$_4$. The mixture was then concentrated under reduced pressure and the crude residue was purified by silica gel chromatography, eluting with 5-10% EtOAc in hexanes over 40 min to provide the title compound, (7.7 g, 18.9 mmol, 74% yield) as a white solid.

Step B: (5'R,8'S,10'R,13'S,14'S,17'S)-17'-(3,3-Dimethylbut-1-yn-1-yl)-13'-methyl-1',2',7',8',12',13',14',15',16',17'-decahydro-4'H,6'H-spiro[[1,3]dioxolane-2,3'-[5,10]epoxycyclopenta[a]phenanthren]-17'-ol

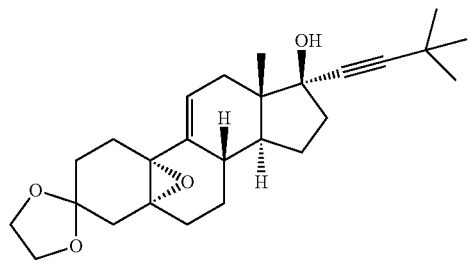

To a solution of (8S,13S,14S,17S)-17-(3,3-dimethylbut-1-yn-1-yl)-13-methyl-1,2,4,6,7,8,12,13,14,15,16,17-dodecahydrospiro[cyclopenta[a]phenanthrene-3,2'-[1,3]dioxolan]-17-ol (Example 1, Step A) (7.5 g, 18.9 mmol) in DCM (120 mL) at 0° C. (ice bath) was added Na$_2$HPO$_4$ (5.37 g, 37.8 mmol), followed by CF$_3$COCF$_3$·3H$_2$O (2.6 mL, 18.9 mmol) and H$_2$O$_2$ (35% aq) (4.36 mL, 56.7 mmol). The mixture was stirred at 0° C. for 10 min and then at rt for 2 h. Aq. Na$_2$S$_2$O$_3$ solution was added, the mixture was stirred at rt for 30 min and extracted with EtOAc. The organic phase was washed with brine and dried over anhydrous Na$_2$SO$_4$. The mixture was then concentrated under reduced pressure and the crude residue was purified by silica gel chromatography, eluting with 10-15% EtOAc in hexanes over 90 min to provide the title compound, (6.9 g, 16.7 mmol, 88% yield) as a white solid.

Step C: (5R,8S,11R,13S,14S,17S)-11-(4-(Dimethylamino)phenyl)-17-(3,3-dimethylbut-1-yn-1-yl)-13-methyl-1,2,6,7,8,11,12,13,14,15,16,17-dodecahydrospiro[cyclopenta[a]phenanthrene-3,2'-[1,3]dioxolane]-5,17(4H)-diol

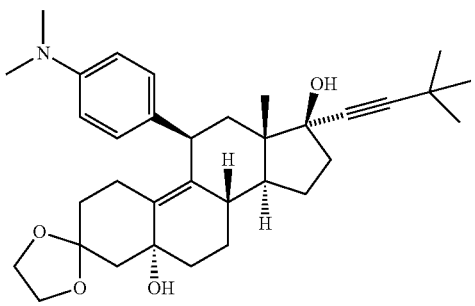

A mixture of (5'R,8'S,10'R,13'S,14'S,17'S)-17'-(3,3-dimethylbut-1-yn-1-yl)-13'-methyl-1',2',7',8',12',13',14',15',16',17'-decahydro-4'H,6'H-spiro[[1,3]dioxolane-2,3'-[5,10]epoxycyclopenta[a]phenanthren]-17'-ol (Step B) (80 mg, 0.19 mmol) and copper (I) iodide (36.9 mg, 0.19 mmol) in THF (3 mL) was degassed with argon. After cooling in an ice bath, (4-(dimethylamino) phenyl) magnesium bromide (3.1 mL, 1.55 mmol) (0.5 M in THF) was added dropwise. The resulting solution was maintained at rt for 1 h, then quenched with NH$_4$Cl solution and extracted with EtOAc. The organic phase was washed with brine and dried over anhydrous Na$_2$SO$_4$. The mixture was then concentrated under reduced pressure and the crude residue was purified by silica gel chromatography to provide the title compound, (90 mg, 0.17 mmol, 89% yield) as a white solid.

Step D: (8S,11R,13S,14S,17S)-11-(4-(Dimethylamino)phenyl)-17-(3,3-dimethylbut-1-yn-1-yl)-17-hydroxy-13-methyl-1,2,6,7,8,11,12,13,14,15,16,17-dodecahydro-3H-cyclopenta[a]phenanthren-3-one

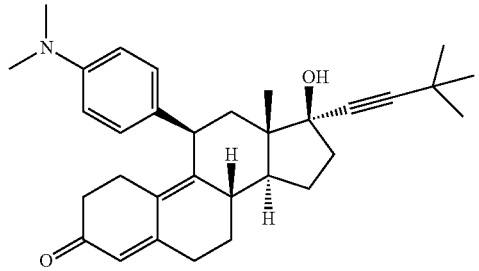

A solution (5R,8S,11R,13S,14S,17S)-11-(4-(dimethylamino)phenyl)-17-(3,3-dimethylbut-1-yn-1-yl)-13-methyl-1,2,6,7,8,11,12,13,14,15,16,17-dodecahydrospiro[cyclopenta[a]phenanthrene-3,2'-[1,3]dioxolane]-5,17(4H)-diol (Step C) (90 mg, 0.17 mmol) in 1:2 acetic acid/water (16.5 mL) was stirred at 65° C. for 90 min. The reaction mixture was cooled to rt and slowly added to aq. NaHCO$_3$ solution. After extraction with EtOAc, the organic phase was washed with brine, dried over anhydrous Na$_2$SO$_4$ and concentrated under reduced pressure. The crude residue was purified by silica gel chromatography to provide the title compound (54 mg, 0.12 mmol, 70% yield) as a pale yellow solid. $^1$H NMR (400 MHz, CDCl$_3$) δ ppm 7.03 (2H, m, J=8.59 Hz), 6.67 (2H, m, J=8.59 Hz), 5.77 (1H, s), 4.36 (1H, br d, J=6.25 Hz), 2.93 (6H, s), 2.76 (1H, s), 2.59 (2H, dd, J=7.42, 3.12 Hz), 2.27-2.49 (6H, m), 2.17-2.25 (1H, m), 1.86-2.06 (2H, m), 1.64-1.78 (3H, m), 1.47 (1H, br s), 1.34 (1H, br dd, J=11.71, 5.66 Hz), 1.20-1.29 (9H, s), 0.56 (3H, s). m/z (ESI, +ve ion) 472.4 (M+H)$^+$.

Example 2. (8S,11R,13S,14S,17S)-11-(4-(Dimethylamino)phenyl)-17-hydroxy-13-methyl-17-(pyridin-2-ylethynyl)-1,2,6,7,8,11,12,13,14,15,16,17-dodecahydro-3H-cyclopenta[a]phenanthren-3-one

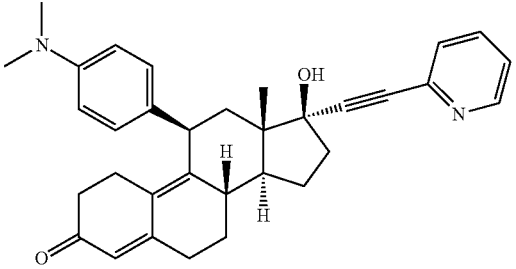

Step A. (8S,13S,14S,17S)-13-Methyl-1,2,4,6,7,8,12, 13,14,15,16,17-dodecahydrospiro[cyclopenta[a] phenanthrene-3,2'-[1,3]dioxolan]-17-ol and (8S,13S, 14S,17R)-13-methyl-1,2,4,6,7,8,12,13,14,15,16,17-dodecahydrospiro[cyclopenta[a]phenanthrene-3,2'-[1,3]dioxolan]-17-ol

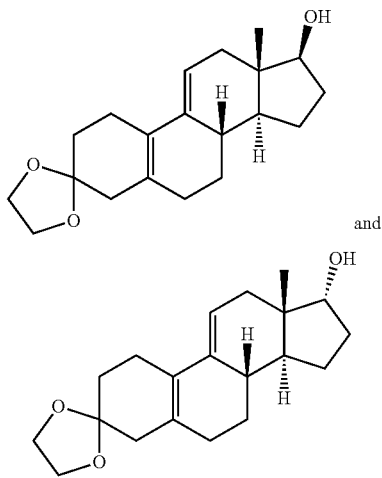

Sodium borohydride (361 mg, 9.54 mmol) was added to a flask charged with (8S,13S,14S)-13-methyl-1,4,6,7,8,12, 13,14,15,16-decahydrospiro[cyclopenta[a]phenanthrene-3, 2'-[1,3]dioxolan]-17(2H)-one (1.0 g, 3.18 mmol) and methanol (15 mL). The mixture was stirred at rt overnight. It was quenched with 2 drops of sat. NaHCO₃ solution and concentrated to remove MeOH. After extraction with EtOAc, the organic phase was washed with sat. NaHCO₃ solution and then brine and dried over anhydrous Na₂SO₄. The mixture was concentrated under reduced pressure and the crude residue was purified by silica gel chromatography, eluting with 10-30% EtOAc in hexanes to provide the title compound as a mixture of epimers (1.0 g, 3.18 mmol, 100% yield) as a colorless oil.

Step B. (5'R,8'S,10'R,13'5,14'S,17'S)-13'-Methyl-1', 2',7',8',12',13',14',15',16',17'-decahydro-4'H,6'H-spiro[[1,3]dioxolane-2,3'-[5,10]epoxycyclopenta[a] phenanthren]-17'-ol and (5'R,8'S,10'R,13'S,14'S, 17'R)-13'-methyl-1',2',7',8',12',13',14',15',16',17'-decahydro-4'H,6'H-spiro[[1,3]dioxolane-2,3'-[5,10] epoxycyclopenta[a]phenanthren]-17'-ol

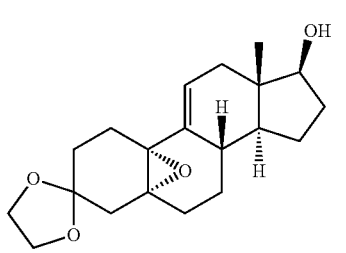

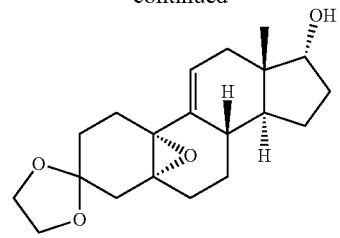

To a solution of (8S,13 S,14S,17S)-13-methyl-1,2,4,6,7, 8,12,13,14,15,16,17-dodecahydrospiro[cyclopenta[a] phenanthrene-3,2'-[1,3]dioxolan]-17-ol and (8S,13S,14S, 17R)-13-methyl-1,2,4,6,7,8,12,13,14,15,16,17-dodecahydrospiro[cyclopenta[a]phenanthrene-3,2'-[1,3] dioxolan]-17-ol (Example 2, Step A) (293 mg, 0.93 mmol) in DCM (7 mL) at 0° C. (ice bath) was added Na₂HPO₄ (328 mg, 2.31 mmol), followed by 1,1,1,3,3,3-hexafluoropropan-2-one trihydrate (0.13 mL, 0.93 mmol) and H₂O₂ (35%, aq) (270 mg, 2.78 mmol). The mixture was stirred at 0° C. for 10 min and then at rt for 110 min. Sodium thiosulfate solution was added and the mixture was stirred at rt for 30 min and extracted with EtOAc. The organic phase was washed with brine and dried over anhydrous Na₂SO₄. The mixture was then concentrated under reduced pressure and the crude residue was purified by silica gel chromatography, eluting with 10-40% EtOAc in hexanes to provide the title compounds as a mixture of epimers (150 mg, 0.45 mmol, 48% yield) as a white solid.

Step C. (5R,8S,11R,13S,14S,17S)-11-(4-(Dimethyl-amino)phenyl)-13-methyl-1,2,6,7,8,11,12,13,14,15, 16,17-dodecahydrospiro[cyclopenta[a]phenanthrene-3,2'-[1,3]dioxolane]-5,17(4H)-diol and (5R,8S,11R, 13S,14S,17R)-11-(4-(dimethylamino)phenyl)-13-methyl-1,2,6,7,8,11,12,13,14,15,16,17-dodecahydrospiro[cyclopenta[a]phenanthrene-3,2'-[1,3]dioxolane]-5,17(4H)-diol

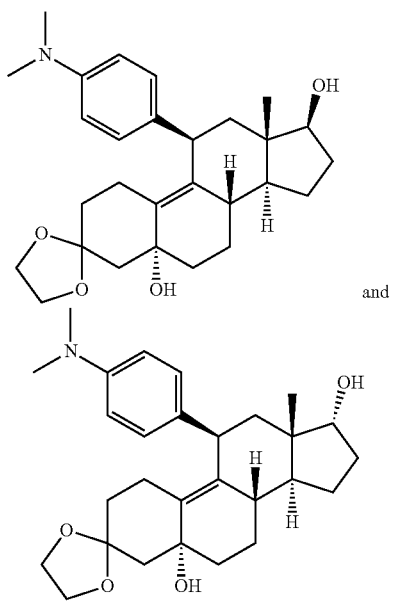

An oven-dried flask was charged with (5'R,8'S,10'R,13'S, 14'S,17'S)-13'-methyl-1',2',7',8',12',13',14',15',16',17'-decahydro-4'H,6'H-spiro[[1,3]dioxolane-2,3'-[5,10]epoxycyclopenta[a]phenanthren]-17'-ol and (5'R,8'S,10'R,13'S,14'S, 17'R)-13'-methyl-1',2',7',8',12',13',14',15',16',17'-decahydro-4'H,6'H-spiro[[1,3]dioxolane-2,3'-[5,10] epoxycyclopenta[a]phenanthren]-17'-ol (Example 2, Step B) (340 mg, 1.02 mmol), copper (I) iodide (155 mg, 0.82 mmol) and THF (5 mL). The mixture was cooled with an ice-bath and degassed with argon. A solution of (4-(dimethylamino)phenyl)magnesium bromide (16.4 mL, 8.18 mmol, 0.5M in THF) was added dropwise. The mixture was stirred at rt for 2 h then quenched with aq. NH₄Cl solution. After extraction with EtOAc, the organic phase was washed with brine and dried over anhydrous Na₂SO₄. The mixture was then concentrated under reduced pressure and the residue was purified by silica gel chromatography, eluting with 20-50% EtOAc in hexanes to provide the title compounds (417 mg, 0.92 mmol, 90% yield).

Step D. (5R,8S,11R,13S,14S)-11-(4-(Dimethylamino)phenyl)-5-hydroxy-13-methyl-1,4,5,6,7,8,11, 12,13,14,15,16-dodecahydrospiro[cyclopenta[a] phenanthrene-3,2'-[1,3]dioxolan]-17(2H)-one

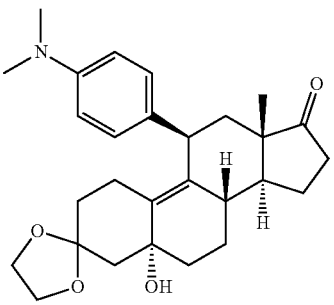

(5R,8S,11R,13S,14S)-11-[4-(Dimethylamino)phenyl]-13-methyl-spiro[1,2,4,6,7,8,11,12,14,15,16,17-dodecahydrocyclopenta[a]phenanthrene-3,2'-1,3-dioxolane]-5,17-diol (epimeric mixture at C17) (Example 2, Step C) (144 mg, 0.32 mmol) after being azeotropically dried with toluene and flushed with argon was dissolved in toluene (5 mL). Cyclohexanone (0.09 mL, 0.91 mmol) was added, followed by aluminum propan-2-olate (87.5 mg, 0.43 mmol). The reaction mixture was stirred at 105° C. for 3 h. After cooling, Rochelle's salt solution was added. The mixture was stirred at rt for 10 min and extracted with EtOAc. The organic phase was washed with brine, dried over anhydrous Na₂SO₄ and concentrated under reduced pressure. The residue was purified by silica gel chromatography eluting with 20-50% EtOAc in hexanes to provide the title compound (95 mg, 0.21 mmol, 66% yield).

Step E. (8S,11R,13S,14S,17S)-11-(4-(Dimethylamino)phenyl)-17-hydroxy-13-methyl-17-(pyridin-2-ylethynyl)-1,2,6,7,8,11,12,13,14,15,16,17-dodecahydro-3H-cyclopenta[a]phenanthren-3-one

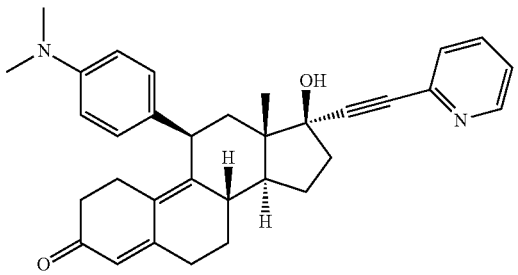

A solution of (5'R,11'R,13'S)-11'-[4-(dimethylamino) phenyl]-5'-hydroxy-13'-methyl-spiro[1,3-dioxolane-2,3'-2, 4,6,7,8,11,12,14,15,16-decahydro-1H-cyclopenta[a] phenanthrene]-17'-one (Example 2, Step D) (30 mg, 0.07 mmol) in THF (1 mL) was added slowly to a preformed mixture of 2-ethynyl pyridine (68.5 mg) and n-butyllithium (0.37 ml, 1.6M in hexanes) in THF (1 ml) at −78° C. (dry ice bath). After warming to rt over 1 h, the mixture was quenched with NH₄Cl solution and extracted into EtOAc. The organic phase was washed with brine, dried over anhydrous Na₂SO₄ and concentrated under reduced pressure. The residue was treated with 70% aq. acetic acid (1.5 ml) for 3 h at 50° C. After cooling rt, the mixture was cautiously quenched into a solution of NaHCO₃ and extracted into EtOAc. The organic phase was washed with brine, dried over anhydrous Na₂SO₄ and concentrated under reduced pressure. The residue was purified by silica gel chromatography eluting with 40-70% EtOAc in hexane to provide the title compound as a yellow solid (5.2 mg, 16%). H NMR (400 MHz, DMSO-d6) δ ppm 8.53 (1H, ddd, J=4.88, 1.95, 0.98 Hz), 7.78 (1H, dd, J=7.71, 1.85 Hz), 7.48 (1H, dt, J=7.91, 1.12 Hz), 7.36 (1H, ddd, J=7.61, 4.88, 1.17 Hz), 7.00 (2H, d, J=7.62 Hz), 6.65 (2H, d, J=8.98 Hz),5.61-5.65 (1H, m), 4.36-4.40 (1H, m), 2.83-2.86 (6H, m), 2.72 (1H, s), 2.62 (1H, br s), 2.46-2.56 (2H, m), 2.29-2.35 (2H, m), 2.02-2.22 (3H, m), 1.87-2.01 (2H, m), 1.63-1.76 (2H, m), 1.28-1.43 (2H, m), 1.20-1.28 (2H, m), 0.48 (3H, s). m/z (ESI, +ve ion) 493.3 (M+H)⁺.

Example 3. (8S,11R,13 S,14S,17S)-11-(3,5-Difluoro-4-methylphenyl)-17-hydroxy-13-methyl-17-((4-(methylsulfonyl)phenyl)ethynyl)-1,2,6,7,8,11,12, 13,14,15,16,17-dodecahydro-3H-cyclopenta[a] phenanthren-3-one

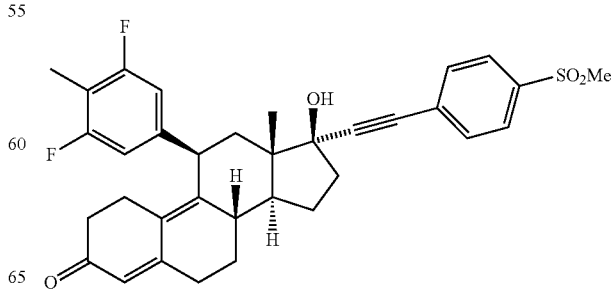

Step A. (8S,13S,14S,17R)-17-Ethynyl-13-methyl-1,2,4,6,7,8,12,13,14,15,16,17-dodecahydrospiro[cyclopenta[a]phenanthrene-3,2'-[1,3]dioxolan]-17-ol

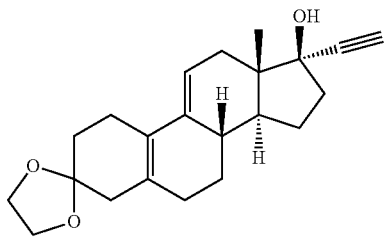

To a stirred solution of (8S,13S,14S)-13-methyl-1,4,6,7,8,12,13,14,15,16-decahydrospiro[cyclopenta[a]phenanthrene-3,2'-[1,3]dioxolan]-17(2H)-one (2 g, 6.4 mmol) in THF (12 mL) at 0° C. was added ethynylmagnesium bromide (0.5 M in THF, 44.5 mL, 22.3 mmol) slowly. The reaction was allowed to warm up to rt and stirred for 60 min. The reaction mixture was quenched (sat. NH₄Cl), extracted (EtOAc), and washed (brine). The combined organic layers were dried (Na₂SO₄) and concentrated under reduced pressure. The residue was purified by flash column chromatography (eluent. 5 to 10% EtOAc in hexane, gradient) to provide 1.1 g of the title compound as a white solid.

Step B. (5R,8S,11R,13S,14S,17R)-11-(3,5-Difluoro-4-methylphenyl)-17-ethynyl-13-methyl-1,2,6,7,8,11,12,13,14,15,16,17-dodecahydrospiro[cyclopenta[a]phenanthrene-3,2'-[1,3]dioxolane]-5,17(4H)-diol

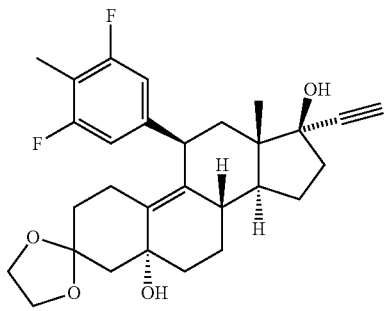

The title compound was prepared from (8S,13S,14S,17R)-17-ethynyl-13-methyl-1,2,4,6,7,8,12,13,14,15,16,17-dodecahydrospiro[cyclopenta[a]phenanthrene-3,2'-[1,3]dioxolan]-17-ol (Example 3, Step A) by procedures similar to those described in Example 1, Steps B and C.

Step C. (8S,11R,13S,14S,17S)-11-(3,5-Difluoro-4-methylphenyl)-17-hydroxy-13-methyl-17-((4-(methylsulfonyl)phenyl)ethynyl)-1,2,6,7,8,11,12,13,14,15,16,17-dodecahydro-3H-cyclopenta[a]phenanthren-3-one (5R,8S,11R,13S,14S,17R)-11-(3,5-difluoro-4-methylphenyl)-17-ethynyl-13-methyl-1,2,6,7,8,11,12,13,14,15,16,17-dodecahydrospiro[cyclopenta[a]phenanthrene-3,2'-[1,3]dioxolane]-5,17(4H)-diol (Example 3, Step B) (180 mg, 0.37 mmol) and 1-bromo-4-methylsulfonyl-benzene (87.33 mg, 0.37 mmol) were dissolved in pyrrolidine (1 mL). Diacetoxypalladium (8.34 mg, 0.04 mmol), copper(I) iodide (7.07 mg, 0.04 mmol) and triphenylphosphine (29.23 mg, 0.11 mmol) were added under argon. After being refluxed for 1 h, the reaction solution was cooled down to rt, quenched with sat. NH₄Cl, extracted with EtOAc. The organic layers were dried over Na₂SO₄ and concentrated. The crude material was dissolved in 70% aq. acetic acid solution (1 mL) and the mixture was stirred at 55° C. for 1.5 h. The mixture was cooled to rt, quenched (sat. NaHCO₃), extracted (EtOAc), and washed (brine). The combined organic layers were dried (MgSO4), and concentrated under reduced pressure. The residue was purified by flash column chromatography (eluent: 10 to 70% EtOAc in hexane, gradient) to give the title compound as a white solid. $^1$H NMR (400 MHz, CDCl₃) δ ppm 7.85 (2H, d, J=8.4 Hz), 7.20 (2H, d, J=8.4 Hz), 6.75-6.60 (2H, m), 5.76 (1H, s), 4.37 (1H, m), 3.10 (3H, s), 2.75-2.25 (10H, m), 2.20 (3H, s), 1.90-0.8 (6H, m), 0.62 (3H, s). m/z (ESI, +ve ion) 577.3 (M+H)⁺.

II. Biological Evaluation

Example 4: In Vitro GR Luciferase Reporter Assay

Cell Line: CHO-K1-GR-MMTV-Luc reporter cells
Culture Media: DMEM (with phenol red)+10% FBS
Assay Media: DMEM (without phenol red)+10% CSS Culture CHO-K1-GR-MMTV-Luc reporter cells in 15 cm plates in Culture Media at conditions less than 90% confluence.

Prepare 200×DMSO 1:5 serial dilutions of control and test compounds in 96-well non-sterile V bottom plate in DMSO, 8 serial dilutions for each compound.

Prepare 5× Assay Media diluted compound serial dilutions in 96-well non-sterile V bottom plate: Add 97.5 uL/well of Assay Media into 96-well then add 2.5 ul of 200× concentration of compounds and mix well.

Seed cells for Antagonist Assay: 1.5×10⁶ CHO-K1-GR-MMTV-Luc reporter cells were seeded in a Corning 3707 flat clear bottom 384-well white TC plate in 20 ul of Assay Media containing 12.5 nM Dexamethasone (final concentration=10 nM).

Add compounds: 5 ul of assay media diluted compounds were added to appropriate wells and followed a quick spin (1000 rpm, 10 sec) to bring media and cells to the bottom of plate. The plates were covered with SealMate film to avoid evaporation and placed in 37° C. incubator for approximately 18-24 hours.

Read plates: Equilibrate appropriate amount of Promega OneGlo luciferase reagent to room temperature. Remove the plates from incubator and add 25 uL of OneGlo reagent/well by multiple channel pipette and read the plates with Tecan F500 luminometer within 3 minutes.

The ability of the compounds disclosed herein to inhibit GR activity was quantified and the respective IC₅₀ value was determined. Table 3 provides the cellular IC₅₀ values of various substituted steroidal compounds disclosed herein.

TABLE 3

| Structure | GR IC$_{50}$ (nM) | Structure | GR IC$_{50}$ (nM) |
|---|---|---|---|
| | A | | A |
| | A | | A |
| | A | | A |
| | A | | A |
| | A | | A |

TABLE 3-continued

| Structure | GR IC$_{50}$ (nM) | Structure | GR IC$_{50}$ (nM) |
|---|---|---|---|
|  | A |  | A |
|  | A |  | A |
|  | B |  | B |
|  | B |  | B |
|  | A |  | A |

TABLE 3-continued

| Structure | GR IC$_{50}$ (nM) | Structure | GR IC$_{50}$ (nM) |
|---|---|---|---|
| | A | | A |
| | A | | A |
| | A | | A |
| | B | | A |
| | B | | B |

TABLE 3-continued

| Structure | GR IC$_{50}$ (nM) | Structure | GR IC$_{50}$ (nM) |
|---|---|---|---|
| | A | | A |
| | A | | A |
| | A | | A |
| | A | | A |
| | A | | A |

TABLE 3-continued

| Structure | GR IC$_{50}$ (nM) | Structure | GR IC$_{50}$ (nM) |
|---|---|---|---|
| | A | | A |
| | A | | A |
| | A | | A |
| | A | | A |
| | A | | A |

TABLE 3-continued

| Structure | GR IC$_{50}$ (nM) | Structure | GR IC$_{50}$ (nM) |
|---|---|---|---|
| | A | | A |
| | A | | A |
| | B | | B |
| | B | | B |
| | B | | B |

TABLE 3-continued

| Structure | GR IC$_{50}$ (nM) | Structure | GR IC$_{50}$ (nM) |
|---|---|---|---|
| (structure) | A | (structure) | A |
| (structure) | A | (structure) | A |
| (structure) | A | (structure) | A |
| (structure) | A | (structure) | A |
| (structure) | A | (structure) | A |

TABLE 3-continued

| Structure | GR IC$_{50}$ (nM) | Structure | GR IC$_{50}$ (nM) |
|---|---|---|---|
| (structure) | A | (structure) | B |
| (structure) | B | — | — |
| (structure) | A | (structure) | B |
| (structure) | A | (structure) | A |
| (structure) | A | (structure) | A |

TABLE 3-continued

| Structure | GR IC$_{50}$ (nM) | Structure | GR IC$_{50}$ (nM) |
|---|---|---|---|
| | A | | A |
| | A | | A |
| | A | | A |
| 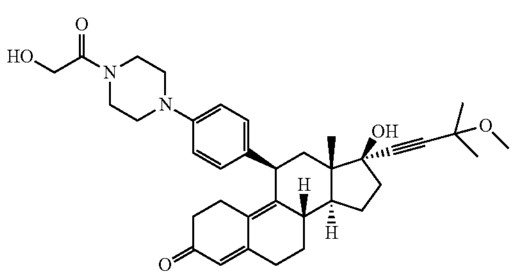 | B | 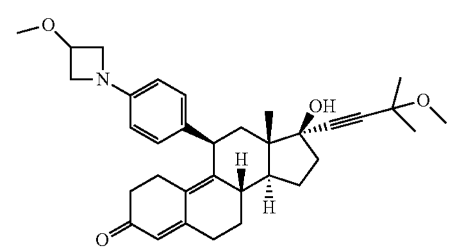 | B |
| | A | | B |
| | A | | A |

TABLE 3-continued

| Structure | GR IC$_{50}$ (nM) | Structure | GR IC$_{50}$ (nM) |
|---|---|---|---|
| | A | | A |
| | B | | A |
| | A | | A |
| | A | | B |
| | B | | A |

TABLE 3-continued

| Structure | GR IC$_{50}$ (nM) | Structure | GR IC$_{50}$ (nM) |
|---|---|---|---|
| [structure] | A | [structure] | A |

Note:
Cellular assay IC$_{50}$ data are designated within the following ranges:
A: ≤100 nM
B: >100 nM

Example 5: In Vitro AR Agonism Assay

The AR agonism assay was done in the LNAR reporter cell line which has overexpressed AR and 4XARE-Luc genes. This cell line is sensitive to even minor partial AR agonism activity in hormone-deprived media (CSS). The assays were done in RPMI (without phenol red)+10% CSS using 6000 LNAR cells/well in 384-well plates and compounds were incubated with cells in 370 C incubator for 18-24 hrs. OneGlo reagent (25 uL/well) was added and plates were read with luminometer within 3 minutes.

Mifepristone shows strong partial AR agonism in concentrations as low as 10 nM, and is known to significantly promote CRPC growth both in vivo and in vitro. To gauge the AR partial agonism activity, Mifepristone is included as a standard in the assay. AR agonism assay results are quantified by determining the ratio of the maximum response of individual compounds to the maximum response of Mifepristone (arbitrarily set to 1). Values of Table 4 are reported as Relative Maximum Response to Mifepristone. This general trend of AR agonism was shown for the class of compounds described herein.

TABLE 4

| Structure | Relative Maximum Response to Mifepristone | Structure | Relative Maximum Response to Mifepristone |
|---|---|---|---|
| [structure] | A | [structure] | A |
| [structure] | A | [structure] | A |

TABLE 4-continued

| Structure | Relative Maximum Response to Mifepristone | Structure | Relative Maximum Response to Mifepristone |
|---|---|---|---|
| | A | | A |
| | A | | A |
| | A | | A |
| | A | | A |
| | A | | A |

TABLE 4-continued

| Structure | Relative Maximum Response to Mifepristone | Structure | Relative Maximum Response to Mifepristone |
|---|---|---|---|
| | A | | A |
| 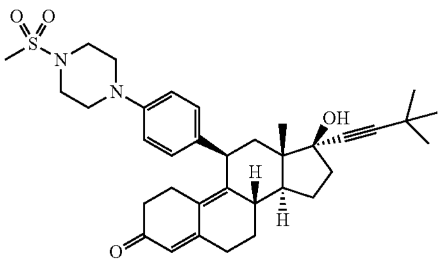 | B | 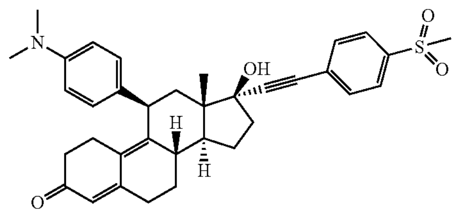 | B |
| | A | | A |

Note:
AR agonism response assay data relative maximum response to Mifepristone is designated within the following ranges:
A: ≤0.4
B: >0.4

What is claimed is:

1. A compound having the structure of Formula (I), or a pharmaceutically acceptable salt, solvate, or prodrug thereof:

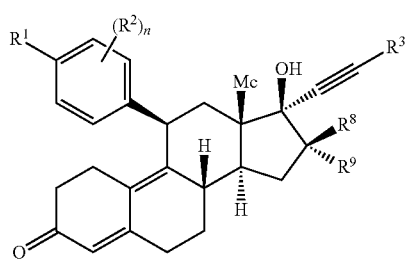

Formula (I)

wherein
R$^1$ is —NR$^4$R$^5$;
each R$^2$ is independently —NR$^4$R$^5$, alkylNR$^4$R$^5$, halo, —OR$^6$, —OH, alkyl, haloalkyl, carbocyclyl, carbocyclylalkyl, heteroalkyl, heterocyclyl, heterocyclylalkyl, hydroxyalkyl, —C(O)R$^6$, —C(O)OR$^6$, —C(O)NR$^4$R$^5$, —OC(O)OR$^6$, —OC(O)NR$^4$R$^5$, —S(O)$_2$NR$^4$R$^5$, —S(O)$_2$R$^7$, —S(O)R$^7$, —SR$^7$, —NR$^4$S(O)$_2$NR$^4$R$^5$, —CN, —CO$_2$H, or —NO$_2$;

R$^3$ is t-butyl;

R$^4$ and R$^5$ are each independently —H, alkyl optionally substituted with —OR$^6$, haloalkyl, carbocyclyl, aryl, heterocyclyl, heteroaryl, —S(O)$_2$R$^7$, —C(O)N(R$^{10}$)$_2$, —C(O)R$^6$, or —C(O)OR$^6$;

or R$^4$ and R$^5$ attached to the same N atom are taken together with the N atom to which they are attached to form a heterocycle optionally substituted with alkyl optionally substituted with —OH, —OH, —OR$^6$, —S(O)$_2$R$^7$, —C(O)N(R$^{10}$)$_2$, —C(O)R$^6$, or —C(O)OR$^6$;

each R$^6$ is independently alkyl optionally substituted with —OH, haloalkyl, carbocyclyl, aryl, heterocyclyl, or heteroaryl;

R$^7$ is alkyl, haloalkyl, carbocyclyl, heteroalkyl, aryl, aralkyl, heterocyclyl, or heteroaryl;

R$^8$ and R$^9$ are each —H;

each R$^{10}$ is independently H, alkyl, haloalkyl, carbocyclyl, heteroalkyl, aryl, aralkyl, heterocyclyl, or heteroaryl; and n is 0, 1, 2, 3, or 4.

2. The compound of claim 1, or a pharmaceutically acceptable salt, solvate, or prodrug thereof, wherein each $R^2$ is independently —$NR^4R^5$, halo, alkyl, carbocyclyl, alkoxy, or —CN.

3. The compound of claim 1, or a pharmaceutically acceptable salt, solvate, or prodrug thereof, wherein $R^4$ and $R^5$ are each independently —H, alkyl, or —$S(O)_2R^7$.

4. The compound of claim 1, or a pharmaceutically acceptable salt, solvate, or prodrug thereof, wherein
$R^4$ and $R^5$ attached to the same N atom are taken together with the N atom to which they are attached to form a 4-, 5-, or 6-membered ring heterocycle additionally containing 0-3 heteroatoms selected from the group consisting of —O—, —NH—, —$NR^6$—, —S—, and —$S(O)_2$—; and
$R^6$ is alkyl.

5. The compound of claim 1, or a pharmaceutically acceptable salt, solvate, or prodrug thereof, wherein $R^6$ is alkyl, carbocyclyl, or fluoroalkyl.

6. The compound of claim 1, or a pharmaceutically acceptable salt, solvate, or prodrug thereof, wherein $R^7$ is alkyl, carbocyclyl, aryl, aralkyl, or heterocyclyl.

7. The compound of claim 1, or a pharmaceutically acceptable salt, solvate, or prodrug thereof, wherein n is 0.

8. The compound of claim 1, or a pharmaceutically acceptable salt, solvate, or prodrug thereof, wherein n is 1.

9. The compound of claim 1, or a pharmaceutically acceptable salt, solvate, or prodrug thereof, wherein n is 2.

10. A pharmaceutical composition comprising a compound of claim 1, or a pharmaceutically acceptable salt, solvate, or prodrug thereof, and at least one pharmaceutically acceptable excipient.

11. A method for treating cancer in a subject, the method comprising administering a therapeutically effective amount of a compound of claim 1, or a pharmaceutically acceptable salt, solvate, or prodrug thereof, to the subject in need thereof, wherein the cancer is triple negative breast cancer, high grade serous ovarian cancer, castration resistant prostate cancer, doubly resistant prostate cancer, or non-small cell lung cancer.

12. A method for treating a chemo-resistant cancer in a subject, the method comprising administering a therapeutically effective amount of a compound of claim 1, or a pharmaceutically acceptable salt, solvate, or prodrug thereof, to the subject in need thereof, wherein the cancer is triple negative breast cancer, high grade serous ovarian cancer, castration resistant prostate cancer, doubly resistant prostate cancer, or non-small cell lung cancer.

13. The method of claim 11, wherein the cancer is triple negative breast cancer, high grade serous ovarian cancer, castration resistant prostate cancer, or doubly resistant prostate cancer.

14. The method of claim 11, wherein the cancer is non-small cell lung cancer.

15. The method of claim 11, further comprising administering one or more additional therapeutic agents to the subject.

16. The method of claim 15, wherein the one or more additional therapeutic agents are androgen receptor signaling inhibitors.

17. The method of claim 16, wherein the androgen receptor signaling inhibitor is 3,3'-diindolylmethane (DIM), abiraterone acetate, ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, turosternde, or any combinations thereof.

18. The compound of claim 1, or a pharmaceutically acceptable salt, solvate, or prodrug thereof, wherein the compound has the structure:

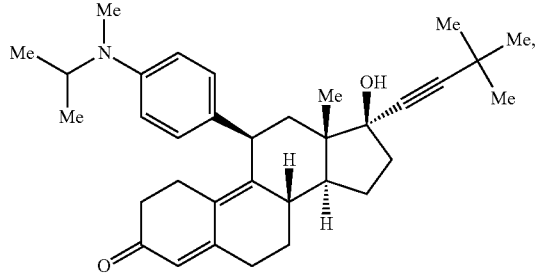

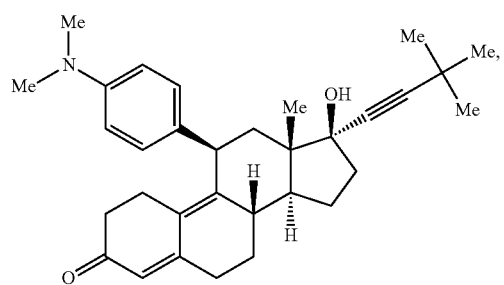

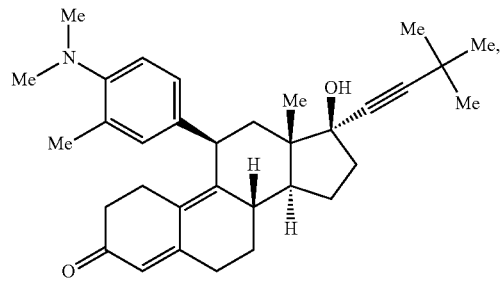

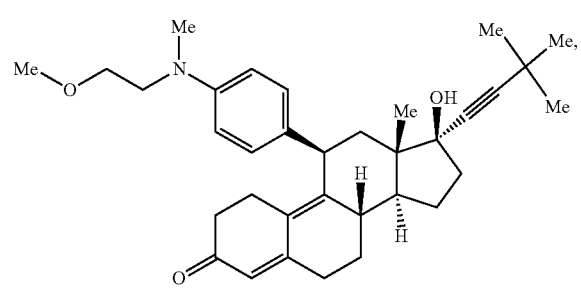

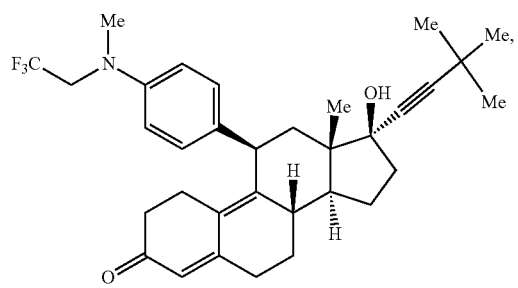

193
-continued
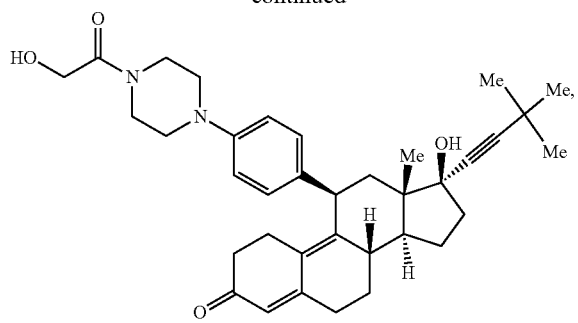
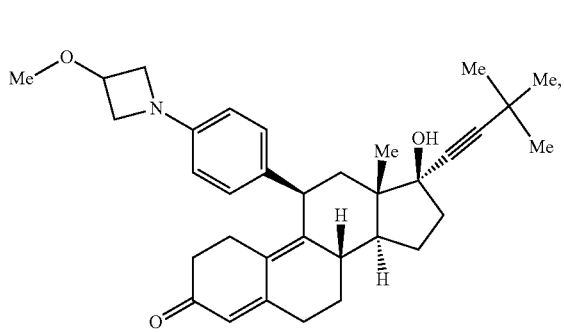
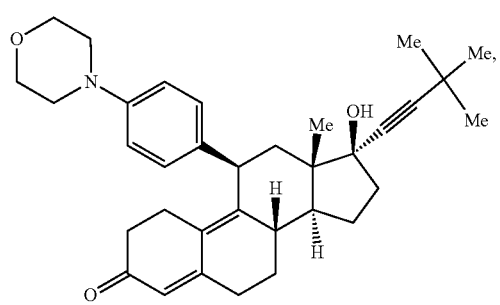
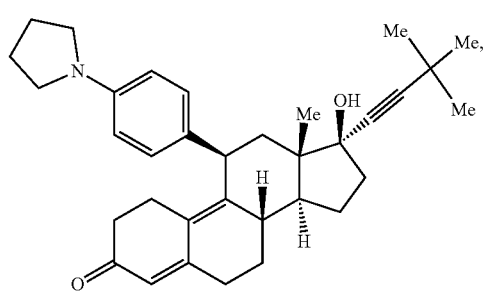
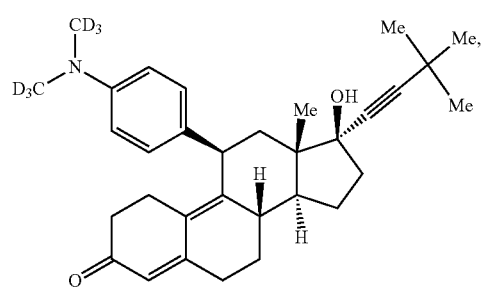
194
-continued
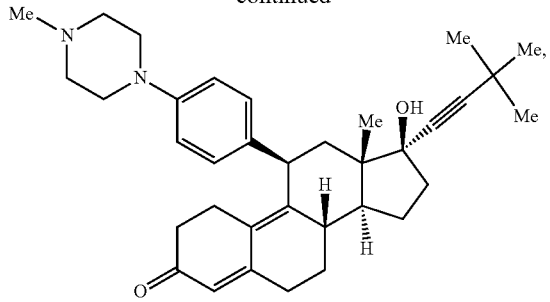
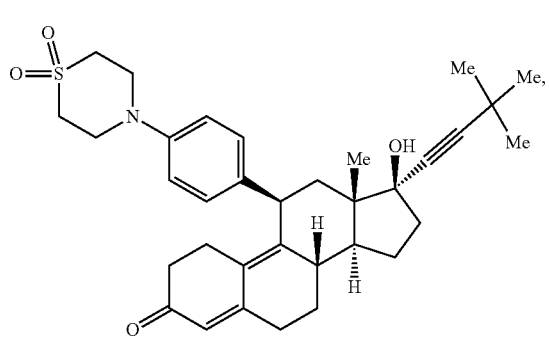
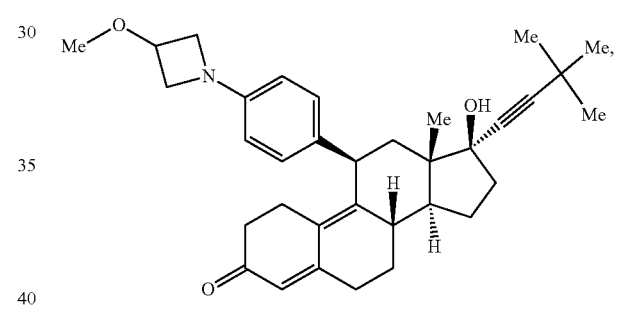
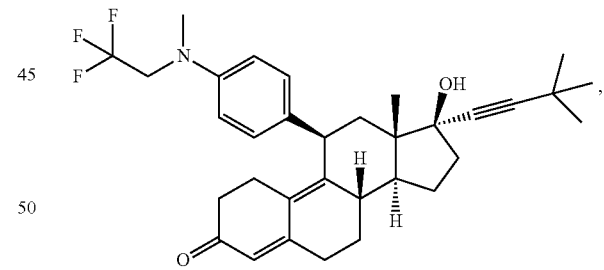
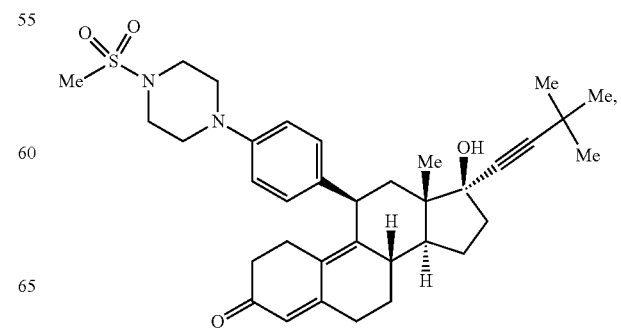

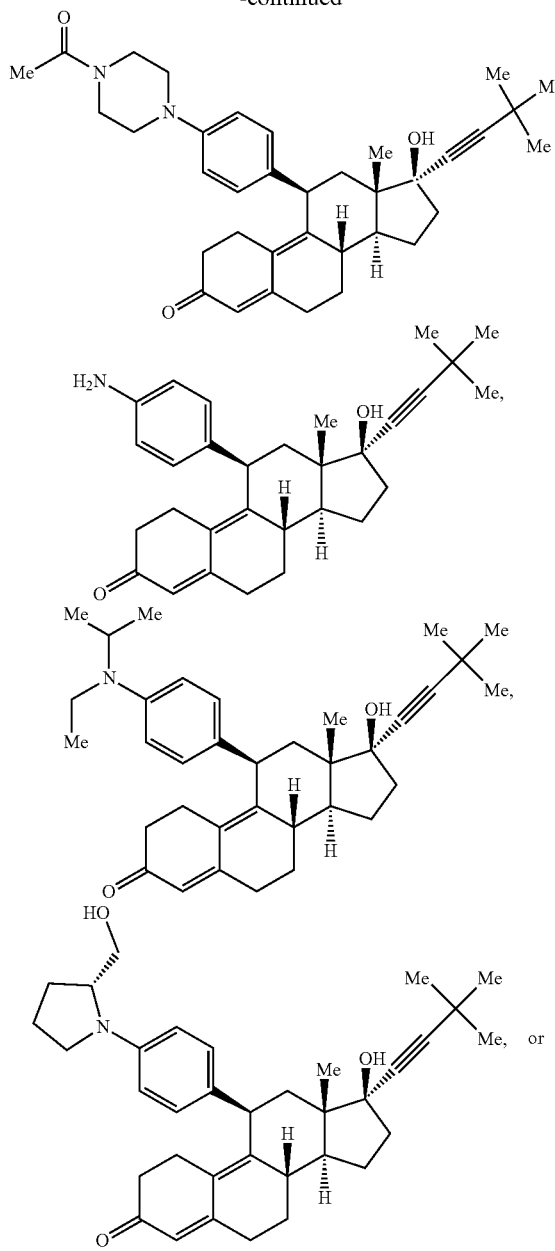

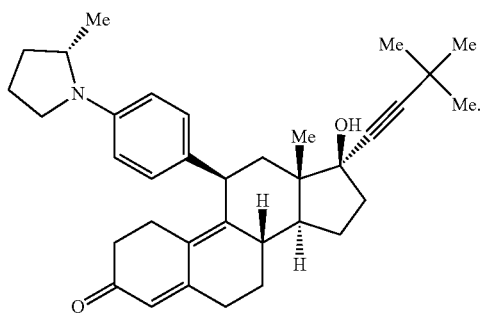

19. A pharmaceutical composition comprising a compound of claim 18, or a pharmaceutically acceptable salt, solvate, or prodrug thereof, and at least one pharmaceutically acceptable excipient.

20. A method for treating cancer in a subject, the method comprising administering a therapeutically effective amount of a compound of claim 18, or a pharmaceutically acceptable salt, solvate, or prodrug thereof, to the subject in need thereof, wherein the cancer is triple negative breast cancer, high grade serous ovarian cancer, castration resistant prostate cancer, doubly resistant prostate cancer, or non-small cell lung cancer.

21. The method of claim 20, further comprising administering one or more additional therapeutic agents to the subject.

22. The method of claim 21, wherein the one or more additional therapeutic agents are androgen receptor signaling inhibitors.

23. The method of claim 22, wherein the androgen receptor signaling inhibitor is 3,3'-diindolylmethane (DIM), abiraterone acetate, ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, turosteride, or any combinations thereof.

* * * * *